(12) United States Patent
Tanaka et al.

(10) Patent No.: US 7,919,653 B2
(45) Date of Patent: Apr. 5, 2011

(54) METHOD OF INHIBITING NONSPECIFIC INTERACTION BETWEEN MOLECULES ON SOLID PHASE SUPPORT

(75) Inventors: Akito Tanaka, Ibaraki (JP); Tomohiro Terada, Ibaraki (JP); Tsuruki Tamura, Ibaraki (JP); Takaaki Shiyama, Osaka (JP); Akira Yamazaki, Osaka (JP); Minoru Furuya, Chiba (JP); Masayuki Haramura, Kanagawa (JP)

(73) Assignees: Reverse Proteomics Research Institute Co., Ltd., Kisarazu-shi (JP); Astellas Pharma Inc., Tokyo (JP)

( * ) Notice: Subject to any disclaimer, the term of this patent is extended or adjusted under 35 U.S.C. 154(b) by 1406 days.

(21) Appl. No.: 10/522,716

(22) PCT Filed: Jul. 30, 2003

(86) PCT No.: PCT/JP03/09640
§ 371 (c)(1),
(2), (4) Date: Jan. 20, 2006

(87) PCT Pub. No.: WO2004/025297
PCT Pub. Date: Mar. 25, 2004

(65) Prior Publication Data
US 2006/0177943 A1    Aug. 10, 2006

(30) Foreign Application Priority Data
Jul. 30, 2002   (JP) ................................ 2002-222226

(51) Int. Cl.
*G01N 33/53* (2006.01)
*G01N 37/00* (2006.01)
*G01N 33/543* (2006.01)

(52) U.S. Cl. ...................................... 562/561; 562/553
(58) Field of Classification Search ........................ None
See application file for complete search history.

(56) References Cited

U.S. PATENT DOCUMENTS
2004/0092015 A1    5/2004   Bonnet et al.

FOREIGN PATENT DOCUMENTS

| EP | 0 164 889 A2 | 12/1985 |
|---|---|---|
| EP | 0 460 239 | 12/1991 |
| EP | 0 628 819 | 12/1994 |
| JP | 61-252215 | 11/1986 |
| JP | 5-340948 | 12/1993 |
| JP | 06 298672 | 10/1994 |
| JP | 7-027767 | 1/1995 |
| JP | 11-287802 | 10/1999 |
| JP | 2002 317074 | 10/2002 |
| WO | 02/20558 | 3/2002 |

OTHER PUBLICATIONS

Chapman et al. Langmuir 2000, 16, pp. 6927-6936.*
Dhawan et al Bioconjugate chemistry 2000, 11, pp. 14-21.*
Akerblom et al. Bioconjugate Chem., 1993, 4, 455-466.*
Karel Kefurt, et al.; "6-Amino-6-Deoxyhexonolactams", Collection of Czechoslovak Chemical Communication vol. 53, No. 8, pp. 1795-1805, 1988.
Jean-Sebastien Fruchart, et al., "A New Linker for the Synthesis of C-Terminal Peptide α-OXO-Aldehydes", Tetrahedron Letters, vol. 40, No. 34, pp. 6225-6228, 1999.
Makoto Hashimoto, et al., "Cell-Surface Recognition of Biotinylated Membrane Proteins Requires Very Long Spacer Arms: An Example From Glucose-Transporter Probes", Chembiochem, , vol. 2, No. 1, pp. 52-59, 2001.
Naoya Ogata, et al., Polycondensation of Diethy L Mucate With Hexamethylendiamine in the Presence of Poly (Viny L) Pyridine), Journal of Polymer Science: Polymer Chemistry Edition, vol. 18, pp. 933-938, 1980.
Database Chemical Abstracts Service, Sep. 15, 1999, Database accession No. 1999:577640.
Database Chemical Abstracts Service, Aug. 10, 1999, Database accession No. 1999:496481.
Naoya Ogata, et al., "Cellular Affinity of Polyamides Having Various Functional Groups. I. Platelet Adhesion", Journal of Applied Polymer Science, vol. 26, No. 7, pp. 2293-2303, 1981.
Christophe Olivier, et al., "Fabrication of Peptide Microarrays on Semicarbazide Glass Slides", Peptides 2002, pp. 992-993.

* cited by examiner

*Primary Examiner* — Daniel M Sullivan
*Assistant Examiner* — Yevegeny Valenrod
(74) *Attorney, Agent, or Firm* — Oblon, Spivak, McClelland, Maier & Neustadt, L.L.P.

(57) ABSTRACT

The present invention provides a method of suppressing the nonspecific interaction between molecules, characterized in that in a process to immobilize a molecule onto a solid phase carrier and analyze the specific interaction between the molecule and a molecule that specifically interacts with the molecule on the solid phase, the hydrophobic property of the solid phase surface in the solid phase carrier is regulated, particularly a hydrophilic spacer is interlaid at the time of immobilization of the molecule onto the solid phase carrier, which method makes it possible to suppress the nonspecific interaction between the molecules, and to reduce nonspecific adsorption to the solid phase.

15 Claims, 2 Drawing Sheets

METHOD OF INHIBITING NONSPECIFIC INTERACTION BETWEEN MOLECULES ON SOLID PHASE SUPPORT

TECHNICAL FIELD

The present invention relates to a basic technology in intermolecular interactions using a solid phase carrier. More specifically, the present invention relates to a technology to immobilize a molecule to be analyzed onto a solid phase carrier, and to measure and analyze the intermolecular interaction on the solid phase by making use of the interaction, whereby a molecule exhibiting a specific interaction with the molecule to be analyzed (hereinafter also referred to as target molecule) is selected and purified or the specific interaction between the molecules is analyzed.

BACKGROUND ART

In recent years, attempts to search a molecule that exhibits a specific interaction with a particular molecule using a technique based on intermolecular interactions, or research to investigate intermolecular interactions in detail, has been actively conducted. This is specifically represented by research wherein one molecule of the combination of small molecule-small molecule, small molecule-large molecule, or large molecule-large molecule is immobilized onto a solid phase carrier and the interaction between the two molecules is measured, or research wherein a desired target (a molecule that exhibits a specific interaction with a molecule immobilized onto a solid phase carrier) is purified on the basis thereof. As examples of various techniques based on intermolecular interactions, 1) target research using an affinity resin for the latter case, and 2) a method that applies surface plasmon resonance (Surface Plasmon Resonanse: SPR) for the former case, are known well. As examples of 1), the discovery of FKBP proteins, which bind to the immunosuppressant FK506 (FK506 binding proteins) using an affinity resin by Professor Schreiber in 1989 (discovery of FKBP12 as a protein that binds to FK506 in cells, Nature, 341, 758, 1989), the subsequently done discovery of calcineurin inhibitory action in the pharmacological action mechanism of FK506 by an FK506-FKBP complex (Cell, 66, 807-815, 1991), the discovery of HDAC as a target protein for the anticancer agent Trapoxin (Science, 272, 408, 1996) and the like are known well. Also, as an example of 2), BIACORE (trade name), which employs a gold foil as a solid phase carrier and enables an extensive investigation of an interaction between a compound or a protein and the like and a protein and the like that specifically interacts therewith, is known well.

However, to date, in the above-described techniques, the presence of a nonspecific intermolecular interaction that hampers the selection and purification of a desired molecule based on a specific intermolecular interaction has been posing such problems as 1) in target search using an affinity resin, a nonspecific protein that masks a specific protein during analysis of a protein bound to an affinity resin using SDS gel and the like exists and makes the detection of the specific protein difficult, or 2) in analysis using BIACORE and the like, the presence of a peak resulting from major nonspecific protein adsorption makes the distinguishing of a peak due to specific protein binding. Although these have empirically been considered as being caused by the solid phase carrier, which is an important basic technology, specifically by a surface property of the solid phase carrier, it remains yet to be known clearly which property is the causal factor for a nonspecific interaction, and how to efficiently suppress such a nonspecific intermolecular interaction. For example, some resins such as TentaGel (Fluka Company, Cat. No=86364) have a PEG spacer, are chemically and physically stable, and are also used as resins for affinity chromatography (e.g., Thorpe D S, Walle S., Combinatorial chemistry defines general properties of linkers for the optimal display of peptide ligands for binding soluble protein targets to TentaGel microscopic beads, Biochem Biophys Res Commun 2000 Mar. 16; 269(2):591-5), but basic technologies such as those concerning the identity of the structure that contributes to suppression of a nonspecific interaction and the way of the contribution remain unknown, and there is no sufficient information on to which extent the nonspecific interaction is suppressed or whether or not these resins serve well as affinity resins.

As such PEG spacers, TentaGel, which is described above, and ArgoGel (Argonaut Company) are commercially available. Their structures are as follows

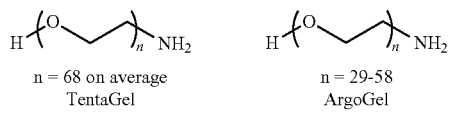

n = 68 on average  
TentaGel n = 29-58  
ArgoGel

Also, resins comprising a sugar derivative having hydrophilic nature (for example, AffiGel (AffiGel; Bio-Rad Company, Cat. No=153-2401), a Sepharose derivative (Pharmacia Company, ECH Sepharose 4B, Cat. No=17-0571-01) and the like are known) exhibit minor nonspecific intermolecular interactions, but they are physically and chemically unstable because of their identity as sugar derivatives and their use is limited.

If it is possible to artificially suppress nonspecific interactions in the above-described techniques based on intermolecular interactions, it is considered that the necessity of determining whether the results obtained are due to specific protein binding or nonspecific protein adsorption will be obviated, the frequency of research interruption due to the substantial inability to differentiate both thereof will decrease, and the consumption of protein and the like used will be significantly reduced, so that significant cost reductions in terms of time and labor, and the like will increase the applicability of these techniques.

It is an object of the present invention to provide a method of eliminating or suppressing a nonspecific interaction that hampers the analysis of intermolecular interactions on a solid phase carrier, and it is another object to provide a method of purifying and analyzing a molecule that exhibits a specific interaction with a molecule immobilized onto a solid phase carrier using the method described above.

DISCLOSURE OF THE INVENTION

The present inventors conducted an investigation wherein a particular small compound as a ligand is immobilized onto a solid phase surface in a solid phase carrier, and a molecule that specifically interacts with the ligand immobilized (target molecule) or a molecule that nonspecifically interacts with the same is quantitatively observed, with the aim of solving the above-described problems, and found that there is a correlation between a hydrophobicity parameter of the compound to be immobilized (ligand) and a nonspecific interaction, that is, the hydrophobic property of the solid phase surface can serve as a factor that causes a nonspecific interaction between molecules. Furthermore, on the basis of this finding, the inventors succeeded in suppressing a nonspecific interaction by introducing a hydrophilic spacer to the binding of the solid phase surface and the ligand that is the subject molecule, and developed the present invention.

That is, the present invention is as follows.

(1) A method of regulating the nonspecific adsorption of a molecule to a solid phase surface, comprising regulating the hydrophobic property of the solid phase surface in a solid phase carrier.

(2) A method of suppressing the nonspecific interaction between a molecule A and/or a solid phase carrier and a molecule other than a molecule B that specifically interacts with said molecule A, comprising conducting a treatment to reduce the hydrophobic property of the solid phase surface in the solid phase carrier, in a process to immobilize the molecule A onto the solid phase carrier and analyze the specific interaction between the molecule A and the molecule B on the solid phase.

(3) A method of suppressing the nonspecific interaction between a molecule A and/or a solid phase carrier and a molecule other than a molecule B that specifically interacts with said molecule A, comprising conducting a treatment to reduce the hydrophobic property of the solid phase surface in the solid phase carrier, in a process to immobilize the molecule A onto the solid phase carrier and select the molecule B using the specific interaction between the molecule A and the molecule B on the solid phase.

(4) The method described in (2) or (3) above, wherein the combination of the molecule A and the molecule B is any of a small compound and a small compound, a small compound and a large compound, and a large compound and a large compound.

(5) The method described in (2) or (3) above, wherein the combination of the molecule A and the molecule B is a small compound and a large compound or a large compound and a large compound.

(6) The method described in (2) or (3) above, wherein the treatment to reduce the hydrophobic property of the solid phase surface in the solid phase carrier is to introduce, at the time of immobilization of the molecule A onto the solid phase carrier, a hydrophilic spacer therebetween.

(7) The method described in (6) above, wherein the hydrophilic spacer has at least any of the following characteristics while in a state bound to the solid phase carrier and the molecule A:

(i) the number of hydrogen bond acceptor is 6 or more,
(ii) the number of hydrogen bond donor is 5 or more,
(iii) the total number of hydrogen bond acceptor and hydrogen bond donor is 9 or more.

(8) The method described in (7) above, wherein said hydrophilic spacer further has one or more carbonyl groups in the molecule thereof.

(9) The method described in (7) or (8) above, further characterized in that said hydrophilic spacer does not have a functional group that becomes positively or negatively charged in an aqueous solution.

(10) A method of immobilizing a molecule A onto a solid phase carrier, and analyzing the specific interaction between the molecule A and a molecule B that specifically interacts with said molecule A, on the solid phase, comprising suppressing the nonspecific interaction between the molecule A and/or the solid phase carrier and a molecule other than the molecule B by conducting a treatment to reduce the hydrophobic property of the solid phase surface in the solid phase carrier.

(11) A method of immobilizing a molecule A onto a solid phase carrier, and selecting a molecule B that specifically interacts with said molecule A using the specific interaction between the molecule A and the molecule B on the solid phase, comprising suppressing the nonspecific interaction between the molecule A and/or the solid phase carrier and a molecule other than the molecule B by conducting a treatment to reduce the hydrophobic property of the solid phase surface in the solid phase carrier.

(12) The method described in (10) or (11) above, wherein the combination of the molecule A and the molecule B is any of a small compound and a small compound, a small compound and a large compound, and a large compound and a large compound.

(13) The method described in (10) or (11) above, wherein the combination of the molecule A and the molecule B is a small compound and a large compound or a large compound and a large compound.

(14) The method described in (10) or (11) above, wherein the treatment to reduce the hydrophobic property of the solid phase surface in the solid phase carrier is to introduce, at the time of immobilization of the molecule A onto the solid phase carrier, a hydrophilic spacer therebetween.

(15) The method described in (14) above, wherein the hydrophilic spacer has at least any of the following characteristics while in a state bound to the solid phase carrier and the molecule A:

(i) the number of hydrogen bond acceptor is 6 or more,
(ii) the number of hydrogen bond donor is 5 or more,
(iii) the total number of hydrogen bond acceptor and hydrogen bond donor is 9 or more.

(16) The method described in (15) above, wherein said hydrophilic spacer further has one or more carbonyl groups in the molecule thereof.

(17) The method described in (15) or (16) above, further characterized in that said hydrophilic spacer does not have a functional group that becomes positively or negatively charged in an aqueous solution.

(18) A screening method for a molecule B that exhibits a specific interaction with a molecule A, comprising at least the following steps:

(i) immobilizing the molecule A onto a solid phase carrier via a hydrophilic spacer,
(ii) contacting a sample that contains or does not contain the molecule B with the solid phase carrier with the molecule A immobilized thereon obtained in (i) above,
(iii) identifying and analyzing a molecule that has exhibited or has not exhibited a specific interaction with the molecule A, and
(iv) judging a molecule that exhibits a specific interaction with the molecule A as the molecule B on the basis of the analytical results obtained in (iii) above.

(19) The method described in (18) above, wherein the combination of the molecule A and the molecule B is any of a small compound and a small compound, a small compound and a large compound, and a large compound and a large compound.

(20) The method described in (18) above, wherein the combination of the molecule A and the molecule B is a small compound and a large compound or a large compound and a large compound.

(21) The method described in (18) above, wherein the hydrophilic spacer has at least any of the following characteristics while in a state bound to the solid phase carrier and the molecule A:

(i) the number of hydrogen bond acceptor is 6 or more,
(ii) the number of hydrogen bond donor is 5 or more,
(iii) the total number of hydrogen bond acceptor and hydrogen bond donor is 9 or more.

(22) The method described in (21) above, wherein said hydrophilic spacer further has one or more carbonyl groups in the molecule thereof.

(23) The method described in (21) or (22) above, further characterized in that said hydrophilic spacer does not have a functional group that becomes positively or negatively charged in an aqueous solution.

(24) A hydrophilic spacer for reducing the hydrophobic property of the solid phase surface in a solid phase carrier, which has at least any of the following characteristics while in a state bound to the solid phase carrier and the molecule A:

(i) the number of hydrogen bond acceptor is 6 or more, (ii) the number of hydrogen bond donor is 5 or more, (iii) the total number of hydrogen bond acceptor and hydrogen bond donor is 9 or more.

(25) The hydrophilic spacer described in (24) above, wherein said hydrophilic spacer further has one or more carbonyl groups in the molecule thereof.

(26) The hydrophilic spacer described in (24) or (25) above, further characterized in that said hydrophilic spacer does not have a functional group that becomes positively or negatively charged in an aqueous solution.

(27) A complex that comprises a solid phase carrier and the hydrophilic spacer described in any one of (24)-(26) above.

(28) A complex that comprises the hydrophilic spacer described in any one of (24)-(26) above and a molecule A.

(29) A complex that comprises a solid phase carrier, the hydrophilic spacer described in any one of (24)-(26) above, and a molecule A.

(30) The hydrophilic spacer described in any one of (24)-(26) above, which has at least one partial structure represented by any one formula selected from the group consisting of Formulas (Ia)-(Ie) below:

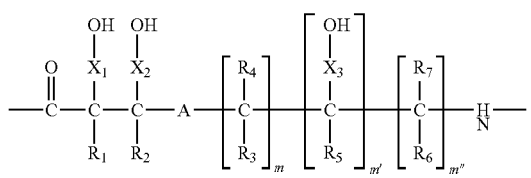
(Ia)

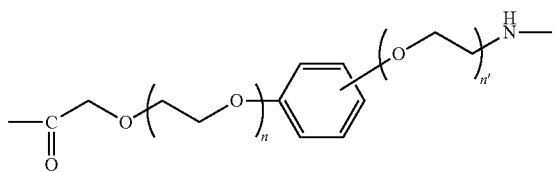
(Ib)

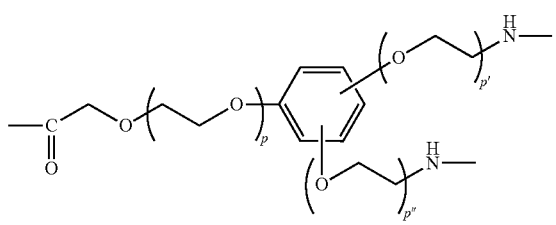
(Ic)

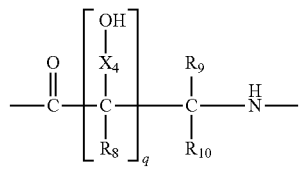
(Id)

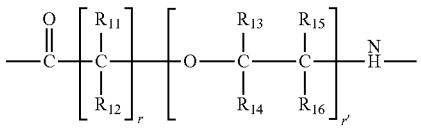
(Ie)

(In Formula (Ia),

A is an appropriate joining group, $X_1$-$X_3$ are the same or different and each is a single bond or a methylene group that may be substituted by a linear or branched alkyl group having 1-3 carbon atoms, $R_1$-$R_7$ are the same or different and each is a hydrogen atom, a linear or branched alkyl group having 1-3 carbon atoms, —$CH_2OH$ or a hydroxyl group, m is an integer of 0-2, m' is an integer of 0-10, m" is an integer of 0-2, when a plurality of $R_3$-$R_7$ units exist, they may be the same or different, when a plurality of $X_3$ units exist, they may be are the same or different;

in Formula (Ib), n and n' are the same or different and each is an integer of 1-1000;

in Formula (Ic), p, p' and p" are the same or different and each is an integer of 1-1000;

in Formula (Id), $X_4$ is a single bond or a methylene group that may be substituted by a linear or branched alkyl group having 1-3 carbon atoms, $R_8$-$R_{10}$ are the same or different and each is a hydrogen atom, a linear or branched alkyl group having 1-3 carbon atoms, —$CH_2OH$ or a hydroxyl group, q is an integer of 1-7, when a plurality of $R_8$ units exist, they may be the same or different, when a plurality of $X_4$ units exist, they may be the same or different;

in Formula (Ie), $R_{11}$-$R_{16}$ are the same or different and each is a hydrogen atom, a linear or branched alkyl group having 1-3 carbon atoms, —$CH_2OH$ or a hydroxyl group, r is an integer of 1-10, r' is an integer of 1-50, when a plurality of $R_{11}$-$R_{16}$ units exist, they may be the same or different).

(31) The hydrophilic spacer described in (30) above, which has two or more partial structures represented by any one formula selected from the group consisting of Formulas (Ia)-(Ie).

(32) A complex that comprises a solid phase carrier and the hydrophilic spacer described in (30) or (31) above.

(33) A complex that comprises the hydrophilic spacer described in (30) or (31) above and a molecule A.

(34) A complex that comprises a solid phase carrier, the hydrophilic spacer described in (30) or (31) above, and a molecule A.

(35) A compound that has at least one partial structure represented by any one formula selected from the group consisting of Formulas (Ia)-(Ie), but excluding the following compound:

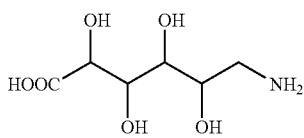

(36) The compound described in (35) above, which has two or more partial structures represented by any one formula selected from the group consisting of Formulas (Ia)-(Ie).

(37) A compound represented by at least one formula selected from the group consisting of Formulas (IIa)-(IIe) below:

(IIa)

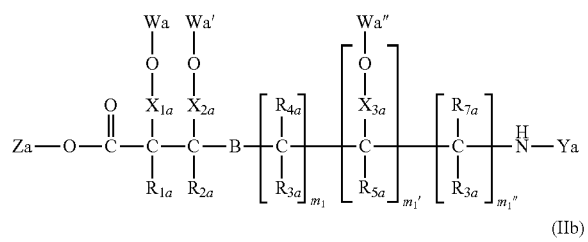

(IIb)

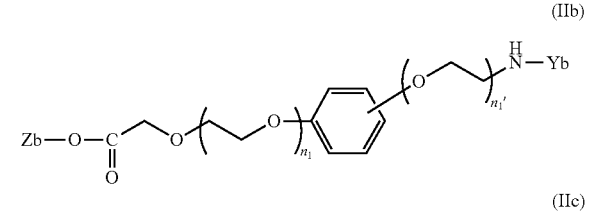

(IIc)

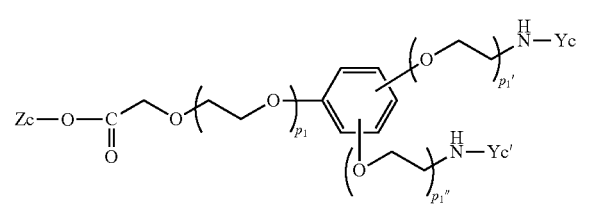

(IId)

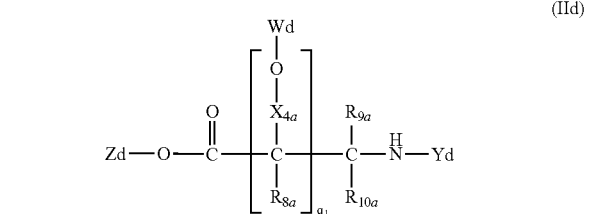

(IIe)

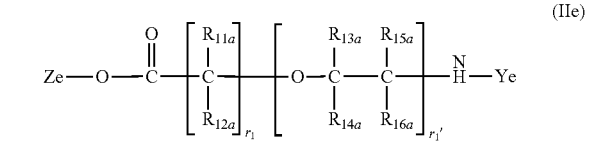

(In Formula (IIa),
Ya is a hydrogen atom or an amino-group-protecting group,
Za is a hydrogen atom or a carboxyl-group-protecting group,
Wa, Wa' and Wa" are the same or different and each is a hydrogen atom or a hydroxyl-group-protecting group (these protective groups may bind together with mutually adjoining protective groups to form a dialkylmethylene group),
B is an appropriate joining group,
$X_{1a}$-$X_{3a}$ are the same or different and each is a single bond or a methylene group that may be substituted by a linear or branched alkyl group having 1-3 carbon atoms,
$R_{1a}$-$R_{7a}$ are the same or different and each is a hydrogen atom, a linear or branched alkyl group having 1-3 carbon atoms, —$CH_2OH$ (in the formula, the hydroxyl group may be protected) or a hydroxyl group that may be protected,
$m_1$ is an integer of 0-2, $m_1'$ is an integer of 0-10, $m_1''$ is an integer of 0-2,
when a plurality of $R_{3a}$-$R_{7a}$ units exist, they may be the same or different, when a plurality of $X_{3a}$ units exist, they may be the same or different;
in Formula (IIb),
Yb is a hydrogen atom or an amino-group-protecting group,
Zb is a hydrogen atom or a carboxyl-group-protecting group,
$n_1$ and $n_1'$ are the same or different and each is an integer of 1-1000;
in Formula (IIc),
Yc and Yc' are the same or different and each is a hydrogen atom or an amino-group-protecting group,
Zc is a hydrogen atom or a carboxyl-group-protecting group,
$p_1$, $p_1'$ and $p_1''$ are the same or different and each is an integer of 1-1000;
in Formula (IId),
Yd is a hydrogen atom or an amino-group-protecting group,
Zd is a hydrogen atom or a carboxyl-group-protecting group,
Wd is a hydrogen atom or a hydroxyl group-protecting group,
$X_{4a}$ is a single bond or a methylene group that may be substituted by a linear or branched alkyl group having 1-3 carbon atoms,
$R_{8a}$-$R_{10a}$ are the same or different and each is a hydrogen atom,
a linear or branched alkyl group having 1-3 carbon atoms, —$CH_2OH$ (in the formula, the hydroxyl group may be protected) or a hydroxyl group that may be protected,
$q_1$ is an integer of 1-7,
when a plurality of $R_{8a}$ units exist, they may be the same or different, when a plurality of $X_{4a}$ units exist, they may be the same or different;
in Formula (IIe),
Ye is a hydrogen atom or an amino-group-protecting group,
Ze is a hydrogen atom or a carboxyl-group-protecting group,
$R_{11a}$-$R_{16a}$ are the same or different and each is a hydrogen atom,
a linear or branched alkyl group having 1-3 carbon atoms, —$CH_2OH$ (in the formula, the hydroxyl group may be protected), or a hydroxyl group that may be protected,
$r_1$ is an integer of 1-10, $r_1'$ is an integer of 1-50,
when a plurality of $R_{11a}$-$R_{16a}$ units exist, they may be the same or different),
but excluding the following compound:

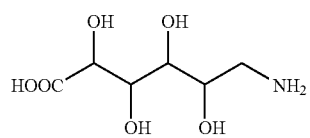

(38) A polymer compound prepared by polymerizing a compound represented by at least one formula selected from the group consisting of Formulas (IIa)-(IIe).
(39) A complex that comprises a solid phase carrier and the compound described in any one of (35)-(38) above.
(40) A complex that comprises the compound described in any one of (35)-(38) above and a molecule A.
(41) A complex that comprises a solid phase carrier, the compound described in any one of (35)-(38) above, and a molecule A.

DETAILED DESCRIPTION OF THE INVENTION

Figure 1:
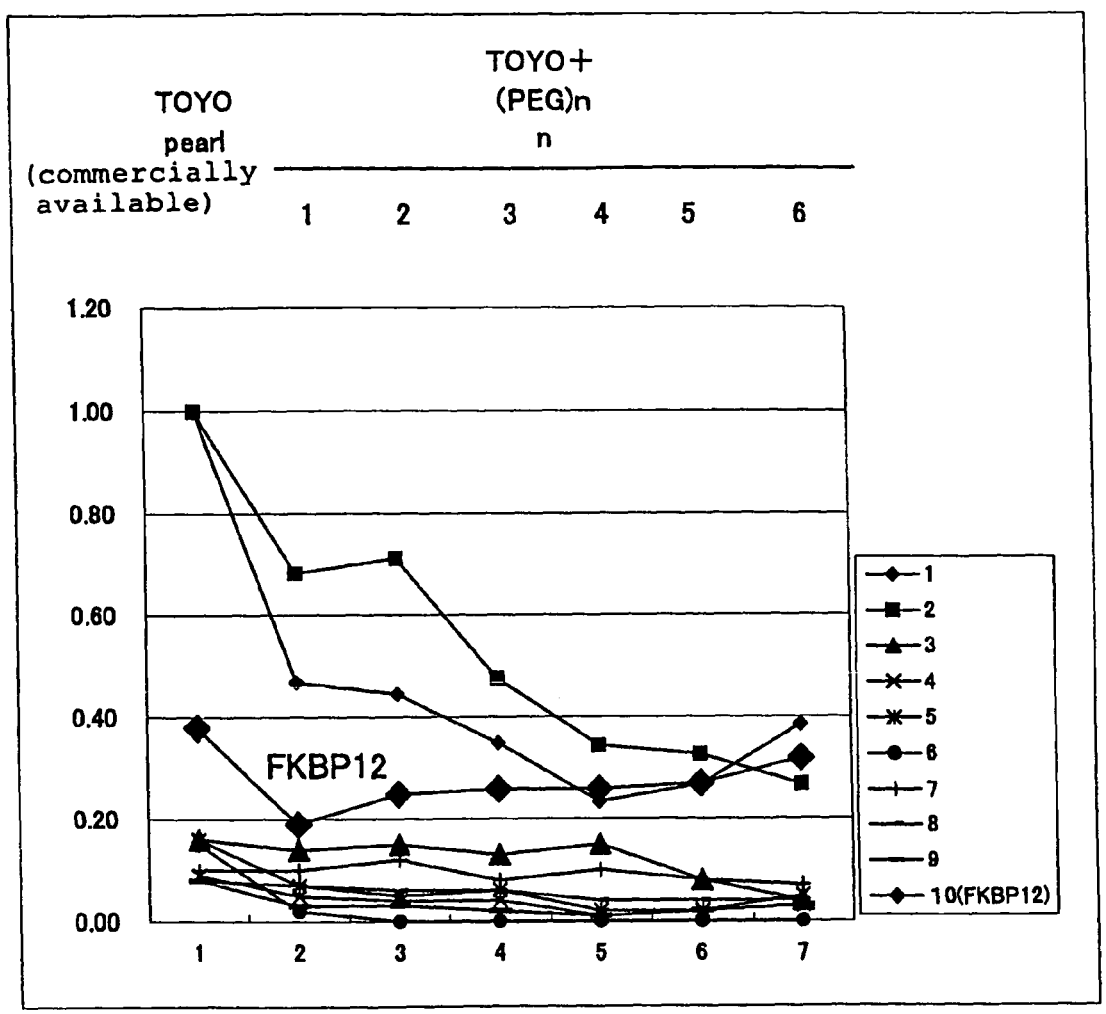
FIG. 1 is a graph showing the effect of introducing a hydrophilic spacer to suppress a nonspecific intermolecular interaction on a solid phase carrier. As the solid phase carrier, a resin was used. Out of molecules adsorbable to a solid phase carrier and/or FK506 on the solid phase carrier, 10 kinds were selected; the effect of introducing a hydrophilic spacer on the amount of each molecule adsorbed is shown. The amount adsorbed of FKBP12, which exhibits a specific interaction with FK506, was nearly constant, irrespective of the introduction of the hydrophilic spacer and the number of repeat units of hexaethylene glycol; particularly, the amounts adsorbed of bands 1 and 2 decreased remarkably, showing that these bands had bound to the FK506-binding affinity resin by a nonspecific interaction, and that this nonspecific interaction could be suppressed by introducing the hydrophilic spacer. The abscissa indicates SDS-PAGE lane number, and the ordinate relatively indicates the band peak amount in SDS-PAGE.

The present invention is based on the finding that nonspecific intermolecular interactions (for example, represented by nonspecific adsorption of a protein to a solid phase carrier), which have been viewed as being problematic in the technology to analyze and utilize a specific intermolecular interaction (described above), are due to the hydrophobic interaction between the solid phase surface in a solid phase carrier and a molecule such as of a protein. Accordingly, the present invention provides a method of regulating the nonspecific adsorption of various molecules to a solid phase by regulating the hydrophobic property of the solid phase surface on the solid phase carrier.

In the present specification, the hydrophobic property can generally be represented by a hydrophobicity parameter, and can, for example, be represented by partition coefficient, specifically by LOGP. In calculating LOGP, CLOGP (a predicted value obtained using a software program for estimating hydrophobicity parameters of a compound by means of a computer; can be calculated using, for example, Corwin/Leo's program (CLOGP, Daylight Chemical Information System Co., Ltd)) and the like are conveniently utilized, but the hydrophobicity parameter is not limited to CLOGP. As the tendency for hydrophobicity increases qualitatively, nonspecific interactions increase. For example, referring to CLOGP, the greater the CLOGP is, the higher the hydrophobicity is; the increase in CLOGP correlates to the increase in a nonspecific interaction (for example, nonspecific adsorption of a protein to a solid phase surface). Here, a change in a hydrophobicity parameter can, for example, be performed by changing the molecule to be immobilized onto the solid phase surface (molecule A) to one having various values (for example, CLOGP) of hydrophobicity parameter, and it is also possible to modify or reduce the hydrophobic property of the solid phase surface by introducing a hydrophilic spacer between the solid phase carrier and the molecule A. On the other hand, by introducing a more hydrophobic spacer, and the like, the hydrophobicity increases and hence the nonspecific interaction increases. That is, "regulation" of the hydrophobic property in the present invention is intended to mean both an increase and reduction thereof.

Introducing the spacer is a preferred embodiment in cases wherein it is necessary to immobilize onto a solid phase a ligand expected to have a high CLOGP value; a case wherein a hydrophilic spacer is used as a means of suppressing a nonspecific interaction is hereinafter described in detail.

The present invention provides a technology to analyze the interaction between a molecule immobilized onto a solid phase carrier (in the present specification, also defined as molecule A, and also referred to as ligand for convenience) and a molecule that exhibits a specific interaction with the molecule described above (in the present specification, also defined as molecule B, and also referred to as target molecule for convenience), and a technology to identify and select the molecule B on the basis of such analysis. In the present specification, the terms ligand and target molecule are intended to mean a combination of members that exhibit a specific intermolecular interaction with each other, and their designations are variable depending on which member of the combination to immobilize as the ligand onto the solid phase and leave the other member as the target molecule, that is, which member to immobilize onto the solid phase. There can be more than one kind of the molecule B that exhibits a specific interaction with the molecule A, and likewise there can be more than one kind of the molecule A that exhibits a specific interaction with the molecule B. In the present specification, the terms molecule A and molecule B have the symbol A or B given for convenience to make it sure that they are mutually different substances. These terms do not refer to particular molecules but are intended to mean individual molecules that exhibit a specific interaction with each other. Also, such a molecule that does not exhibit a specific interaction with the molecule A has the same definition as "a molecule other than the molecule B".

A "specific interaction" is a characteristic action to specifically recognize, and bind to, a particular ligand (a particular target molecule) only; the relation of a specific receptor to an agonist or an antagonist, the relation of an enzyme to a substrate, and, for example, the relation of an FK506-binding protein (target molecule) to FK506 (ligand), the relation of a steroid hormone receptor to a steroid hormone (e.g., dexamethasone and glucocorticoid receptor), the relation of HDAC to the anticancer agent trapoxin, and the like apply to a "specific interaction". On the other hand, a "nonspecific interaction" refers to an action the subjects of binding by which encompass a broad range of molecules and are not limited to particular molecules, and which produces a situation that is variously changeable depending on reaction conditions; in the present invention, this term means an unparticular intermolecular action to bind or adsorb to the molecule A on a solid phase or the solid phase carrier surface. A "nonspecific interaction" is risky in that the binding based on a "specific interaction" is possibly overlooked as it hampers, or is confused with, the binding of the ligand and the target molecule based on a "specific interaction".

In the present invention, "to analyze a specific interaction" is to obtain the extent of the specific interaction between a molecule A and a molecule B as interaction information, which can, for example, be obtained as numerical values of Kd (dissociation rate constant), Ka (binding rate constant) and the like. In the present invention, "selection" is intended to mean determining whether or not the molecule in question exhibits a specific interaction with the molecule A on the basis of the above-described interaction information, and identifying the molecule B.

In the methods of the present invention of suppressing a nonspecific interaction, of analyzing the specific interaction between the molecule A and molecule B, and of selecting the molecule B, a treatment to reduce the hydrophobic property of the solid phase surface on a solid phase carrier is essential. As an example of the treatment, a method of introducing a hydrophilic spacer, at the time of immobilization of the molecule A to the solid phase carrier, therebetween, can be mentioned. By introducing a hydrophilic spacer, the hydrophobic property of the solid phase carrier surface is altered, so that a nonspecific interaction can be suppressed. By using such a means of suppressing a nonspecific interaction, called a hydrophilic spacer, introduced between the solid phase carrier and the molecule A, it is possible to identify and select a molecule that exhibits a specific interaction with the molecule A (target molecule: molecule B), and to accurately measure the interaction therebetween.

The solid phase carrier used in the present invention is not subject to limitation, as long as a specific interaction between the molecule A and the molecule B is produced thereon; one in common use in the art can be utilized, and is appropriately determined according to the methods conducted for the subsequently performed steps for identifying and selecting the molecule B. As examples of the material, resins (polystyrene, methacrylate resin, polyacrylamide and the like), glass, metals (gold, silver, iron, silicone and the like) and the like are used. These solid phases may be of any form, and are appropriately determined according to the kind of the above-described material and the methods conducted for the subsequently performed steps for analyzing the interaction with the molecule B and identifying and selecting the molecule B. For example, plates, beads, thin films, threads, coils and the like can be mentioned; beads consisting of a resin simplify the subsequent operation when packed in a column, and metallic thin films can be preferably used as carriers for BIACORE and the like by surface plasmon resonance. It is also preferable to use a glass plate.

Although the solid phase used in the present invention, as described above, is not subject to limitation as to the material and form thereof, one having a structural hindrance such that the molecule A is not immobilizable thereon or the molecule A is immobilizable thereon but cannot exhibit a specific interaction with the molecule B, of course, is undesirable for embodying the present invention because it complicates the operation due to the necessity of an additional step or is unusable in some cases.

In the present invention, "hydrophilic spacer" refers to a substance that is introduced to become a group that interlies between a solid phase carrier and the molecule A at the time of immobilization of the molecule A onto the solid phase carrier, and is hydrophilic. Degrees of hydrophilicity are described below. Here, "a spacer interlies" means that the spacer is present between a functional group in the solid phase and a functional group in the ligand. The spacer binds to the functional group in the solid phase at one end and binds to the functional group in the ligand at the other end.

Also, the hydrophilic spacer may be one obtained by sequentially binding and polymerizing 2 or more compounds, as long as it is capable of eventually functioning as a group that interlies between the solid phase carrier and the molecule A. Preferably, the hydrophilic spacer is obtained by a polymerization reaction of a unit compound. The process to bind or polymerize 2 or more compounds is preferably conducted on a solid phase. Binding of the solid phase carrier and the hydrophilic spacer, binding of the hydrophilic spacer and the molecule A, and binding and polymerization of individual components that constitute the hydrophilic spacer are based on a covalent bond or a non-covalent bond, such as an amide bond, a Schiff base, a C—C bond, an ester bond, a hydrogen bond or a hydrophobic interaction, all of which are formed using materials and reactions known in the art.

In the present invention, the hydrophilic spacer introduced between a solid phase carrier and a molecule A as a means of suppressing a nonspecific interaction is not subject to limitation, as long as it alters the hydrophobic property of the solid phase surface in the solid phase carrier to eliminate or suppress the nonspecific interaction, and is preferably a compound having the number of hydrogen bond acceptor (HBA; hydrogen bond acceptor) of 6 or more, or the number of hydrogen bond donor (HBD; hydrogen bond donor) of 5 or more, or the total number of HBA and HBD per spacer molecule of 9 or more while in a state bound to the solid phase carrier and the molecule A (a hydrophilic spacer in this state is hereinafter referred to as "hydrophilic spacer portion" for convenience). Also, the hydrophilic spacer may be a compound that meets two or all of these conditions. Particularly preferably, the number of HBA is 9 or more and the number of HBD is 6 or more.

Here, the number of hydrogen bond acceptor number (the number of HBA) is the total number of nitrogen atoms (N) and oxygen atoms (O) contained, and the number of hydrogen bond donor (the number of HBD) is the total number of NH and OH contained (C. A. Lipinski et al., Advanced Drug Delivery Reviews 23(1997) 3-25). In the present invention, even if it interlies between a solid phase carrier and a molecule A, NH or OH derived from the solid phase carrier (that is, one that has already been introduced at the time of solid phase synthesis and is hence regarded as part of the solid phase carrier) is not included in the number of HBA or the number of HBD, respectively. Also, to make the binding of the molecule A and the hydrophilic spacer more easier, an optionally chosen group, between the molecule A and the hydrophilic spacer, can be bound or introduced to the molecule A in advance before it is bound to the hydrophilic spacer; however, because these are appropriately chosen according to the molecule A, and are considered to make a little contribution to the modification of the hydrophobic property of the solid phase carrier, the N and O or NH and OH contained in the group are also not included in the number of HBD or the number of HBA in the present invention. Note that introduction of an optionally chosen group between the molecule A and the hydrophilic spacer also utilizes various covalent bonds or non-covalent bonds as described above, and is performed using materials and reactions known in the art.

Under the circumstances of the invention of the present application, nonspecific interactions cannot fully be suppressed so that nonspecific adsorption to the solid phase carrier occurs, unless at least one, preferably 2 or more, of the conditions of an the number of HBA of 6 or more (preferably 9 or more), an the number of HBD of 5 or more (preferably 6 or more), and the total number of HBA and HBD of 9 or more, are met. Therefore, in the hydrophilic spacer of the invention of the present application, "hydrophilic" means that the above-described requirements are met. In the present invention, the upper limit of the number of HBD or the number of HBA in the hydrophilic spacer is not subject to limitation, as long as the spacer is hydrophilic and capable of suppressing a nonspecific interaction; by appropriately repeating a polymerization reaction and the like, a spacer having an extremely high hydrophilicity can be obtained. Also, the spacer may be a large substance such as a protein; from this viewpoint, the upper limit should be at a value of 50,000 or so in all cases.

Also, in the present invention, a hydrophilic spacer having as the basic skeleton thereof a compound that meets the above-described definition for the degree of "hydrophilicity" but is physically or chemically unstable, for example, a sugar derivative or a Sepharose derivative, is undesirable for use in some cases because it does not endure ligand immobilization and various subsequent treatments due to the instability thereof.

Furthermore, the hydrophilic spacer used in the present invention is preferably one that does not exhibit a nonspecific interaction (for example, protein adsorption to the spacer and the like) per se. Specifically, it is preferable that the spacer does not have a functional group that becomes positively or negatively charged in an aqueous solution; as the functional group, an amino group (but excluding cases wherein a functional group that attenuates the basicity of the amino group (for example, a carbonyl group, a sulfonyl group) is bound to the amino group), a carboxyl group, a sulfuric acid group, a nitric acid group, a hydroxamic acid group and the like can be mentioned. Here, "in an aqueous solution" specifically refers to an environment wherein the process to analyze the interaction between a molecule A and a molecule B on a solid phase, the process to select the molecule B, or a binding reaction (a reaction based on a specific interaction) of the molecule A and the molecule B performed to screen for the molecule B is conducted, and whereunder the hydrophilic spacer ionizes when having a functional group that becomes positively or negatively charged. Such conditions are, for example, in an aqueous solution, pH 1-11, temperature 0° C.-100° C., preferably pH nearly neutral (pH 6-8), about 4° C. to about 40° C. or so.

Furthermore, the hydrophilic spacer of the present invention preferably has 1 or more carbonyl groups in the molecule thereof, as understood from the various structures or compounds described below as preferable examples of the hydrophilic spacer.

For example, the hydrophilic spacer of the present invention is a compound that has at least one partial structure represented by any one formula selected from the group consisting of Formulas (Ia)-(Ie) below.

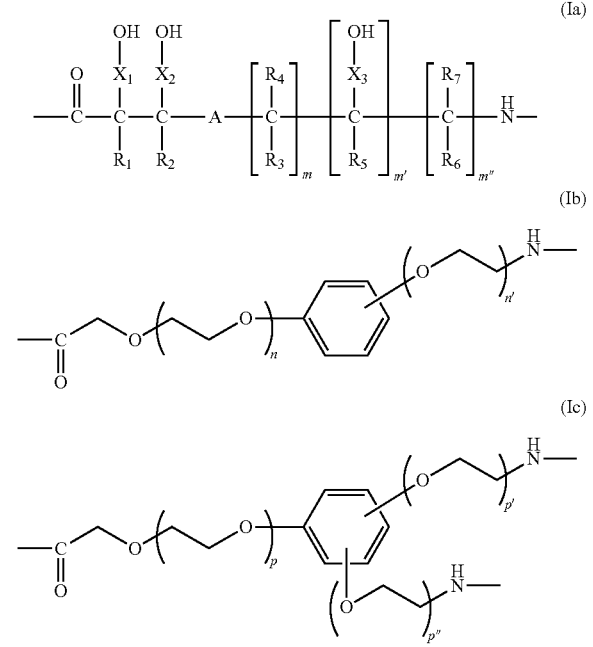

(In Formula (Ia),

A is an appropriate joining group, $X_1$-$X_3$ are the same or different and each is a single bond or a methylene group that may be substituted by a linear or branched alkyl group having 1-3 carbon atoms, $R_1$-$R_7$ are the same or different and each is a hydrogen atom, a linear or branched alkyl group having 1-3 carbon atoms, —$CH_2OH$ or a hydroxyl group, m is an integer of 0-2, m' is an integer of 0-10, m" is an integer of 0-2, when a plurality of $R_3$-$R_7$ units exist, they may be the same or different, when a plurality of $X_3$ units exist, they may be the same or different;

in Formula (Ib), n and n' are the same or different and each is an integer of 1-1000;

in Formula (Ic), p, p' and p" are the same or different and each is an integer of 1-1000;

in Formula (Id), $X_4$ is a single bond or a methylene group that may be substituted by a linear or branched alkyl group having 1-3 carbon atoms, $R_8$-$R_{10}$ are the same or different and each is a hydrogen atom, a linear or branched alkyl group having 1-3 carbon atoms, —$CH_2OH$ or a hydroxyl group, q is an integer of 1-7, when a plurality of $R_8$ units exist, they may be the same or different, when a plurality of $X_4$ units exist, they may be the same or different;

in Formula (Ie), $R_{11}$-$R_{16}$ are the same or different and each is a hydrogen atom, a linear or branched alkyl group having 1-3 carbon atoms, —$CH_2OH$ or a hydroxyl group, r is an integer of 1-10, r' is an integer of 1-50, when a plurality of $R_{11}$-$R_{16}$ units exist, they may be the same or different).

In the present specification, referring to the definitions for individual groups, the "appropriate joining group" is not subject to limitation, as long as it is capable of joining mutually adjoining sites, and specifically the following groups are used.

-continued

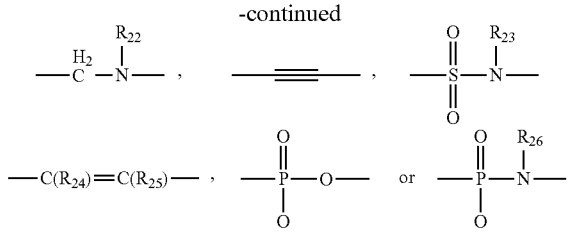

(in the formulas, $R_{17}$ is a hydrogen atom or a linear or branched alkyl group having 1-3 carbon atoms, $R_{18}$-$R_{21}$ are the same or different and each is a hydrogen atom, a linear or branched alkyl group having 1-3 carbon atoms, —$CH_2OH$ or a hydroxyl group, $R_{22}$-$R_{26}$ are the same or different and each is a hydrogen atom or a linear or branched alkyl group having 1-3 carbon atoms (the alkyl group may be substituted by a hydrophilic substituent such as a hydroxyl group, a carboxylic acid group, or an amino group))

In the present specification, referring to the definitions for individual groups, as examples of the "linear or branched alkyl group having 1-3 carbon atoms", a methyl group, an ethyl group, a propyl group, an isopropyl group and the like can be mentioned.

In the present specification, "a methylene group that may be substituted by a linear or branched alkyl group having 1-3 carbon atoms" is intended to mean an unsubstituted methylene group and a methylene group substituted by 1 or 2 of the above-described linear or branched alkyl groups having 1-3 carbon atoms.

In Formula (Ia), the joining group A is preferably a group represented by the formula:

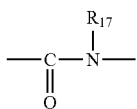

($R_{17}$ is preferably a hydrogen atom)

each of $X_1$-$X_3$ is preferably a single bond, each of $R_1$-$R_7$ is preferably a hydrogen atom, m is preferably an integer of 0-2, m' is preferably an integer of 0-2, and m" is preferably an integer of 0-2.

In Formula (Ib), each of n and n' is preferably independently an integer of 1-50, more preferably independently an integer of 1-5, particularly preferably equally an integer of 1-5, and still more preferably equally 5.

In Formula (Ic), each of p, p', and p" is preferably independently an integer of 1-50, more preferably independently an integer of 1-5, particularly preferably equally an integer of 1-5, and still more preferably equally 5.

In Formula (Id), $X_4$ is preferably a single bond, each of $R_8$-$R_{10}$ is preferably a hydrogen atom, and q is preferably an integer of 1-4, particularly preferably 4.

In Formula (Ie), each of $R_{11}$-$R_{16}$ is preferably a hydrogen atom, r is preferably 1, and r' is preferably an integer of 1-50, more preferably an integer of 1-5, and particularly preferably 5.

The hydrophilic spacer of the present invention may have two or more of the above-described partial structure; in that case, the partial structures may be represented by the same formula or represented by different formulas.

At least one kind of the above-described hydrophilic spacer is immobilized onto a solid phase carrier. The number of spacers on the solid phase carrier is not subject to limitation, and can be appropriately determined by those skilled in the art according to the kind and amount of the molecule A, the kind and amount of the molecule B, and the kind and characteristic of the spacer used, and needs not be determined, provided that the desired intermolecular interaction can be detected. Usually, the hydrophilic spacer is immobilized using an excess amount thereof relative to the solid phase and the molecule A. The hydrophilic spacers that have not bound to the solid phase carrier can easily be removed from the reaction system by a treatment such as washing the solid phase carrier.

In the present invention, the molecule A (ligand) to be immobilized onto a solid phase carrier is not subject to limitation, and may be a known compound or a novel compound that will be developed in the future. Also, the molecule A (ligand) may be a small compound or a large compound. Here, a small compound refers to a compound having a molecular weight of 1000 or less or so; for example, an organic compound commonly usable as a pharmaceutical, a derivative thereof, and an inorganic compound can be mentioned; specifically, a compound produced by making use of a method of organic synthesis and the like, a derivative thereof, a naturally occurring compound, a derivative thereof, a small nucleic acid molecule such as a promoter, various metals, and the like can be mentioned; and desirably, an organic compound that can be used as a pharmaceutical, a derivative thereof, or a nucleic acid molecule can be referred to. Also, as the large compound, a compound having a molecular weight of 1000 or more or so, which is a protein, a polynucleic acid, a polysaccharide, or a combination thereof, and the like can be mentioned, and a protein is desirable. These small compounds or large compounds are commercially available if they are known compounds, or can be obtained via steps such as of collection, production and purification according to various publications. These may be of natural origin, or may be prepared by gene engineering, or may be obtained by semi-synthesis and the like.

In the present invention, a process to select a molecule B on the basis of the specific interaction with the above-described molecule A on a solid phase having the molecule A immobilized thereon is necessary. Therefore, the molecule B is not subject to limitation, as long as it specifically interacts with the molecule A, and is expected to be a known compound in some cases or a novel substance in other cases. The molecule B may be a small compound or a large compound. When the molecule B is a small compound, the molecule B can be selected on the basis of the specific interaction with the molecule A that is a small compound, which is a small compound-small compound interaction, or on the basis of the specific interaction with the molecule A that is a large compound, which is a large compound-small compound interaction. Also, when the molecule B is a large compound, the molecule B can be selected on the basis of the specific interaction with the molecule A that is a small compound, which is a small compound-large compound interaction, or on the basis of the specific interaction with the molecule A that is a large compound, which is a large compound-large compound interaction. A preferable combination of the molecule A and the molecule B is the combination of a small compound and a large compound, or the combination of a large compound and a large compound.

Analysis of the interaction of the molecule A with the molecule B and selection of the molecule B are conveniently conducted on a solid phase. When a candidate substance is anticipated as the molecule B, it is possible to bring the candidate substance alone into contact with the molecule A immobilized on the above-described solid phase, measure the interaction therebetween, and determine whether or not the candidate substance is the molecule B, that is, whether or not the candidate substance is a target molecule for the molecule A; usually, by bringing a sample that contains a plurality of substances (a large compound and/or a small compound) into contact with the molecule A, and measuring the presence or absence of an interaction between each of the plurality of substances (the large compound and/or the small compound) and the molecule A and the extent of the interaction, whether or not the candidate substance is the molecule B is determined and the molecule B is selected. Here, the sample that contains a plurality of substances may consist essentially of known compounds, may contain some novel compounds, and may consist essentially of novel compounds. However, according to search of target molecules for ligands, or recent advances in proteome analysis, it is desirable that the sample be a mixture essentially of compounds of known structures. As the sample consisting essentially of known compounds, a mixture of proteins prepared by gene engineering using *Escherichia coli* and the like, and the like can be mentioned; as the sample that contains some novel compounds, a cell or tissue extract (Lysate) can be mentioned; as the sample that consists essentially of novel compounds, a mixture of novel proteins whose functions and structures are yet unknown, or newly synthesized compounds and the like, can be mentioned. When the sample is a mixture, especially when it contains known compounds, the contents of these compounds in the sample may optionally be set at desired levels in advance. From the viewpoint of searching a target molecule for a ligand, the molecule B to be selected is preferably a small compound or a large compound, and for searching a target molecule in the body of an animal such as a human, the molecule B is preferably a large compound.

The present invention provides a method of screening for a molecule B that exhibits a specific interaction with a molecule A immobilized on the above-described solid phase using the molecule A. The screening method includes at least the following steps. Note that the respective definitions for the molecule A, the molecule B, the solid phase carrier, and the hydrophilic spacer in this screening method are as described above.

(1) A step of immobilizing the molecule A onto a solid phase carrier via a hydrophilic spacer.

This step comprises binding the molecule A and the hydrophilic spacer and binding the hydrophilic spacer and the solid phase carrier. It is possible to bind the hydrophilic spacer to the molecule A and then bind the complex thereof to the solid phase carrier, and also possible to bind the molecule A after the hydrophilic spacer is bound to the solid phase carrier; whether or not the molecule A has been immobilized onto the solid phase carrier can be confirmed by utilizing a color developing reaction based on a particular structure or substituent and the like contained in the molecule A or an optionally chosen group that has been bound and introduced to the molecule A in advance, and the like. For example, the ninhydrin reaction, which recognizes an amino group, and the like can be utilized. Each binding is performed by utilizing a reaction in common use in the art. As a convenient and accurate means, a method utilizing an amide bond formation reaction can be mentioned. This reaction can, for example, be performed according to "Peputido Gousei no Kiso to Jikken" (ISBN 4-621-02962-2, Maruzen, first edition issued in 1985). Regarding the reagents and solvents used in each reaction, those in common use in the relevant field can be utilized, and are appropriately selected according to the binding reaction employed.

(2) A step of contacting a sample that contains or does not contain the molecule B with the solid phase carrier with the molecule A immobilized thereon obtained in (1) above.

The sample used in this step is one containing a plurality of substances as described above. The mode of embodiment thereof is not subject to limitation, and can be appropriately changed according to the solid phase carrier used and what principles, means and methods to use for the identification or analysis in the subsequent steps (3) and (4). For example, when using a column packed with a bead resin with the molecule A immobilized thereon, it is preferable that the sample be liquid. In the case of a sample that does not contain the molecule B, identification and analysis of a molecule (a plurality of kinds present in some cases) that has not exhibited a specific interaction with the molecule A in step (3) are conducted. In the case of a sample that contains the molecule B, the molecule B (a plurality of kinds present in some cases) that has exhibited a specific interaction with the molecule A in step (3) is identified and analyzed. The method of bringing the sample and the solid phase carrier into contact with each other is not subject to limitation, as long as the molecule B in the sample can bind to the molecule A immobilized on the solid phase carrier, and can be appropriately changed according to on the solid phase carrier used and what principles, means and methods to use for the identification or analysis in the subsequent steps (3) and (4). For example, when using a column packed with a bead resin with the molecule A immobilized thereon, this method is conveniently performed by adding the liquefied sample to the column, and passing it through the column.

(3) A step of identifying and analyzing a molecule that has exhibited or has not exhibited a specific interaction with the molecule A.

Although this step can be appropriately changed according to the kinds of the solid phase carrier used and the molecule A immobilized, and the like, it is conducted by various methods in common use in the art to identify a small compound or a large compound. Also, the step can also be performed by a method that will be developed in the future. For example, when using a column packed with a bead resin having the molecule A immobilized thereon as the molecule A-immobilized solid phase carrier [step (1)], the molecule B is bound to the molecule A by the subsequent addition of the sample [step (2)]. It is also possible to dissociate the molecule B bound from the molecule A by a treatment such as altering the polarity of the buffer solution or further adding the molecule A in excess, and then identify the molecule B, or to extract the molecule B with a surfactant and the like while remaining in a state bound to the molecule A on the solid phase, and then identify the molecule B. As the method of identification, specifically, known techniques such as electrophoresis, immunoblotting and immunoprecipitation, which employ immunological reactions, chromatography, mass spectrometry, amino acid sequencing, and NMR (especially for small-molecules), or combinations of these methods can be used. Although the step of identifying a molecule that does not bind to the molecule A can also be conducted in accordance with the above-described method of identifying a molecule that binds to the molecule A, it is preferable that a treatment such as concentration or crude purification be conducted in advance before entering the identification step, since a molecule contained in the effluent from the column is the subject of identification. On the basis of the data obtained and existing reports, each molecule is identified, and whether or not it is a target molecule for the molecule A is determined.

Also, this step may be automated. For example, it is also possible to directly read data on various molecules obtained by two-dimensional electrophoresis, and identify the molecules on the basis of existing databases.

The present invention further provides a compound suitable as the above-described hydrophilic spacer, a complex of the compound and a solid phase carrier, a complex of the compound and a molecule A, and a complex of the compound, a solid phase carrier and a molecule A. As the compound, compound represented by General Formulas (IIa)-(IIe) below (hereinafter also referred to as the monomer components of the present invention) and polymers thereof (hereinafter also referred to as the polymers or polymer compounds of the present invention) can be mentioned.

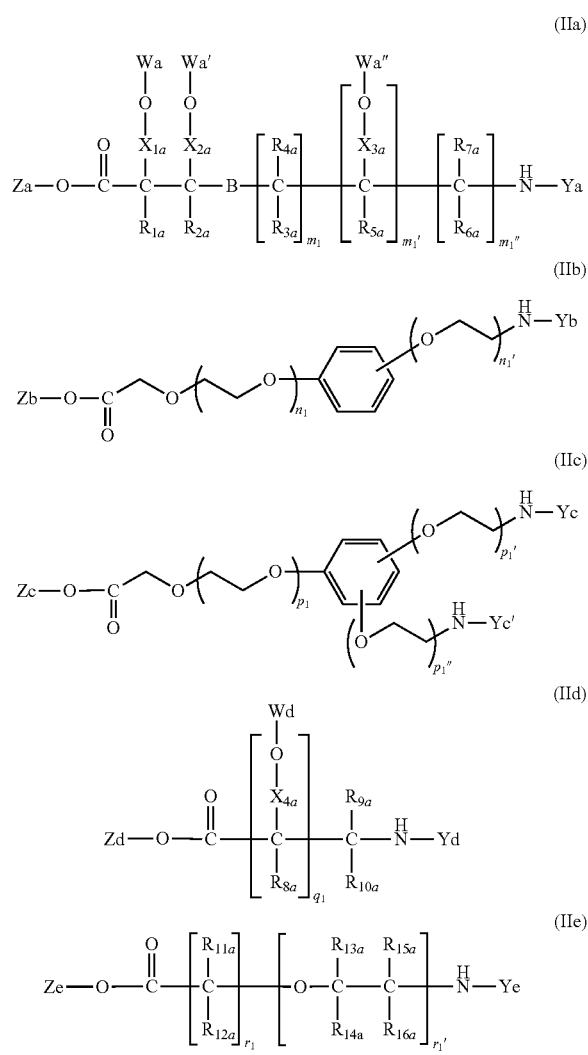

(In Formula (IIa),
Ya is a hydrogen atom or an amino-group-protecting group,
Za is a hydrogen atom or a carboxyl-group-protecting group,
Wa, Wa' and Wa" are the same or different and each is a hydrogen atom or a hydroxyl-group-protecting group (these protective groups may bind together with mutually adjoining protective groups to form a dialkylmethylene group),
B is an appropriate joining group,
$X_{1a}$-$X_{3a}$ are the same or different and each is a single bond or a methylene group that may be substituted by a linear or branched alkyl group having 1-3 carbon atoms, $R_{1a}$-$R_{7a}$ are the same or different and each is a hydrogen atom, a linear or branched alkyl group having 1-3 carbon atoms, —$CH_2OH$ (in the formula, the hydroxyl group may be protected) or a hydroxyl group that may be protected,
$m_1$ is an integer of 0-2, $m_1'$ is an integer of 0-10, $m_1''$ is an integer of 0-2,
when a plurality of $R_{3a}$-$R_{7a}$ units exist, they may be the same or different, when a plurality of $X_{3a}$ units exist, they may be the same or different;
in Formula (IIb),
Yb is a hydrogen atom or an amino-group-protecting group,
Zb is a hydrogen atom or a carboxyl-group-protecting group,
$n_1$ and $n_1'$ are the same or different and each is an integer of 1-1000;
in Formula (IIc),
Yc and Yc' are the same or different and each is a hydrogen atom or an amino-group-protecting group,
Zc is a hydrogen atom or a carboxyl-group-protecting group,
$p_1$, $p_1'$ and $p_1''$ are the same or different and each is an integer of 1-1000;
in Formula (IId),
Yd is a hydrogen atom or an amino-group-protecting group,
Zd is a hydrogen atom or a carboxyl-group-protecting group,
Wd is a hydrogen atom or a hydroxyl group-protecting group,
$X_{4a}$ is a single bond or a methylene group that may be substituted by a linear or branched alkyl group having 1-3 carbon atoms,
$R_{8a}$-$R_{10a}$ are the same or different and each is a hydrogen atom,
a linear or branched alkyl group having 1-3 carbon atoms, —$CH_2OH$ (in the formula, the hydroxyl group may be protected) or a hydroxyl group that may be protected,
$q_1$ is an integer of 1-7,
when a plurality of $R_{8a}$ units exist, they may be the same or different, when a plurality of $X_{4a}$ units exist, they may be the same or different;
in Formula (IIe),
Ye is a hydrogen atom or an amino-group-protecting group,
Ze is a hydrogen atom or a carboxyl-group-protecting group,
$R_{11a}$-$R_{16a}$ are the same or different and each is a hydrogen atom,
a linear or branched alkyl group having 1-3 carbon atoms, —$CH_2OH$ (in the formula, the hydroxyl group may be protected) or a hydroxyl group that may be protected,
$r_1$ is an integer of 1-10, $r_1'$ is an integer of 1-50,
when a plurality of $R_{11a}$-$R_{16a}$ units exist, they may be the same or different).

Referring to the definitions for groups in individual formulas, what are meant by "an appropriate joining group", "a linear or branched alkyl group having 1-3 carbon atoms" and "a methylene group that may be substituted by a linear or branched alkyl group having 1-3 carbon atoms" are as described above.

In Formula (IIa), the joining group B is preferably a group represented by the formula:

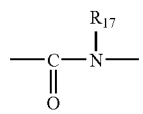

($R_{17}$ is preferably a hydrogen atom)
each of $X_{1a}$-$X_{3a}$ is preferably a single bond, each of $R_{1a}$-$R_{7a}$ is preferably a hydrogen atom, $m_1$ is preferably an integer of 0-2, $m_1'$ is preferably an integer of 0-2, and $m_1''$ is preferably an integer of 0-2.

In Formula (IIb), each of $n_1$ and $n_1'$ is independently an integer of 1-50, more preferably independently an integer of 1-5, particularly preferably equally an integer of 1-5, and still more preferably equally 5.

In Formula (IIc), each of $p_1$, $p_1'$ and $p_1''$ is independently an integer of 1-50, more preferably independently an integer of 1-5, particularly preferably equally an integer of 1-5, and still more preferably equally 5.

In Formula (IId), $X_{4a}$ is independently a single bond, each of $R_{8a}$-$R_{10a}$ is independently a hydrogen atom, and $q_1$ is preferably an integer of 1-4, particularly preferably 4.

In Formula (IIe), each of $R_{11a}$-$R_{16a}$ is preferably a hydrogen atom, $r_1$ is preferably 1, $r_1'$ is preferably an integer of 1-50, more preferably an integer of 1-5, and particularly preferably 5.

Referring to the definitions for groups in individual formulas, as "an amino-group-protecting group", "a carboxyl-group-protecting group" or "a hydroxyl-group-protecting group", one suitable for the conduct of various polymerization reactions and subsequent binding with a ligand and the like is selected. As examples of the "amino-group-protecting group", lower alkoxycarbonyl groups such as a tert-butoxycarbonyl group and a methoxycarbonyl group; aralkyloxycarbonyl groups such as a benzyloxycarbonyl group; aralkyl groups such as a benzyl group; substituted sulfonyl groups such as a benzenesulfonyl group, a p-toluenesulfonyl group and a methanesulfonyl group, and the like can be mentioned. As examples of the "carboxyl-group-protecting group", linear or branched lower alkyl groups having 1-6 carbon atoms, such as a methyl group, an ethyl group, a propyl group, a butyl group and an isobutyl group; aralkyl groups such as a benzyl group, and the like can be mentioned. As examples of the "hydroxyl-group-protecting group", acyl groups such as an acetyl group, a propionyl group, a pivaloyl group and a benzoyl group; alkoxycarbonyl groups such as a methoxycarbonyl group and a tert-butoxycarbonyl group; aralkyloxycarbonyl groups such as a benzyloxycarbonyl group; arylmethyl groups such as a benzyl group and a naphthylmethyl group; silyl groups such as a trimethylsilyl group, a triethylsilyl group, a benzyldimethylsilyl group and a tert-butyldiphenylsilyl group; lower alkoxymethyl groups such as an ethoxymethyl group and a methoxymethyl group, and the like can be mentioned. As an example of a listing of appropriate protective groups, a commonly known publication "Protective Groups in Organic Synthesis, T. W. Green and P. G. M. Wuts. (John Wiley & Sons, Inc.)" can be mentioned.

When a plurality of "amino-group-protecting groups", "carboxyl-group-protecting groups" and/or "hydroxyl-group-protecting groups" are present in the compound, they may be identical to each other, and are appropriately selected according to the site that needs to be protected. The definitions for the other individual symbols are as described above.

Note that the following compound is a compound having a CAS number but the utility thereof as a hydrophilic spacer for reducing the hydrophobic property of the solid phase surface in a solid phase carrier is not known at all.

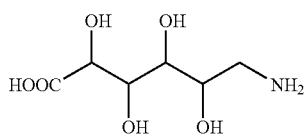

CAS No. 2526-81-3

A general method of producing the monomer component of the present invention or a derivative thereof is described below, but it is obvious to those skilled in the art that the same can also be produced by other methods in common use in the art or combinations thereof.

Note that the abbreviations used in the present specification are as follows.

| Abbreviation | Formal designation |
|---|---|
| Ac | Acetyl group |
| AET | Aminoethyltartaric diamide |
| AMT | Aminomethyltartaric diamide |
| Bn | Benzyl group |
| $Bu_3P$ | Tributylphosphine |
| CDI | 1,1'-Carbonyldiimidazole |
| DABT | Dihydroxyaminobutyltartaric acid |
| DBU | 1,8-Diazabicyclo[5.4.0]undeca-7-ene |
| DMAP | Dimethylaminopyridine |
| DME | 1,2-Dimethoxyethane |
| DMF | Dimethylformamide |
| EDC | 1-[3-(Dimethylamino)propyl]-3-ethylcarbodiimide |
| Et | Ethyl group |
| Fmoc | 9-Fluorenylmethyloxycarbonyl group |
| Fmoc-OSu | 9-Fluorenylmethylsuccinimidylcarbonate |
| Gold foil | Gold foil |
| HOBt | 1-Hydroxybenzotriazole |
| HyT | Hydrazinotartaric amide |
| Me | Methyl group |
| NMP | N-methyl-2-pyrrolidone |
| PEG | Polyethylene glycol |
| $Ph_3P$ | Triphenylphosphine |
| PyBOP | Benzotriazol-1-yl-oxy-tris-pyrolidino-phosphonium hexafluorophosphate |
| TBAF | Tetrabutylammonium fluoride |
| TBDMS | t-Butyldimethylsilyl group |
| TBDMSOTf | Trifluoromethanesulfonic acid t-butyldimethylsilyl group |
| TBDPS | t-Butyldiphenylsilyl group |
| TBS | t-Butyldimethylsilyl group |
| tBu | t-Butyl group |
| TFA | Trifluoroacetic acid |
| THF | Tetrahydrofuran |
| TMAD | N,N,N',N'-tetramethylazodicarboxamide |
| TOYO-Pearl resin | TOYO-Pearl resin |
| Tr | Trityl group |
| Ts | Tosyl group (toluenesulfonyl group) |
| WSC | Water-soluble carbodiimide (N-ethyl-N'-(3'-dimethylaminopropyl)carbodiimide) |

Process 1: Production Method (1) for General Formula (IIa)
($m_1=1$, $m_1'=2$, $m_1''=1$)

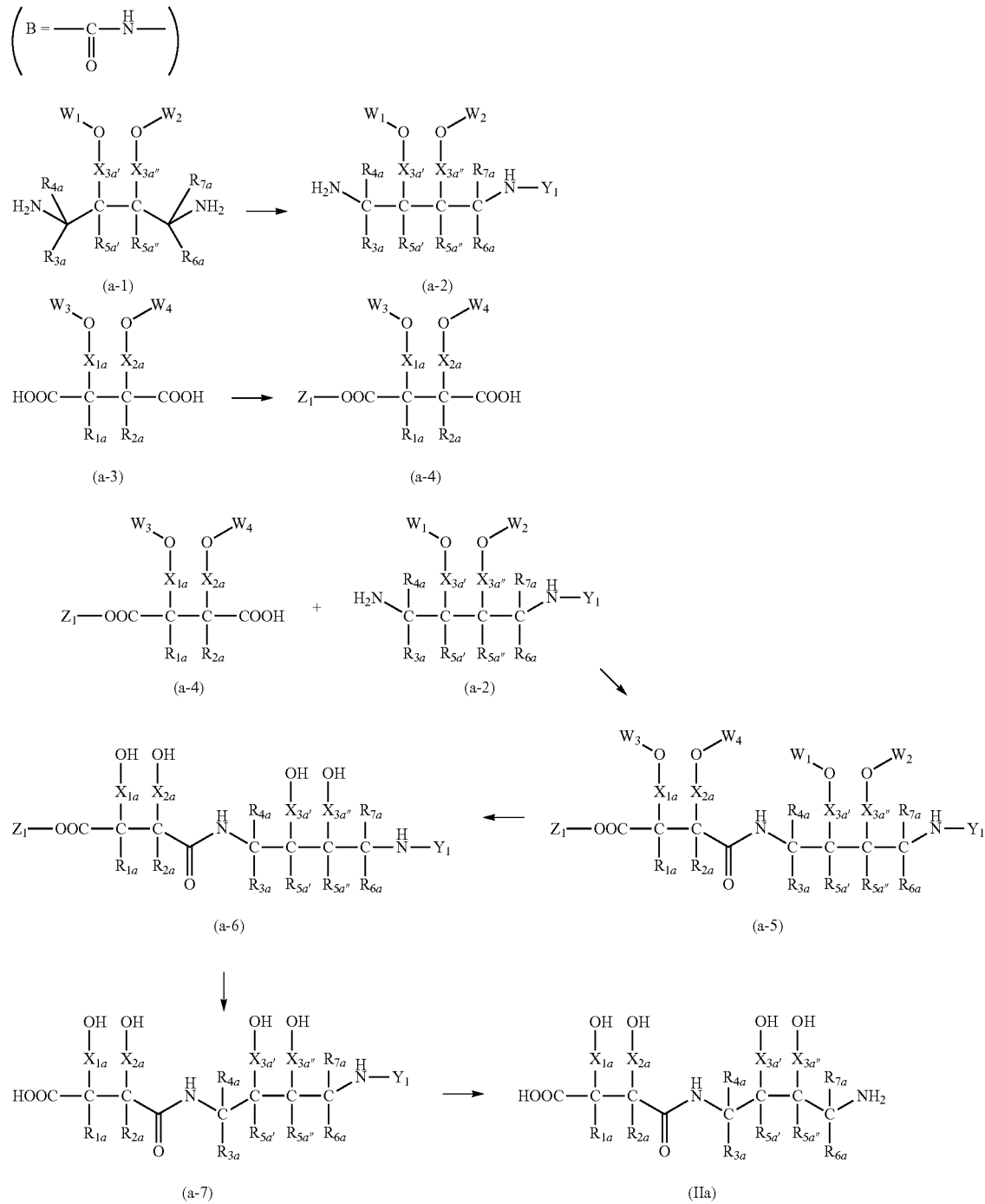

In the formulas, $W_1$-$W_4$ are hydroxyl-group-protecting groups, $Z_1$ is a carboxyl-group-protecting group, and $Y_1$ is an amino-group-protecting group. $X_{3a'}$ has the same definition as $X_{3a}$ and $X_{3a''}$ has the same definition as $X_{3a}$. $R_{5a'}$ has the same definition as $R_{5a}$ and $R_{5a''}$ has the same definition as $R_{5a}$. Also, the definitions for the other individual symbols are as described above.

As the hydroxyl-group-protecting group, an optionally chosen group in common use in the art is used; specifically, alkyl groups such as a tert-butyl group; acyl groups such as an acetyl group, a propionyl group, a pivaloyl group and a benzoyl group; alkoxycarbonyl groups such as a methoxycarbonyl group and a tert-butoxycarbonyl group; aralkyloxycarbonyl groups such as a benzyloxycarbonyl group; arylmethyl groups such as a benzyl group and a naphthylmethyl group; silyl groups such as a trimethylsilyl group, a triethylsilyl group, a tert-butyldimethylsilyl group and a tert-butyldiphenylsilyl group; lower alkoxymethyl groups such as an ethoxymethyl group and a methoxymethyl group, and the like can be mentioned as examples, and preferably, a tert-butyldimethylsilyl group, a tert-butyldiphenylsilyl group, a methoxymethyl group and a tert-butyl group can be mentioned. As the carboxyl-group-protecting group, an optionally chosen group in common use in the art is used; specifically, linear or branched lower alkyl groups having 1-6 carbon atoms, such as a methyl group, an ethyl group, a propyl group, a t-butyl group, an isobutyl group and an allyl group; aralkyl groups such as a benzyl group; silyl groups such as a tert-butyldimethylsilyl group and a tert-butyldiphenylsilyl group, and the like can be mentioned as examples; preferably, an allyl group, a tert-butyl group, a benzyl group and a tert-a butyldiphenylsilyl group can be mentioned. As the amino-group-protecting group, an optionally chosen group in common use in the art is used; specifically, lower alkoxycarbonyl groups such as a tert-butoxycarbonyl group and a methoxycarbonyl group; aralkyloxycarbonyl groups such as a benzyloxycarbonyl group; aralkyl groups such as a benzyl group; substituted sulfonyl groups such as a benzenesulfonyl group, a p-toluenesulfonyl group and a methanesulfonyl group, and the like can be mentioned as examples, preferably, a tert-butoxycarbonyl group and a benzyloxycarbonyl group can be mentioned.

Amino group protection and deprotection, carboxyl group protection and deprotection, and hydroxyl group deprotection are appropriately performed using known methods and reagents according to the protective group used.

The reaction to dehydration-condense Compound (a-4) and Compound (a-2) by amidation is normally conducted by reacting these compounds in the presence of an equivalent of the amino compound and the carboxylic acid, using 1.1 equivalents or so of a condensing agent such as N-ethyl-N'-dimethylaminocarbodiimide or N-hydroxy-benzotriazol, in a solvent such as DMF or methylene chloride at room temperature for 1 hour to 10 hours or so.

Process 2: Production Method (2) for General Formula (IIa) ($m_1=2$, $m_1'=0$, $m_1''=2$)

In the formulas, $Y_2$ is an amino-group-protecting group. $R_{3a'}$ has the same definition as $R_{3a}$ and $R_{3a''}$ has the same definition as $R_{3a}$. $R_{4a'}$ has the same definition as $R_{4a}$ and $R_{4a''}$ has the same definition as $R_{4a}$. $R_{6a'}$ has the same definition as $R_{6a}$ and $R_{6a''}$ has the same definition as $R_{6a}$. $R_{7a'}$ has the same definition as $R_{7a}$ and $R_{7a''}$ has the same definition as $R_{7a}$. The definitions for the other individual symbols are as described above. As examples of the amino-group-protecting group, the same as those described above can be mentioned.

Amino group deprotection is appropriately performed using known methods and reagents according to the protective group used.

The reaction to dehydration-condense Compound (a-9) and Compound (a-10) by amidation is normally conducted by reacting these compounds in the presence of an equivalent of the amino compound and the carboxylic acid, using 1.1 equivalents or so of a condensing agent such as N-ethyl-N'-dimethylaminocarbodiimide or N-hydroxy-benzotriazol, in a solvent such as DMF or methylene chloride at room temperature for 1 hour to 10 hours or so.

Process 3: Production Method (3) for General Formula (IIa) ($m_1=1$, $m_1'=0$, $m_1''=0$)

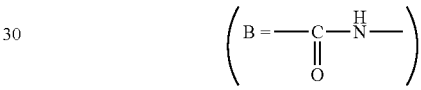

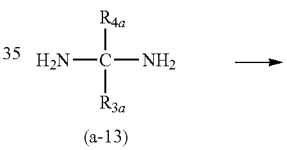

(a-13)

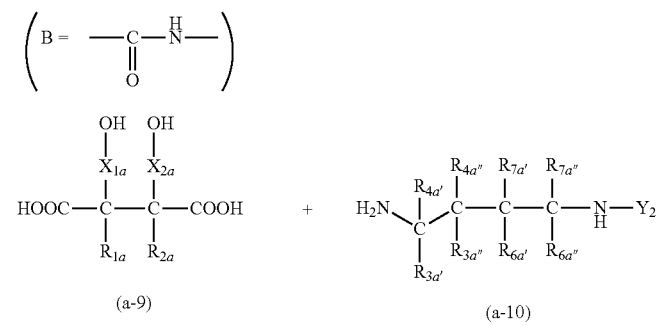

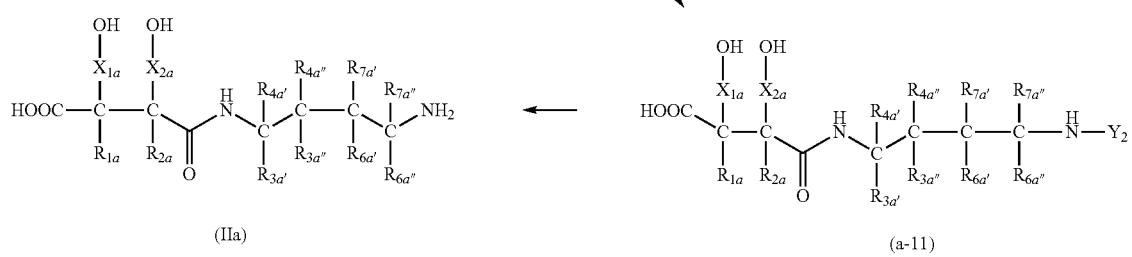

-continued

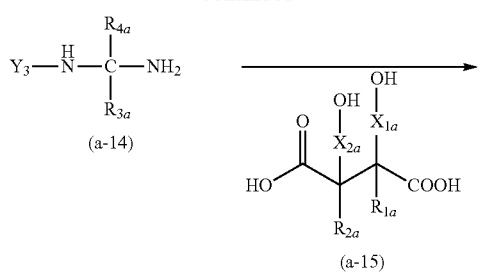

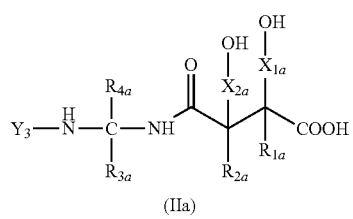

In the formulas, $Y_3$ is an amino-group-protecting group, and the definitions for the other individual symbols are as described above. As examples of the amino-group-protecting group, the same as those described above can be mentioned.

The reaction to dehydration-condense Compound (a-14) and Compound (a-15) by amidation is normally conducted by reacting these compounds in the presence of an equivalent of the amino compound and the carboxylic acid, using 1.1 equivalents or so of a condensing agent such as N-ethyl-N'-dimethylaminocarbodiimide or N-hydroxy-benzotriazol, in a solvent such as DMF or methylene chloride at room temperature for 1 hour to 10 hours or so.

Process 4: Production Method for General Formula (IIb) ($n_1-1=n_1'-1=n_2$)

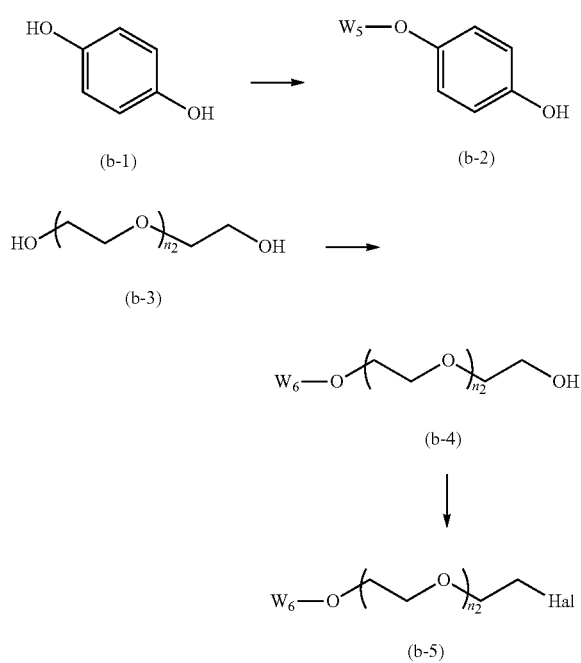

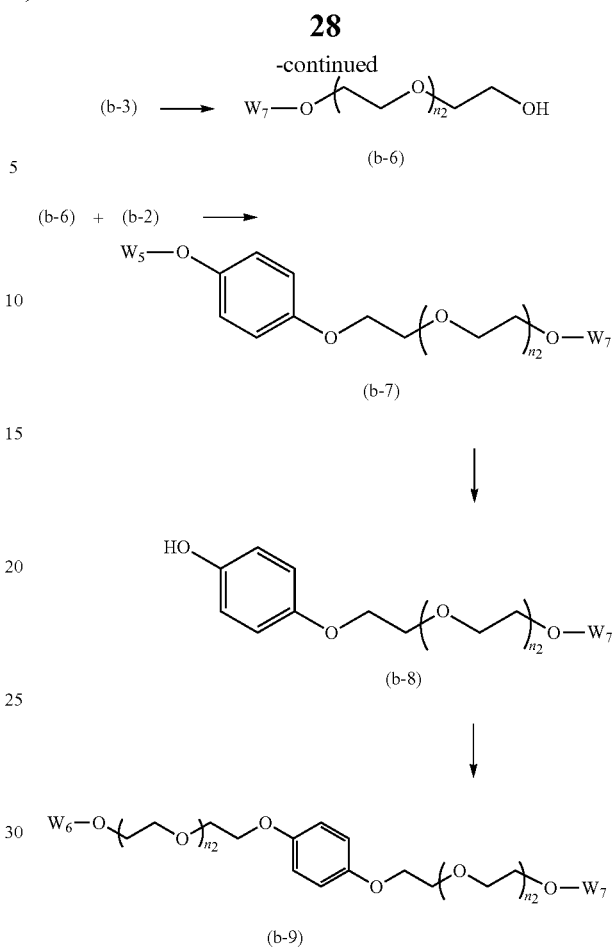

In the formulas, $W_5$-$W_7$ are hydroxyl-group-protecting groups, Hal represents a halogen atom (chlorine atom, bromine atom, iodine atom, fluorine atom), and the definitions for the other individual symbols are as described above. As examples of the hydroxyl-group-protecting group, the same as those described above can be mentioned. Note that $n_2$ is $n_1-1$ or $n_1'-1$ ($n_1$ and $n_1'$ are as described above).

Hydroxyl group protection and deprotection is appropriately performed using known methods and reagents according to the protective group used.

The halogen substitution reaction of Compound (b-4) to Compound (b-5) is normally conducted by reacting 2-3 equivalents of carbon tetrabromide and 1-2 equivalents of triphenylphosphine to 1 equivalent of the alcohol compound in a solvent such as methylene chloride, at 0° C. to room temperature, for 1 hour to several hours.

The dehydration-condensation reaction of Compound (b-6) and Compound (b-2) is normally conducted by reacting 1 equivalent of the alcohol compound and 1 equivalent of tributylphosphine in a toluene solvent at room temperature for 1 hour or so, adding thereto 1 equivalent of the phenol compound and a condensing agent such as 1,1'-azobis(N,N-dimethylformamide), and allowing the reaction at 0-50° C. for several hours to overnight.

The condensation reaction of Compound (b-8) and Compound (b-5) is normally conducted by reacting 1 equivalent of the phenol compound and about 10 times equivalents of a strong base like sodium hydride in excess at 0-10° C. in a solvent such as THF for 10-60 minutes or so, adding thereto 2 equivalents or so of the halogen compound, and allowing the reaction at room temperature for 1-10 hours or so.

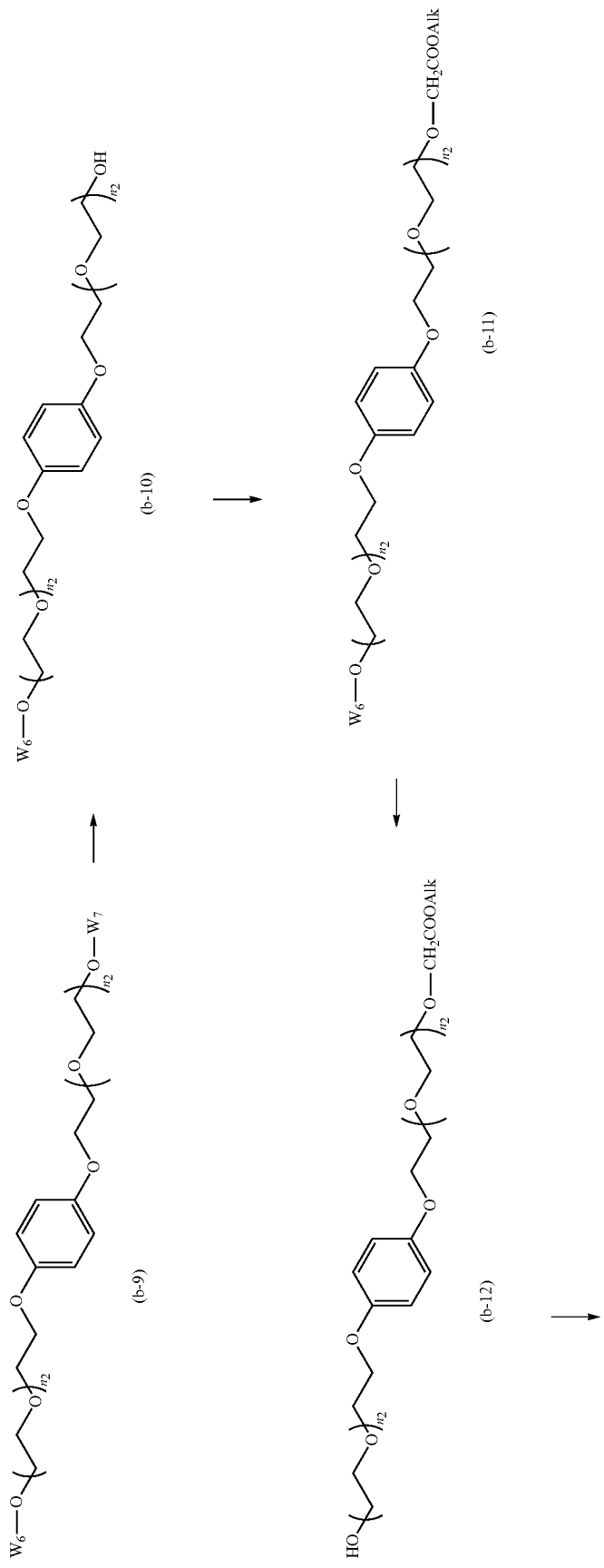

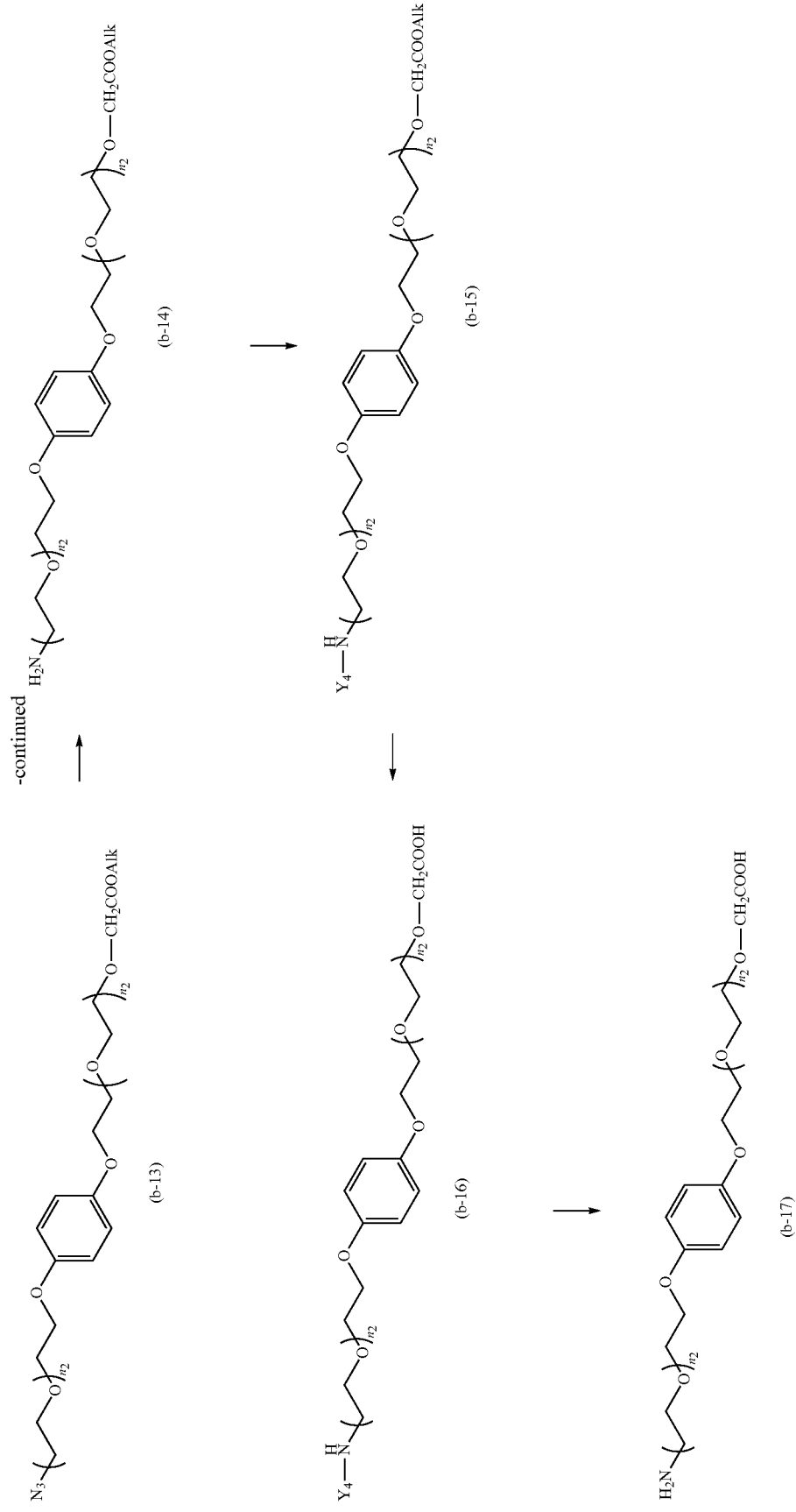

In the formulas, $W_6$-$W_7$ are hydroxyl-group-protecting groups, Alk is a linear or branched alkyl group having 1-3 carbon atoms (defined as described above), $Y_4$ is an amino-group-protecting group, and the definitions for the other individual symbols are as described above. As examples of the hydroxyl-group-protecting group and the amino-group-protecting group, the same as those described above can be mentioned.

Hydroxyl group or amino group deprotection or carboxyl group deprotection is appropriately performed using known methods and reagents according to the protective group used.

Alkoxycarbonylation of Compound (b-10) to Compound (b-11) is normally conducted by reacting 1 equivalent of the alcohol compound and 3-5 times equivalents or so of a strong base like sodium hydride in excess at 0-10° C. in a solvent such as THF, for 10-60 minutes or so, adding thereto 3-5 times equivalents or so of the halogen compound (bromoacetic acid-tert-butyl ester), and allowing the reaction at room temperature for 1-10 hours or so.

Azidation of Compound (b-12) to Compound (b-13) is normally conducted by reacting 1 equivalent of the alcohol compound, 1.5 equivalents or so of p-toluenesulfonyl chloride, and 0.2 equivalents or so of a base like 4-dimethylaminopyridine in a solvent such as pyridine at 30-50° C. for several hours, isolating the O-tosyl compound obtained, adding thereto about 10 times equivalents or so of sodium azide in excess, and allowing the reaction in a solvent such as DMF at 50-90° C. for several hours.

Amination of Compound (b-13) to Compound (b-14) is normally achieved by reacting 1 equivalent of the azide compound, using 0.1 equivalent or so of a catalyst like palladium hydroxide, in the presence of a solvent such as methanol under 1 to several atmospheric pressures of hydrogen at room temperature for several hours.

Process 5: Production Method for General Formula (IIc)

In each structural formula, particular groups and particular compounds are shown in some cases, which, however, are given for exemplification and are not to be construed as limiting. They are appropriately variable, as long as they retain an equivalent function.

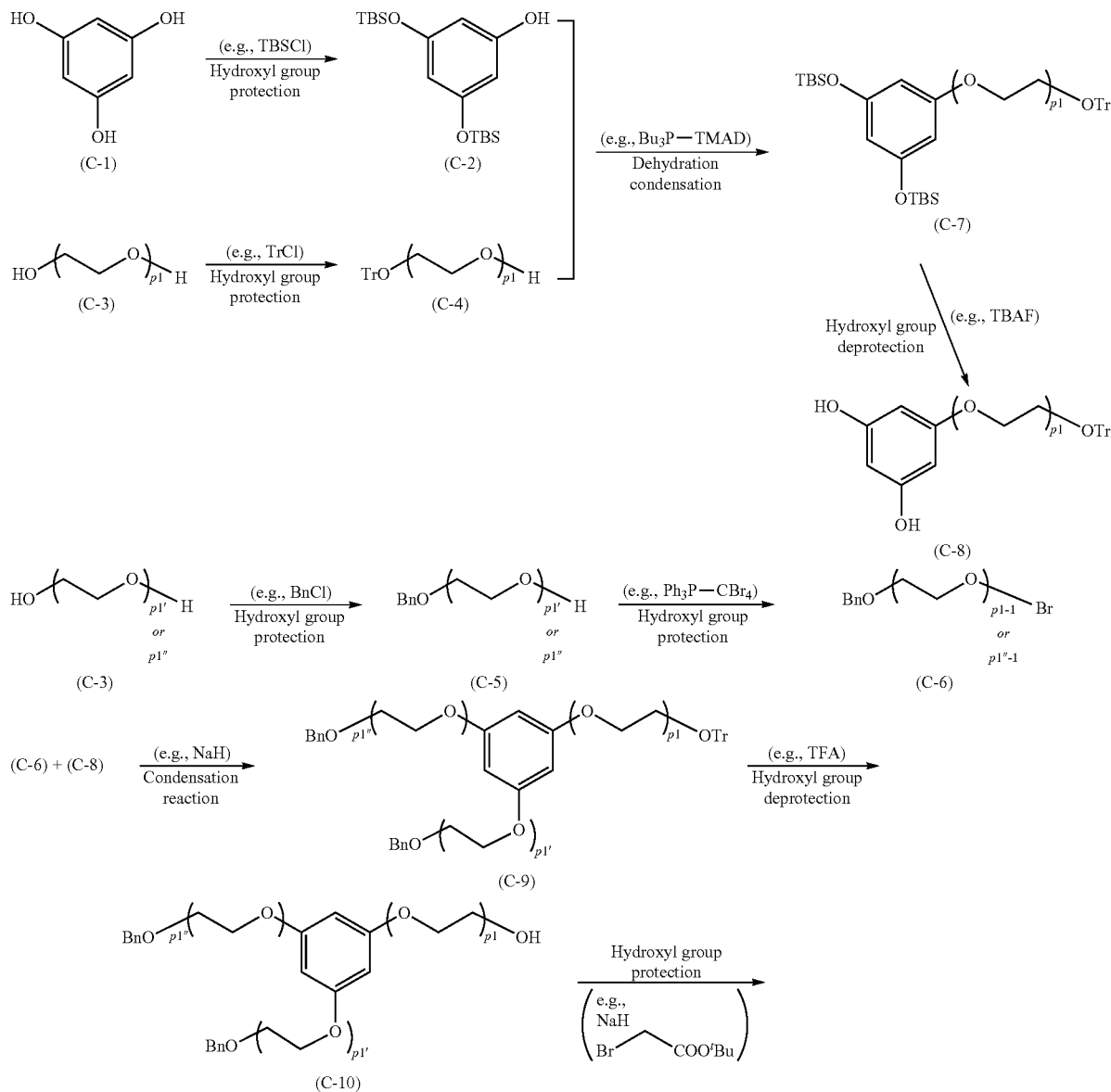

-continued
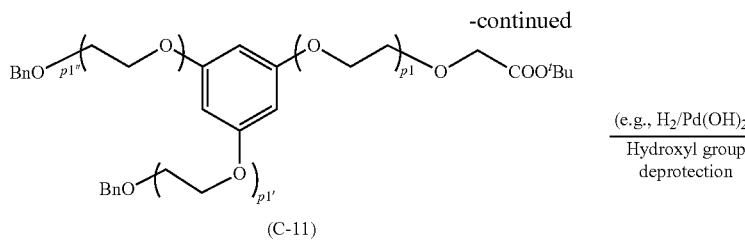
(C-11)
(e.g., H₂/Pd(OH)₂)
Hydroxyl group deprotection
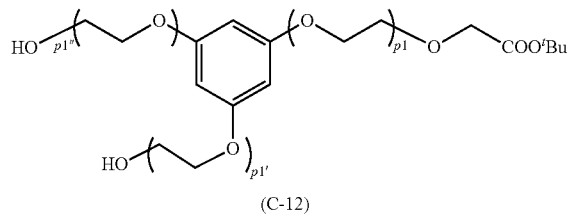
(C-12)
(C-12) →(e.g., TsCl) Hydroxyl group protection→ 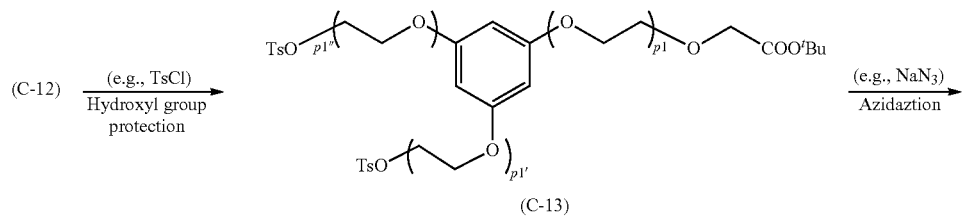 (C-13) →(e.g., NaN₃) Azidaztion→
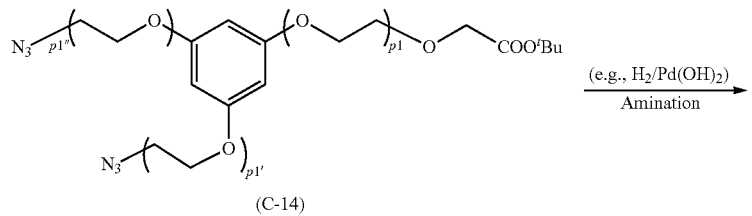
(C-14)
(e.g., H₂/Pd(OH)₂)
Amination
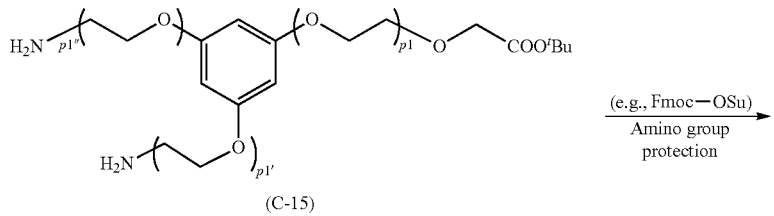
(C-15)
(e.g., Fmoc—OSu)
Amino group protection
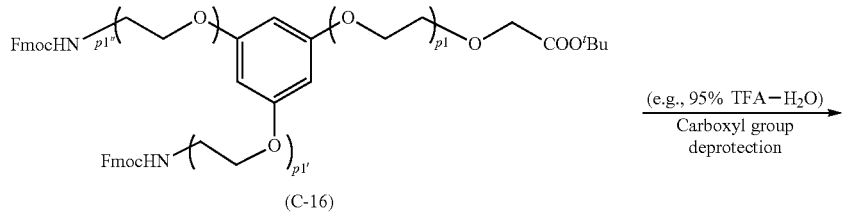
(C-16)
(e.g., 95% TFA—H₂O)
Carboxyl group deprotection
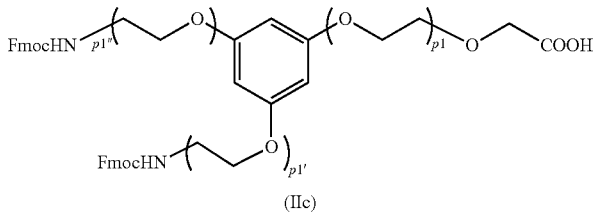
(IIc)

In the formulas, the definitions for individual symbols are as described above. The hydroxyl-group-protecting groups, amino-group-protecting groups and carboxyl-group-protecting groups in the formulas are given for exemplification, in addition to which groups optionally chosen groups in common use in the art are used. Specifically, the same as those described above can be mentioned as examples. It will be obvious to those skilled in the art that amino group protection, carboxyl group deprotection, and hydroxyl group protection and deprotection can be appropriately performed using known methods and reagents according to the protective group used, in addition to those described in the present specification.

Hydroxyl group protection of Compound (c-1) to Compound (c-2), when using TBS, for example, as the protective group, is normally conducted by reacting 1 equivalent of the phenol compound, 3 equivalents or so of a base (for example, imidazole) and 2 equivalents or so of silyl chloride in a solvent such as DMF at room temperature for 10 hours or so.

The dehydration-condensation reaction of Compound (c-2) and Compound (c-4) is normally conducted by reacting 1 equivalent of the alcohol compound and 1 equivalent of tributylphosphine in a toluene solvent at room temperature for 1 hour or so, adding thereto 1.3 equivalents of the phenol compound and 1.3 equivalents of a condensing agent such as 1,1'-azobis(N,N-dimethylformamide), and allowing the reaction at room temperature for several hours to overnight.

Hydroxyl group deprotection of Compound (c-7) to Compound (c-8) is normally conducted by reacting 1 equivalent of the phenol-protected compound (for example, silyl-protected compound) and 1.2 equivalents or so of tetrabutylammonium fluoride in a solvent such as THF at room temperature for 1 hour or so.

The condensation reaction of Compound (c-8) and Compound (c-6) is normally conducted by reacting 1 equivalent of the phenol compound and about 5.2 equivalents of a strong base like sodium hydride in excess at room temperature in a solvent such as THF or DMF for 10-60 minutes or so, adding thereto 4 equivalents or so of a halide (for example, alkyl bromide), and allowing the reaction at room temperature for about 4 hours or so. By this condensation reaction, Compound (c-9) is obtained.

Hydroxyl group deprotection of Compound (c-9) to Compound (c-10) is normally conducted by reacting 1 equivalent of a phenol-protected compound (for example, trityl-protected compound) in a solvent such as methylene chloride that contains TFA at room temperature for about 1 hour or so.

Hydroxyl group protection of Compound (c-10) to Compound (c-11), when using a tert-butoxycarbonyl group, for example, as the protective group, is normally conducted by reacting 1 equivalent of the alcohol compound, about 4 equivalents of a strong base such as sodium hydride, and about 4 equivalents of bromoacetic acid tert-butyl ester in a solvent such as THF or DMF at room temperature for about 4 hours or so.

Hydroxyl group deprotection of Compound (c-11) to Compound (c-12) is normally conducted by reacting 1 equivalent of a phenol-protected compound (for example, benzyl-protected compound) and a catalytic amount of palladium hydroxide in a hydrogen gas atmosphere in a solvent such as methanol at room temperature for about 6 hours or so.

Hydroxyl group protection of Compound (c-12) to Compound (c-13), when using Ts, for example, as the protective group, is normally conducted by reacting 1 equivalent of the alcohol compound, a catalytic amount of a base such as DMAP, and about 6 equivalents of tosyl chloride in a solvent such as pyridine at room temperature to 40° C. for about 2 hours or so.

Azidation of Compound (c-13) to Compound (c-14) is conducted by reacting 1 equivalent of the tosyl compound and about 15 equivalents of sodium azide in a solvent such as DMF at about 60° C. for about 2 hours or so.

Amination of Compound (c-14) to Compound (c-15) and amino-group-protecting group introduction to Compound (C-16) are normally conducted by reacting 1 equivalent of a phenol-protected compound (benzyl-protected compound) and a catalytic amount of palladium hydroxide in a hydrogen gas atmosphere in a solvent such as methanol at room temperature for about 1 hour or so, adding to the amine compound obtained (c-15) about 0.84 equivalents of 9-fluorenylmethylsuccinimidyl carbonate and about 1.5 equivalents of a base like triethylamine, and allowing the reaction in a solvent such as THF at room temperature for about 1 hour or so.

Carboxyl group deprotection of Compound (c-16) to Compound (IIc) is normally conducted by reacting 1 equivalent of a phenol-protected compound (for example, t-butyl-protected compound) in an aqueous solution that contains TFA at room temperature for about 10 hours or so.

Process 6: Production Method for General Formula (IId)
($R_{10a}=R_{9a}$=hydrogen atom, $R_{8a}$=hydrogen atom, $X_{4a}$=single bond)

In each structural formula, particular groups and particular compounds are shown in some cases, which, however, are given for exemplification and are not to be construed as limiting. They are appropriately variable, as long as they retain an equivalent function.

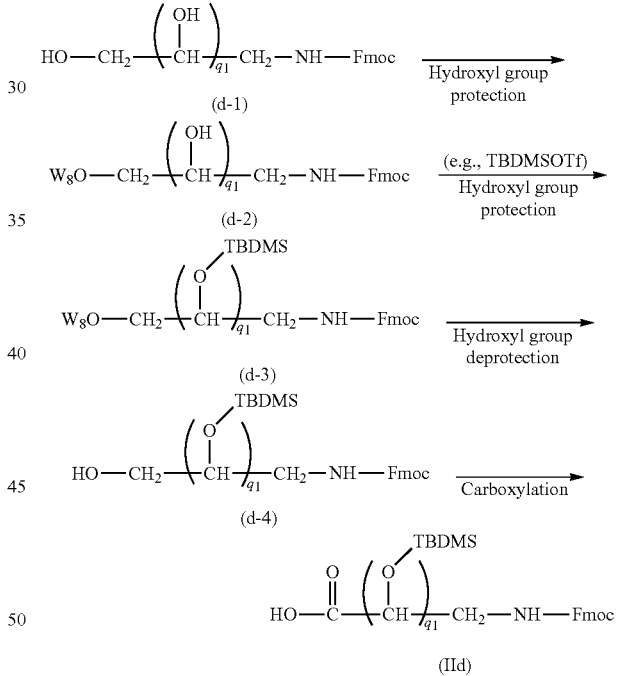

In the formulas, $W_8$ is a hydroxyl-group-protecting group, and the definitions for the other symbols are as described above. As examples of the hydroxyl-group-protecting group, the same as those described above can be mentioned. Hydroxyl group deprotection is appropriately performed using known methods and reagents according to the protective group used.

Carboxylation from Compound (d-4) to the desired Compound (IId) is normally achieved by reacting 1 equivalent of an alcohol compound with 10 equivalents of sodium periodate, 0.4 equivalents or so of an oxidant like ruthenium chloride hydrate (III) in the presence of a solvent such as water, acetonitrile or dichloromethane at room temperature for several hours.

Process 7: Production Method (1) for General Formula (IIe)
In each structural formula, particular groups and particular compounds are shown in some cases, which, however, are given for exemplification and are not to be construed as limiting. They are appropriately variable, as long as they retain an equivalent function.
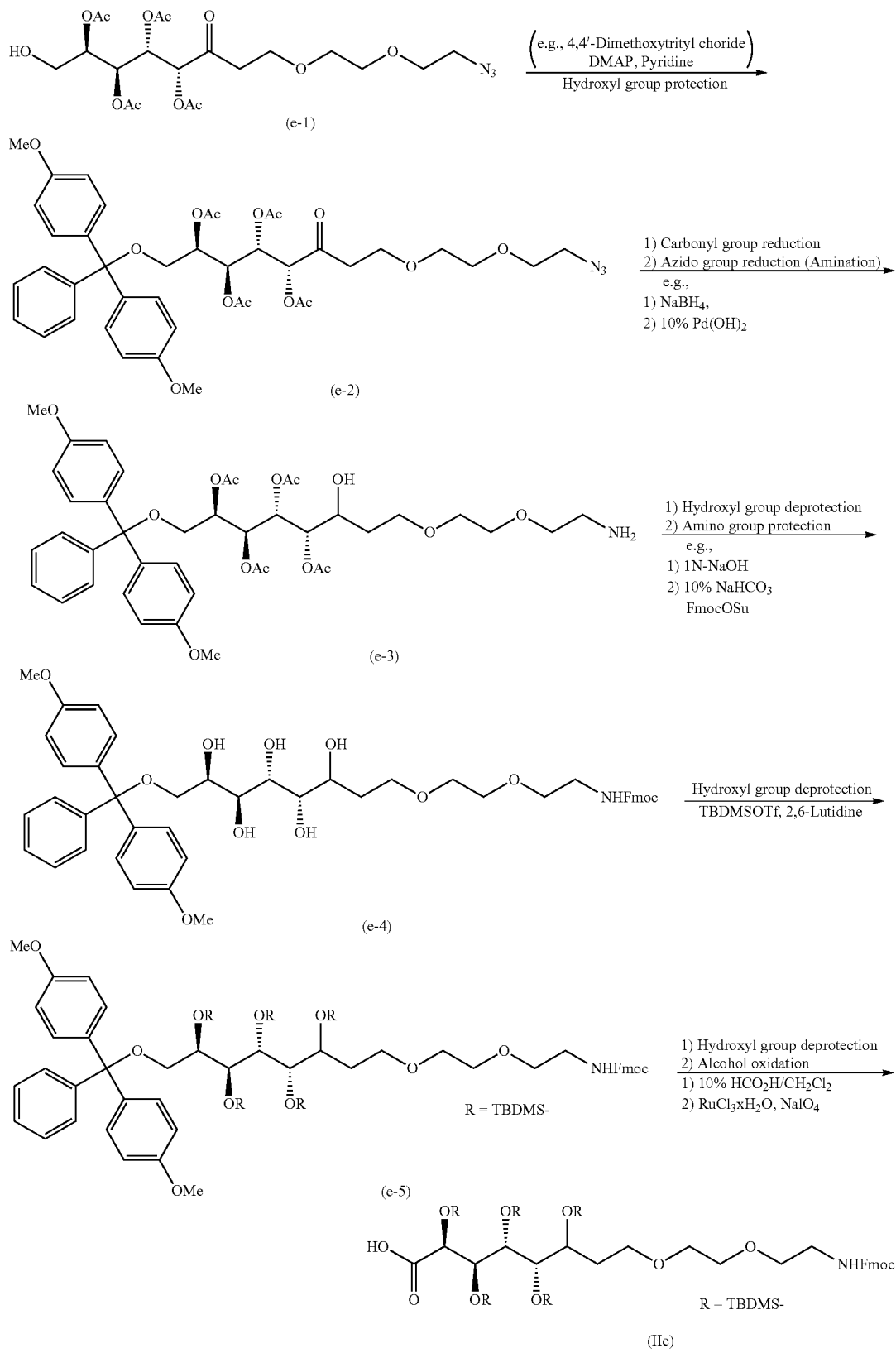

As examples of the hydroxyl-group-protecting group and the amino-group-protecting group, the same as those described above can be mentioned. Hydroxyl group deprotection is appropriately performed using known methods and reagents according to the protective group used.

The carbonyl group reduction reaction of Compound (e-2) to Compound (e-3) is conducted by reacting 1.2 equivalents or so of a reducing agent like $NaBH_4$ in a solvent such as methanol, and subsequently normally carrying out an azide group reduction reaction Lamination) of 1 equivalent of the azide compound and 0.1 equivalent or so of a catalyst like palladium hydroxide in the presence of a solvent such as methanol under 1 to several atmospheric pressures of hydrogen at room temperature for several hours.

Hydroxyl group deprotection of Compound (e-3) to Compound (e-4) can be conducted by reacting an alkali such as 1N sodium hydroxide in a mixed solvent of dioxane, water and the like, and subsequently protecting the amino group in the same manner as the reaction from (c-15) to (c-16).

Hydroxyl group protection of Compound (e-4) to Compound (e-5) can, for example, be conducted by reacting 20 equivalents or so of TBDMS-OTf in the presence of 2,6-Lutidine and the like.

Hydroxyl group deprotection of Compound (e-5) to Compound (IIe) can be conducted by allowing the reaction with 10% formic acid/dichloromethane, and subsequently oxidizing the alcohol in the same manner as the reaction from Compound (d-4) to Compound (IId).

Process 8: Production Method (2) for General Formula (IIe) ($R_{13a}$-$R_{16a}$=H, $R_{11a}$=H, $R_{12a}$=H, $r_1$=1)

can be appropriately performed using known methods and reagents according to the protective group used, in addition to those described in the present specification.

Azidation from Compound (e-7) to Compound (e-8) is conducted by reacting 1 equivalent of Compound (e-7), a catalytic amount of a base such as DMAP, and about 10 equivalents of tosyl chloride in a solvent such as methylene chloride at room temperature to 40° C. for about 2 hours to overnight to yield a tosyl derivative of Compound (e-7), and reacting 1 equivalent of the tosyl derivative obtained with about 15 equivalents of sodium azide in a solvent such as DMSO at about 60-70° C. for about 5 hours or so.

By aminating Compound (e-8), and subsequently protecting the amino group, Compound (IIe) is obtained.

Usually, the amine compound is obtained by reacting 1 equivalent of Compound (e-8) and a catalytic amount of palladium hydroxide in a hydrogen atmosphere in a solvent such as methanol or ethanol at room temperature for about 1-2 hours or so. Next, an amino-group-protecting group is introduced by reacting the amine compound obtained in accordance with a conventional method using, for example, 9-fluorenylmethylsuccinimidyl carbonate and the like, in the presence of a base like triethylamine in a solvent such as THF.

In the present invention, to polymerize a monomer component into a polymer, various methods in common use in the art are employed.

Specifically, the monomer component is polymerized by subjecting compounds represented by General Formulas (IIa)-(IIe) above to chemical reactions such as amidation, N-substitutional amidation, Schiff base formation (after Schiff base formation, the relevant portion may be subjected to a reduction reaction), esterification, and epoxy cleavage

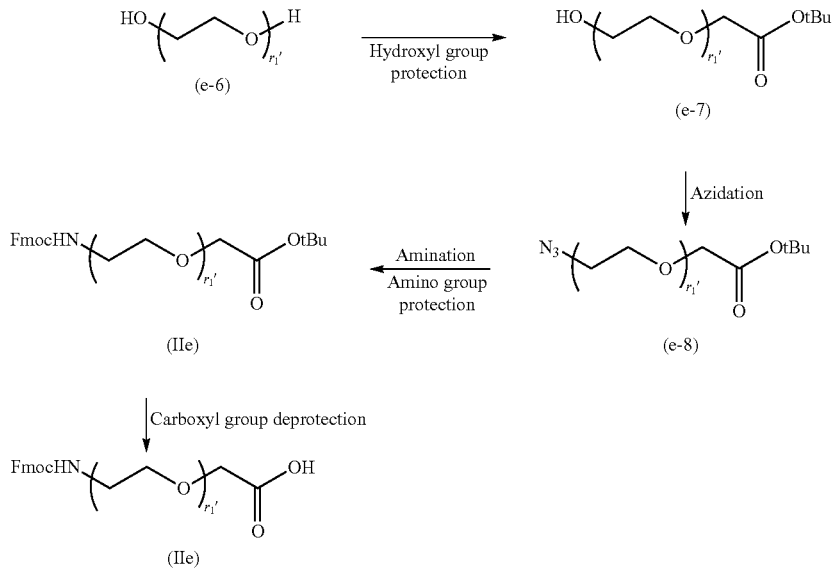

In the formulas, the definitions for individual symbols are as described above. The hydroxyl-group-protecting groups, amino-group-protecting groups and carboxyl-group-protecting groups in the formulas are given for exemplification, in addition to which groups optionally chosen groups in common use in the art are used. Specifically, the same as those described above can be mentioned as examples. It will be obvious to those skilled in the art that amino group protection, carboxyl group deprotection and hydroxyl group protection reaction with an amine or a hydroxyl group. Although the polymerization reaction can be conducted while the starting monomer component is in a free state, it is preferable, because of the ease of the subsequent purification step, to immobilize the starting monomer component onto a solid phase carrier and then conduct the polymerization reaction on the solid phase carrier. The reagents and reaction conditions used for these reactions are according to methods in common use in the art.

EXAMPLES

The present invention is hereinafter described in more detail by means of the following production examples, an example and an experimental example, which examples, however, are not to be construed as limiting the scope of the present invention.

Production Example 1

Synthesis of 17-allyl-14-(tert-butyl-dimethyl-silanyloxy)-1-hydroxy-12-{2-[4-(7-(tert-butyl-dimethyl-silanyloxy-carbonyl)heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone A mixture of 17-allyl-14-(tert-butyl-dimethyl-silanyloxy)-1-hydroxy-12-[2-(4-hydroxy-3-methoxy-cyclohexyl)-1-methyl-vinyl]-23,25-dimethoxy-13,19,21,27-tetramethyl-11,28-dioxa-4-aza-tricyclo[22.3.1.0$^{4,9}$]octacos-18-ene-2,3,10,16-tetraone (FK506; 138 mg, 0.15 mmol), O-mono(tert-butyl-dimethyl-silanyl)octanedioic acid (86.7 mg, 0.218 mmol), dimethylaminopyridine (DMAP; 16.5 mg, 0.098 mmol), 1-[3-(dimethylamino)propyl]-3-ethylcarbodiimide hydrochloride (EDC/HCl; 69.1 mg, 0.261 mmol) and methylene chloride (CH$_2$Cl$_2$; 1 ml) was stirred at room temperature for 1.5 hours. The reaction product was poured over an ethyl acetate-water mixed fluid and extracted. The organic phase obtained was washed with water and brine, after which it was dried with magnesium sulfate (MgSO$_4$). After the MgSO$_4$ was separated by filtration, concentration under reduced pressure was conducted. The residue thus obtained was purified using a silica gel column (eluted with 20% AcOEt (in n-hexane)) to yield the desired 17-allyl-14-(tert-

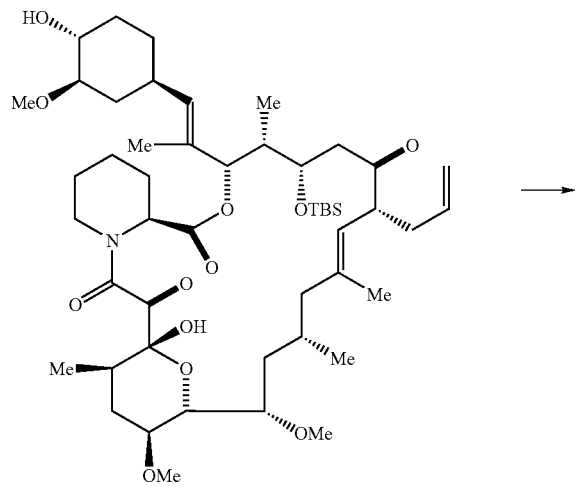

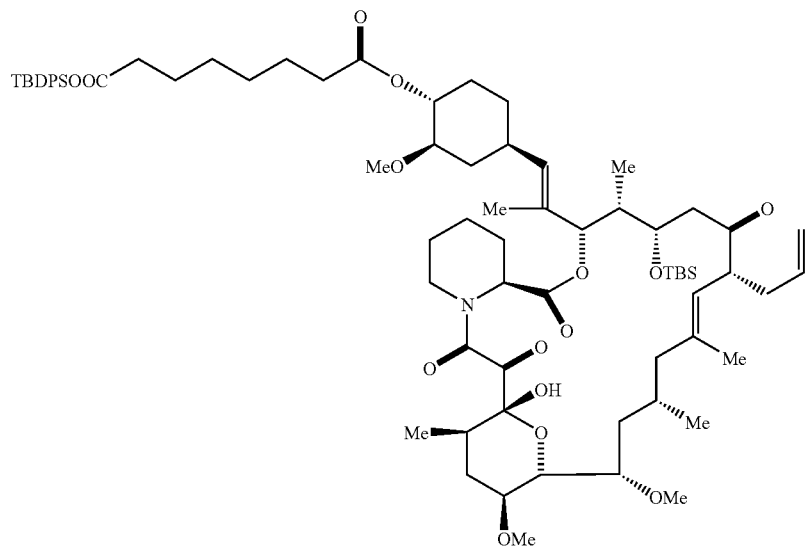

butyl-dimethyl-silanyloxy)-1-hydroxy-12-{2-[4-(7-(tert-butyl-dimethyl-silanyloxy-carbonyl)heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone (44 mg, 24.6%).

$^1$H-NMR(CDCl$_3$) δ: −0.1-0.1 (12H, m), 0.7-2.6 (47H, m), 0.85 and 0.86(18H, s), 1.50 (3H, s), 1.63 (3H, s), 2.75 (1H, m), 3.31 (3H, s), 3.35 (3H, s), 3.39 (3H, s), 4.05 (1H, m), 3.0-4.4 (6H), 4.5-5.8 (9H, m).

Production Example 2

Synthesis of 17-allyl-1,14-di-hydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone

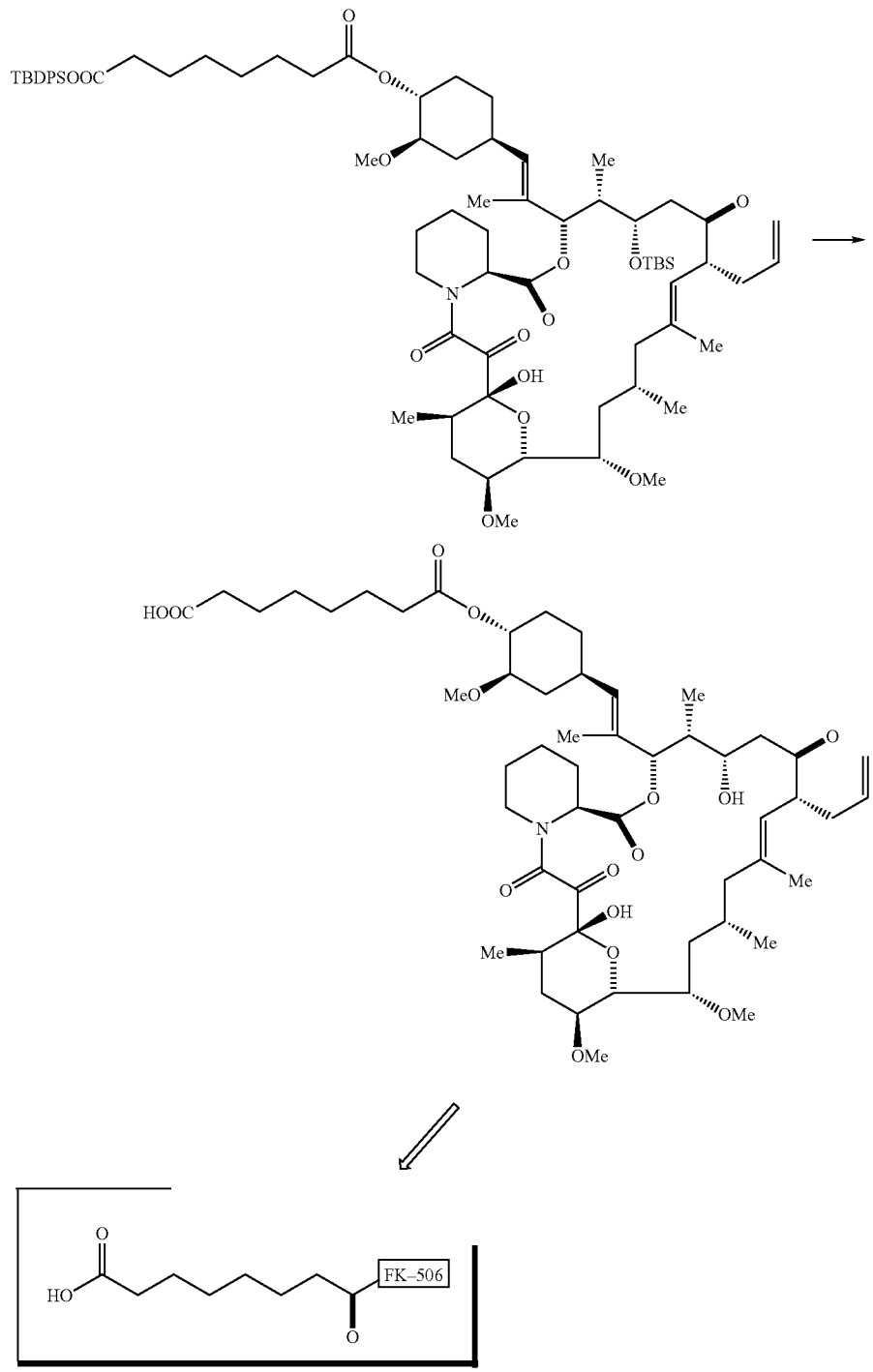

To a mixture of the 17-allyl-14-(tert-butyl-dimethyl-silanyloxy)-1-hydroxy-12-{2-[4-(7-(tert-butyl-dimethyl-silanyloxy-carbonyl)heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone prepared in Production Example 1 (44 mg, 0.037 mmol) and acetonitrile (0.88 ml), 46-48% aqueous hydrogen fluoride (HF) (0.12 ml) was gently added, and this was followed by overnight stirring at room temperature. The reaction product was poured over an ethyl acetate-water mixed fluid and extracted. The organic phase obtained was washed with water and brine, after which it was dried with magnesium sulfate (MgSO$_4$). After the MgSO$_4$ was separated by filtration, concentration under reduced pressure was conducted. The residue thus obtained was purified using a silica gel column (5% methanol (in chloroform)) to yield the desired 17-allyl-1,14-di-hydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone (14.2 mg, 40%).

$^1$H-NMR(CDCl$_3$) δ: 0.7-2.6 (47H, m), 1.50 (3H, s), 1.63 (3H, s), 2.75 (1H, m), 3.31 (3H, s), 3.35 (3H, s), 3.39 (3H, s), 4.05 (1H, m), 3.0-4.4 (6H), 4.5-5.8 (11H, m).

MS(m/z): 960(M+)

Production Example 3

Synthesis of TOYO-Pearl Resin (TSKgel AF-amino) with FK506

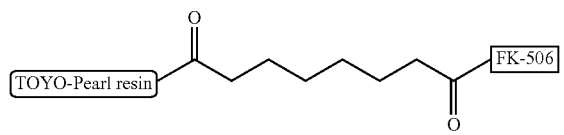

A mixture of the 17-allyl-1,14-dihydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone prepared in Production Example 2 (38.4 mg, 0.04 mmol), TOYO-Pearl resin (TSKgel AF-amino, 100 μl, free amino group (available amino group) content 0.01 mmol), EDC/HCl (9.2 mg, 0.048 mmol), 1-hydroxybenzotriazol (HOBt; 6.5 mg, 0.048 mmol) and dimethylformamide (DMF; 1 ml) was stirred at room temperature for 6 hours. The reaction end point was confirmed as the time when no residual amino group became visually observable by the ninhydrin reaction. The reaction rate at this time was calculated to be about 82%. After confirmation of completion of the reaction, the resin was washed with DMF five times. Acetic anhydride (100 μl) and DMF (400 μl) were added thereto, and this was followed by stirring at room temperature for 1 hour. Subsequently, the resin was thoroughly washed with DMF, and the TOYO-Pearl resin with FK506 obtained was used in the binding experiments described below. In the groups that interlie between the TOYO-Pearl resin and FK506, the number of HBA is 4 and the number of HBD is 3 (however, those coming from the groups introduced to FK506 in advance are not counted). The number of HBA and the number of HBD come from the commercially available linker of TOYO-Pearl resin.

Production Example 4

Synthesis of AffiGel Resin with FK506

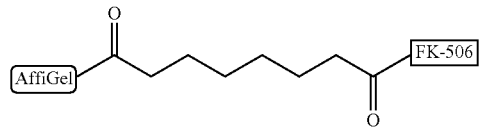

AffiGel resin with FK506 was synthesized by the same technique as Production Example 3 except that AffiGel resin (Bio-Rad Company) was used in place of TOYO-Pearl resin. The AffiGel resin with FK506 obtained was used in the binding experiments described below. In the groups that interlie between the AffiGel resin and FK506, the number of HBA is 3 and the number of HBD is 2 (however, those coming from the groups introduced to FK506 in advance are not counted). The number of HBA and the number of HBD come from the commercially available linker of Affigel resin.

Production Example 5

Synthesis (1-1) of Hydrophilic Spacer Molecule

Synthesis of 2-(2-{2-[2-(2-trityloxy-ethoxy)-ethoxy]-ethoxy}-ethoxy) ethanol

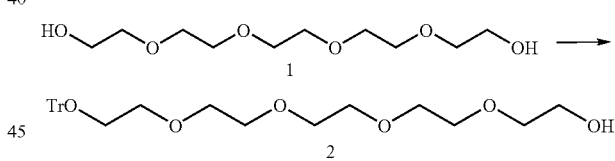

Pentaethylene glycol (Compound 1; 10 g, 42.0 mmol) was dissolved in pyridine (100 ml), triphenylmethyl chloride (11.6 g, 41.6 mmol) and 4-dimethylaminopyridine (0.9 g, 7.4 mmol) were added at room temperature, and this was followed by overnight stirring at 35° C. This was concentrated under reduced pressure; the residue obtained was dissolved in chloroform, the organic phase was washed with saturated aqueous sodium hydrogen carbonate and saturated brine, after which it was dried with sodium sulfate. The solid was removed by cotton filtration and washed with chloroform, and the filtrate and the washings were combined and concentrated under reduced pressure. The residue obtained was subjected to silica gel column chromatography (Kanto Chemical 60N; 600 ml) with an eluent (60:1 chloroform (CHCl$_3$)-methanol (MeOH)) to yield the desired 2-(2-{2-[2-(2-trityloxy-ethoxy)-ethoxy]-ethoxy}-ethoxy)ethanol (Compound 2; 10.4 g, 51.2%).

$^1$H-NMR(CDCl$_3$) δ: 2.53 (1H, t), 3.16 (2H, t), 3.49-3.63 (18H, m), 7.14-7.41 (15H, m).

Production Example 6

Synthesis (1-2) of Hydrophilic Spacer Molecule

Synthesis of [2-(2-{2-[2-(2-trityloxy-ethoxy)-ethoxy]-ethoxy}-ethoxy)-ethoxy]acetic acid

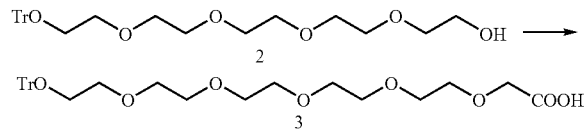

The Compound 2 obtained in Production Example 5 (10.2 g, 21.2 mmol) was dissolved in a mixed solvent of tetrahydrofuran (THF; 200 ml) and DMF (50 ml), sodium hydride (3.1 g; oily, 60 wt %) was added little by little at 0° C., and this was followed by stirring at room temperature for 30 minutes. After this was cooled to 0° C., bromoacetic acid (6.5 g, 46.8 mmol) was added little by little, and this was followed by stirring at room temperature for 30 minutes. Subsequently, sodium hydride (11.6 g; oily, 60 wt %) was further added little by little at room temperature, and this was followed by stirring at room temperature for 1 hour. The reaction solution was cooled to 0° C., and water (25 ml) was gradually added, after which the reaction solution was concentrated under reduced pressure until the volume thereof became about 100 ml. Ethyl acetate (200 ml) and brine (100 ml) were added thereto, and 2M aqueous potassium hydrogen sulfate was added with stirring to obtain a pH of 6. The organic phase was extracted and concentrated under reduced pressure at 30° C.; the residue obtained was subjected to silica gel column chromatography (Kanto Chemical 60N; 400 ml) with an eluent (85:15 CHCl$_3$-MeOH) to yield a crude product of the desired [2-(2-{2-[2-(2-trityloxy-ethoxy)-ethoxy]-ethoxy}-ethoxy)-ethoxy]acetic acid (Compound 3) (12.4 g).

$^1$H-NMR(CDCl$_3$) δ: 3.34 (2H, t), 3.76-3.84 (20H, m), 4.13 (2H, s) 7.30-7.83 (15H, m).

Production Example 7

Synthesis (1-3) of Hydrophilic Spacer Molecule

Synthesis of [2-(2-{2-[2-(2-trityloxy-ethoxy)-ethoxy]-ethoxy}-ethoxy)-ethoxy]acetic acid benzyl ester

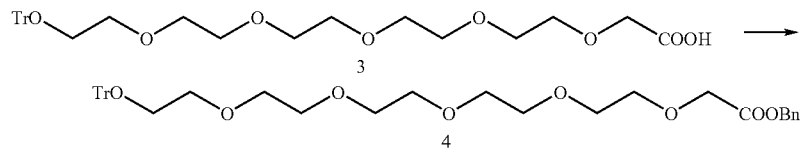

The crude product of Compound 3 obtained in Production Example 6 (12.4 g) was dissolved in methylene chloride (100 ml), and 4-dimethylaminopyridine (0.29 g, 2.4 mmol) and benzyl alcohol (3.1 ml, 30.0 mmol) were added. This was cooled to 0° C., water-soluble carbodiimide (N-ethyl-N'-(3'-dimethylaminopropyl)carbodiimide; WSC; 4.5 g, 23.5 mmol) was added, and this was followed by overnight stirring at room temperature. The reaction solution was extracted with chloroform, and the organic phase was washed with saturated aqueous sodium hydrogen carbonate and saturated brine, after which it was dried with sodium sulfate. The solid was removed by cotton filtration and washed with chloroform, and the filtrate and the washings were combined and concentrated under reduced pressure. The residue obtained was subjected to silica gel column chromatography (Kanto Chemical 60N; 600 ml) with an eluent (1:1 ethyl acetate-hexane) to yield the desired [2-(2-{2-[2-(2-trityloxy-ethoxy)-ethoxy]-ethoxy}-ethoxy)-ethoxy]acetic acid benzyl ester (Compound 4; 12.0 g, 90.1%, 2 steps).

$^1$H-NMR(CDCl$_3$) δ: 3.16 (2H, t), 3.55-3.65 (20H, m), 4.11 (2H, s), 5.11 (2H, s), 7.15-7.40 (20H, m).

Production Example 8

Synthesis (1-4) of Hydrophilic Spacer Molecule

Synthesis of [2-(2-{2-[2-(2-hydroxy-ethoxy)-ethoxy]-ethoxy}-ethoxy)-ethoxy]acetic acid benzyl ester

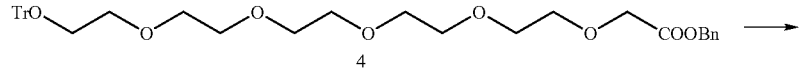

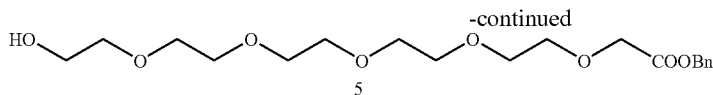

The Compound 4 obtained in Production Example 7 (12.0 g) was dissolved in a 5% solution of trifluoroacetic acid in methylene chloride (150 ml), water (10 ml) was added at 0° C., and this was followed by stirring at 0° C. for 20 minutes. The reaction solution was poured over saturated aqueous sodium hydrogen carbonate, extracted, and dried with sodium sulfate. The solid was removed by cotton filtration and washed with chloroform, and the filtrate and the washings were combined and concentrated under reduced pressure. The residue obtained was subjected to silica gel column chromatography (Kanto Chemical 60N; 400 ml) with an eluent (1000:15 $CHCl_3$-MeOH) to yield the desired [2-(2-{2-[2-(2-hydroxy-ethoxy)-ethoxy]-ethoxy}-ethoxy)-ethoxy]acetic acid benzyl ester (Compound 5; 7.0 g, 95%).

$^1$H-NMR($CDCl_3$) δ: 2.80 (1H, t), 3.62-3.76 (20H, m), 4.22 (2H, s), 5.20 (2H, s), 7.36-7.41 (5H, m).

Production Example 9

Synthesis (1-5) of Hydrophilic Spacer Molecule

Synthesis of [2-(2-{2-[2-(2-azido-ethoxy)-ethoxy]-ethoxy}-ethoxy)-ethoxy]acetic acid benzyl ester

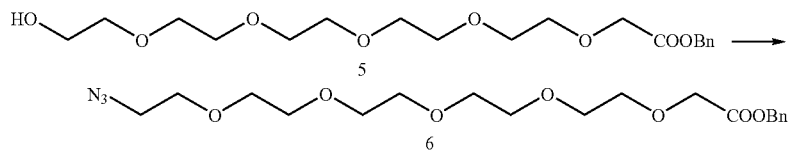

The Compound 5 obtained in Production Example 8 (7.0 g, 18.1 mmol) and 4-dimethylaminopyridine (0.4 g, 3.3 mmol) were dissolved in pyridine (45 ml), and this solution was cooled to 0° C. p-Toluenesulfonyl chloride (5.2 g, 27.2 mmol) was added thereto, this was followed by overnight stirring at room temperature, p-toluenesulfonyl chloride (3.1 g, 16.2 mmol) and 4-dimethylaminopyridine (120 mg, 0.98 mmol) were further added, and this was followed by stirring at 30° C. for 2 hours. The reaction solution was cooled to 0° C., water (3 ml) was added, concentration under reduced pressure was conducted, the residue obtained was dissolved in ethyl acetate, and the organic phase was washed with saturated aqueous sodium hydrogen carbonate and saturated brine, after which it was dried with sodium sulfate. The solid was removed by cotton filtration and washed with ethyl acetate, and the filtrate and the washings were combined and concentrated under reduced pressure. The residue obtained was dissolved in DMF (50 ml), sodium azide (11.8 g, 0.18 mol) was added, and this was followed by stirring at 60° C. for 1 hour. The reaction solution was extracted with ethyl acetate, and the organic phase was washed with saturated aqueous sodium hydrogen carbonate and saturated brine, after which it was dried with sodium sulfate. The solid was removed by cotton filtration and washed with ethyl acetate, and the filtrate and the washings were combined and concentrated under reduced pressure. The residue obtained was subjected to silica gel column chromatography (Kanto Chemical 60N; 250 ml) with an eluent (3:1 ethyl acetate-hexane) to yield the desired [2-(2-{2-[2-(2-azido-ethoxy)-ethoxy]-ethoxy}-ethoxy)-ethoxy]acetic acid benzyl ester (Compound 6; 3.3 g, 44.3%).

$^1$H-NMR($CDCl_3$) δ: 3.31 (2H, t), 3.54-3.87 (20H, m), 4.13 (2H, s), 5.12 (2H, s), 7.20-7.30 (5H, m).

Production Example 10

Synthesis (1-6) of Hydrophilic Spacer Molecule

Synthesis of [2-(2-{2-[2-(2-amino-ethoxy)-ethoxy]-ethoxy}-ethoxy)-ethoxy]acetic acid

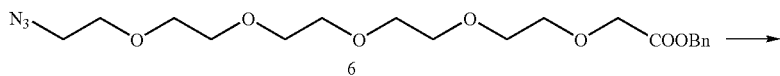

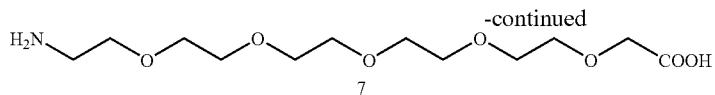

The Compound 6 obtained in Production Example 9 (1.94 g, 4.72 mmol) was dissolved in methanol (50 ml), 10% Pd—C (500 mg) was added, and catalytic hydrogenation was conducted at room temperature for 2.5 hours. The solid was removed by Celite filtration and washed with methanol, and the filtrate and the washings were combined and concentrated under reduced pressure to yield the desired [2-(2-{2-[2-(2-amino-ethoxy)-ethoxy]-ethoxy}-ethoxy)-ethoxy]acetic acid (Compound 7; 1.4 g, quantitative).
MS (m/z): 296 (M$^+$)

Production Example 11

Synthesis (1-7) of Hydrophilic Spacer Molecule

Synthesis of {2-[2-(2-{2-[2-(9H-fluoren-9-yl-methoxycarbonylamino)-ethoxy]-ethoxy}-ethoxy)-ethoxy]-ethoxy}acetic acid

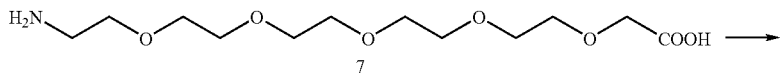

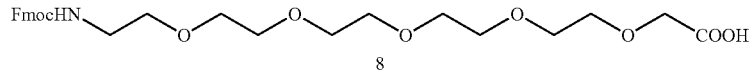

The Compound 7 obtained in Production Example 10 (1.25 g, 4.23 mmol) was dissolved in 10% aqueous sodium carbonate (14 ml), 9-fluorenylmethylsuccinimidyl carbonate (2.15 g, 6.37 mmol) in suspension in dimethoxyethane (14 ml) was added drop by drop at room temperature, and this was followed by overnight stirring at room temperature. The solid was separated by filtration with Celite, after which it was washed with chloroform. The filtrate and the washings were combined and extracted with chloroform, and the organic phase was washed with 2M aqueous sodium hydrogen sulfate and saturated brine and dried with sodium sulfate. The solid was removed by cotton filtration and washed with chloroform, and the filtrate and the washings were combined and concentrated under reduced pressure. The residue obtained was subjected to silica gel column chromatography (Kanto Chemical 60N; 150 ml) with an eluent (1000:7 CHCl$_3$-MeOH) to yield the desired {2-[2-(2-{2-[2-(9H-fluoren-9-yl-methoxycarbonylamino)-ethoxy]-ethoxy}-ethoxy)-ethoxy]-ethoxy}acetic acid (Compound 8; 1.38 g, 63.0%).
$^1$H-NMR(CDCl$_3$) δ: 3.34 (2H, t), 3.50-3.71 (18H, m), 4.05 (2H, s), 4.12 (1H, t), 4.33 (2H, d), 5.57 (1H, s), 7.22-7.95 (8H, m).

Production Example 12

Synthesis of Resin with Hydrophilic Spacer: Synthesis of TOYO-Pearl Resin (TSKgel AF-Amino) with Hexaethylene Glycol Derivative

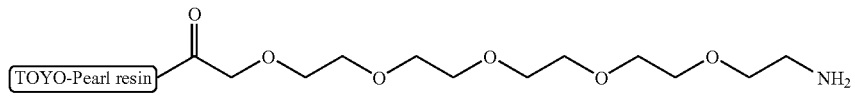

To TOYO-Pearl resin (TSKgel AF-amino; 0.01 mmol amine is present in 100 µl), {2-[2-(2-{2-[2-(9H-fluoren-9-yl-methoxycarbonylamino)-ethoxy]-ethoxy}-ethoxy)-ethoxy]-ethoxy}acetic acid (Compound 8 obtained in Production Example 11; 21 mg, 0.04 mmol) in solution in a mixed solvent of methylene chloride (0.4 ml) and N-methyl-2-pyrrolidone (NMP; 0.1 ml) was added; benzotriazol-1-yl-oxy-tris-pyrolidino-phosphonium hexafluorophosphate (PyBOP; 26 mg, 0.05 mmol) and N,N-diisopropylethylamine (17 µl, 0.10 mmol) were further added, and this was followed by shaking at room temperature for 4 hours. After completion of the reaction, the resin was thoroughly washed with methylene chloride and DMF, after which the percent condensation yield was measured by the ninhydrin test (about 81%). To the resin obtained, a mixed solution of acetic anhydride/methylene chloride/NMP (1/8/2) (0.5 ml) was added; this was followed by shaking at room temperature for 3 hours. The resin was thoroughly washed with methylene chloride and DMF, after which a mixed solution of piperidine/DMF/methylene chloride (1/4/4) (0.5 ml) was added, and this was followed by shaking at room temperature for 3 hours. After completion of the reaction, the resin was thoroughly washed with ethylene chloride and DMF, after which the presence of about 7.9 µmol of the amine in 100 µl of the resin was confirmed by the ninhydrin test.

Production Example 13

Synthesis of Resin with FK506-Derivative-Bound Hydrophilic Spacer (TOYO+(PEG)$_1$–FK506)

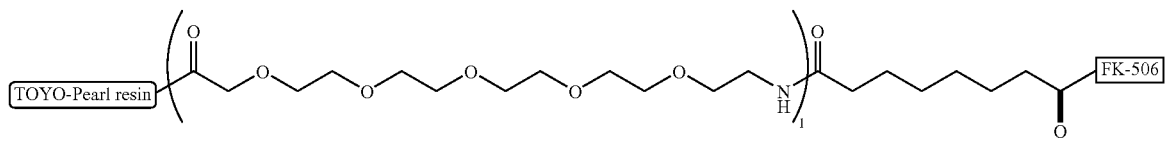

Using the TOYO-Pearl resin with hexaethylene glycol derivative obtained in Production Example 12, an FK506-bound resin having a hydrophilic spacer [TOYO+(PEG)$_1$–FK506] was synthesized in accordance with the method described in Production Example 3. In the hydrophilic spacer portion that interlies between the TOYO-Pearl resin and FK506, the number of HBA is 11 and the number of HBD is 4. Note that without considering the number of HBA and the number of HBD coming from the linker of the TOYO-Pearl resin, the number of HBA is 7 and the number of HBD is 1 in the hydrophilic spacer.

Production Example 14

Synthesis of Resin with FK506-Derivative-Bound Hydrophilic Spacer (TOYO+(PEG)$_2$–FK506)

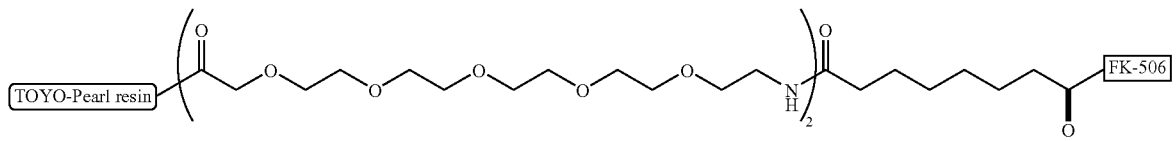

Using the TOYO-Pearl resin with hexaethylene glycol derivative obtained in Production Example 12, a hydrophilic spacer elongation reaction was conducted according to Production Example 12, after which an FK506-bound resin having a hydrophilic spacer [TOYO+(PEG)$_2$–FK506] was synthesized in accordance with the method described in Production Example 3. In the hydrophilic spacer portion that interlies between the TOYO-Pearl resin and FK506, the number of HBA is 18 and the number of HBD is 5. Note that without considering the number of HBA and the number of HBD coming from the linker of the TOYO-Pearl resin, the number of HBA is 14 and the number of HBD is 2 in the hydrophilic spacer.

Production Example 15

Synthesis of Resin with FK506-Derivative-Bound Hydrophilic Spacer (TOYO+(PEG)$_3$–FK506)

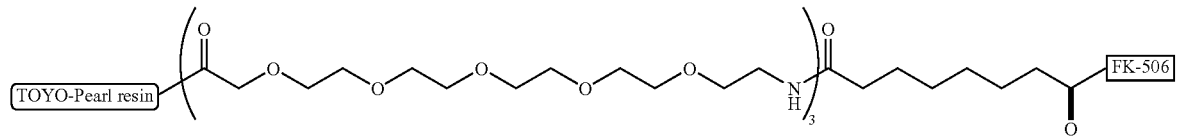

Using the TOYO-Pearl resin with hexaethylene glycol derivative obtained in Production Example 12, a hydrophilic spacer elongation reaction was repeatedly conducted according to Production Example 12, after which an FK506-bound resin having a hydrophilic spacer [TOYO+(PEG)$_3$–FK506] was synthesized in accordance with the method described in Production Example 3. In the hydrophilic spacer portion that interlies between the TOYO-Pearl resin and FK506, the number of HBA is 25 and the number of HBD is 6. Note that without considering the number of HBA and the number of HBD coming from the linker of the TOYO-Pearl resin, the number of HBA is 21 and the number of HBD is 3 in the hydrophilic spacer.

Production Example 16

Synthesis of Resin with FK506-Derivative-Bound Hydrophilic Spacer (TOYO+(PEG)$_4$–FK506)

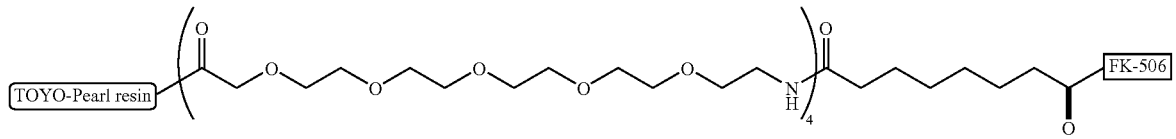

Using the TOYO-Pearl resin with hexaethylene glycol derivative obtained in Production Example 12, a hydrophilic spacer elongation reaction was repeatedly conducted according to Production Example 12, after which an FK506-bound resin having a hydrophilic spacer [TOYO+(PEG)$_4$–FK506] was synthesized in accordance with the method described in Production Example 3. In the hydrophilic spacer portion that interlies between the TOYO-Pearl resin and FK506, the number of HBA is 32 and the number of HBD is 7. Note that without considering the number of HBA and the number of HBD derived from the linker of the TOYO-Pearl resin, the number of HBA is 28 and the number of HBD is 4 in the hydrophilic spacer.

Production Example 17

Synthesis of Resin with FK506-Derivative-Bound Hydrophilic Spacer (TOYO+(PEG)$_5$–FK506)

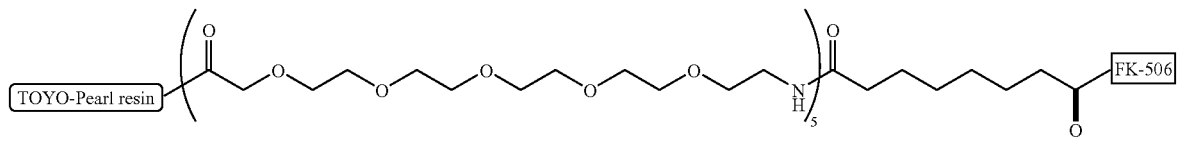

Using the TOYO-Pearl resin with hexaethylene glycol derivative obtained in Production Example 12, a hydrophilic spacer elongation reaction was repeatedly conducted according to Production Example 12, after which an FK506-bound resin having a hydrophilic spacer [TOYO+(PEG)$_5$–FK506] was synthesized in accordance with the method described in Production Example 3. In the hydrophilic spacer portion that interlies between the TOYO-Pearl resin and FK506, the number of HBA is 39 and the number of HBD is 8. Note that without considering the number of HBA and the number of HBD derived from the linker of the TOYO-Pearl resin, the number of HBA is 35 and the number of HBD is 5 in the hydrophilic spacer.

Production Example 18

Synthesis of Resin with FK506-Derivative-Bound Hydrophilic Spacer (TOYO+(PEG)$_6$–FK506)

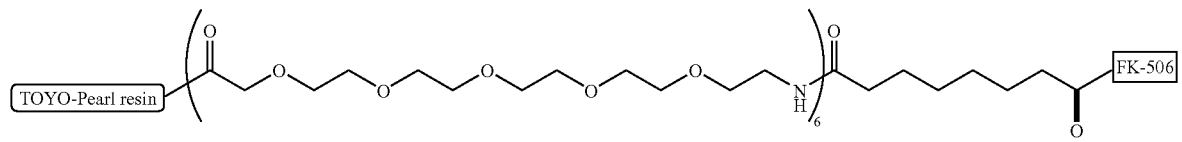

Using the TOYO-Pearl resin with hexaethylene glycol derivative obtained in Production Example 12, a hydrophilic spacer elongation reaction was repeatedly conducted according to Production Example 12, after which an FK506-bound resin having a hydrophilic spacer [TOYO+(PEG)$_6$–FK506] was synthesized in accordance with the method described in Production Example 3. In the hydrophilic spacer portion that interlies between the TOYO-Pearl resin and FK506, the number of HBA is 46 and the number of HBD is 9. Note that without considering the number of HBA and the number of HBD derived from the linker of the TOYO-Pearl resin, the number of HBA is 42 and the number of HBD is 6 in the hydrophilic spacer.

Production Example 19

Synthesis (2-1) of Hydrophilic Spacer Molecule

Synthesis of (5S-aminomethyl-2,2-dimethyl-[1,3]dioxolan-4S-ylmethyl)carbamic acid 9H-fluoren-9-ylmethyl ester (Compound 10)

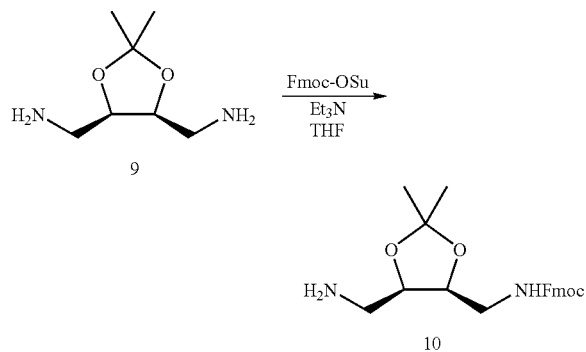

Compound 9 (1.0 g, 6.25 mmol) was dissolved in 20 ml of THF, and this was followed by stirring under ice cooling. To the reaction system, 9-fluorenylmethylsuccinimidyl carbonate (Fmoc-Osu; 2.1 g, 6.25 mmol) dissolved in 10 ml of THF was gradually added drop by drop. Subsequently, triethylamine was added drop by drop, and this was followed by stirring under ice cooling for 30 minutes. After completion of the reaction, water was added, the water phase was extracted with ethyl acetate, and the organic phase was washed with saturated brine, after which it was dried with anhydrous magnesium sulfate. The organic phase obtained was concentrated under reduced pressure and purified by silica gel column chromatography (BW-820 MH; Fuji Silysia Chemical Ltd., developing solvent (10:1=ethyl acetate:ethanol)) to yield the desired Compound 10 (1.22 g) at a percent yield of 52.8%.

MS (m/z): 383 (MH$^+$), $^1$H-NMR(DMSO d$_6$) δ: 1.30 (s, 6H), 2.68 (d, 2H), 3.07 (m, 2H), 3.63-3.6 (m, 1H), 3.69-4.02 (m, 1H), 4.04-4.21 (m, 1H), 4.29 (m, 2H), 7.33 (m, 2H), 7.42 (t, 2H), 7.70 (d, 2H), 7.89 (d, 2H).

Production Example 20

Synthesis (2-2) of Hydrophilic Spacer Molecule

Synthesis of 5R-({5S-[(9H-fluoren-9-ylmethoxycarbonylamino)-methyl]-2,2-dimethyl-[1,3]dioxolan-4R-ylmethyl}-carbamoyl)-2,2-dimethyl-[1,3]dioxolan-4S-carboxylic acid benzyl ester (Compound 11)

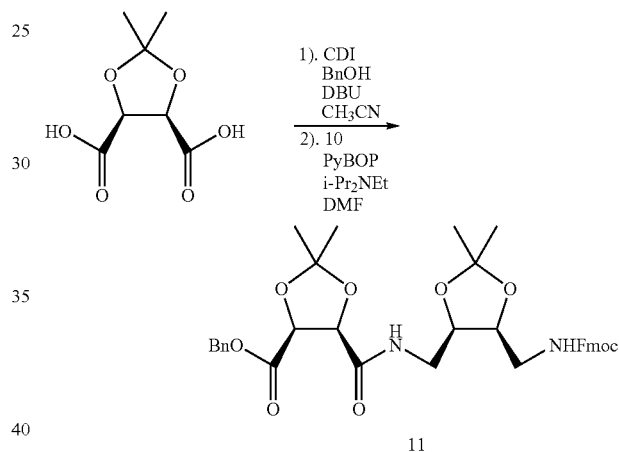

2,2-Dimethyl-[1,3]dioxolan-4R,5R-dicarboxylic acid (740 mg, 3.89 mmol) was dissolved in 50 ml of acetonitrile, 1,1'-carbonyldiimidazole (CDI; 1.26 g, 7.78 mmol) was added, and this was followed by stirring at room temperature for 30 minutes. To the reaction system, benzyl alcohol (BnOH; 420 mg, 3.89 mmol) and 1,8-diazabicyclo[5.4.0]undeca-7-ene (DBU; 887 mg, 5.84 mmol) were added; this was followed by stirring at room temperature for 17 hours. After completion of the reaction, water was added to the reaction solution, and the solution was rendered weakly acidic by further adding 1N hydrochloric acid. The reaction solution was extracted with ethyl acetate, and the organic phase extracted was washed with saturated brine, after which it was dried with anhydrous magnesium sulfate. The organic phase obtained was concentrated under reduced pressure to yield the desired monobenzyl ester compound. The monobenzyl ester compound obtained, without purification, was dissolved in 100 ml of DMF, and the Compound 10 obtained in Production Example 19 (1.2 g, 3.14 mmol) was dissolved in 10 ml of DMF and added to the reaction system. Benzotriazol-1-yl-oxy-tris-pyrolidino-phosphonium hexafluorophosphate (PyBOP; 3.37 g, 6.48 mmol) and diisopropylethylamine (i-Pr$_2$NEt; 1.25 g, 9.74 mmol) were added, and this was followed by stirring at room temperature for 17 hours. To the reaction solution, 100 ml of water was added; extraction with 100 ml of ethyl acetate was conducted three times. The organic phase extracted was washed with saturated brine, and the organic phase obtained was dried with anhydrous magnesium sulfate, after which it was concentrated under reduced pressure. The residue obtained was purified by silica gel column chromatography to yield the desired Compound 11 (0.49 g) at a percent yield of 23.5%.

MS (m/z): 645 (MH$^+$), $^1$H-NMR(CDCl$_3$) δ: 1.33-1.39 (m, 6H), 1.43 (s, 3H), 1.50 (m, 3H), 3.42 (b, 2H), 3.53 (b, 2H), 3.75 (m, 1H), 4.21 (m, 1H), 4.37-4.48 (m, 2H), 4.76-4.82 (m, 2H), 5.25 (s, 2H), 5.29 (m, 1H), 6.93 (m, 1H), 7.28-7.41 (m, 9H), 7.59 (d, 2H, J=7.5 Hz), 7.75 (d, 2H, J=7.5 Hz).

Production Example 21

Synthesis (2-3) of Hydrophilic Spacer Molecule

Synthesis of N-[4-(9H-fluoren-9-ylmethoxycarbonylamino)-2S,3S-dihydroxy-butyl]-2R,3R-dihydroxysuccinamic acid benzyl ester (Compound 12)

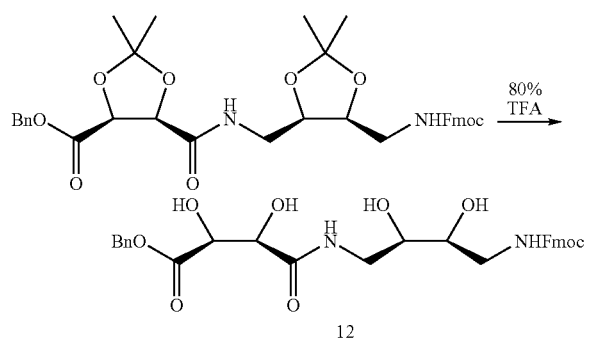

Compound 11 (0.46 g, 0.71 mmol) was dissolved in 10 ml of 80% aqueous trifluoroacetic acid (TFA), and this was followed by stirring at room temperature for 5 hours. After completion of the reaction, the solvent was evaporated, and the residue was azeotropically boiled with dichloromethane three times. The residue was dissolved in ethyl acetate, and the organic phase was washed with saturated brine. The organic phase was dried with anhydrous magnesium sulfate and concentrated under reduced pressure. Recrystallization with n-hexane-ethyl acetate was conducted to yield the desired Compound 12 (220 mg) at a percent yield of 55%.

MS (m/z): 565 (MH$^+$), $^1$H-NMR (DMSO d$_6$) δ: 2.99-3.06 (m, 2H) 3.09-3.19 (m, 2H), 3.44 (m, 2H), 4.18-4.23 (m, 1H), 4.26-4.27 (m, 3H), 4.47 (d, 1H), 4.63 (dd, 2H), 5.15 (dd, 2H), 5.40 (d, 1H), 5.88 (t, 1H), 7.14 (m, 1H), 7.28-7.42 (m, 10H), 7.64 (m, 1H), 7.70 (d, 2H), 7.88 (d, 2H).

Production Example 22

Synthesis (2-4) of Hydrophilic Spacer Molecule

Synthesis of N-[4-(9H-fluoren-9-ylmethoxycarbonylamino)-2S,3S-dihydroxy-butyl]-2R,3R-dihydroxysuccinamic acid (Compound 13)

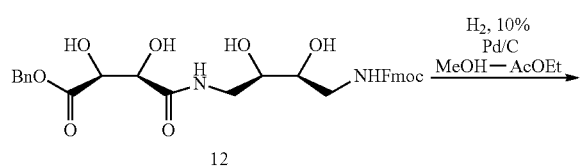

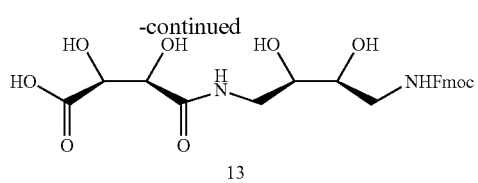

Compound 12 (200 mg, 0.35 mmol) was dissolved in 100 ml of a mixed solvent of methanol-ethyl acetate (1:1), 50 mg of 10% Pd/C (50% hydrated) was added, and this was followed by stirring in a hydrogen stream at room temperature for 2 hours. After completion of the reaction, the Pd/C was collected by filtration, and the reaction product was washed with methanol three times. The organic phase obtained was concentrated under reduced pressure to yield the desired Compound 13 (165 mg) quantitatively.

MS (m/z): 475 (MH$^+$), $^1$H-NMR(ACETON d$_6$) δ: 3.2-3.4 (m, 3H), 3.49-3.70 (m, 3H), 4.23 (m, 1H), 4.33-4.35 (m, 2H), 4.46 (m, 1H), 4.60 (m, 1H), 6.50(m, 1H), 7.33 (t, 2H), 7.41 (t, 2H), 7.68 (m, 1H), 7.71 (d, 2H), 7.86 (d, 2H).

Production Example 23

Synthesis of Resin with Hydrophilic Spacer: Synthesis of TOYO-Pearl Resin with Dihydroxyaminobutyltartaric Acid Derivative

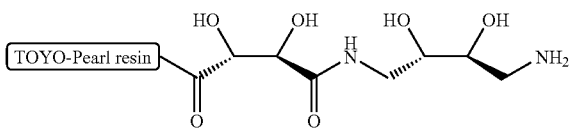

To TOYO-Pearl resin (TSKgel AF-amino; 0.01 mmol amine is present in 100 μl), dichloromethane (0.4 ml) and N-methyl-2-pyrrolidone (NMP; 0.1 ml) were added; N-[4-(9H-fluoren-9-ylmethoxycarbonylamino)-2R,3R-dihydroxy-butyl]-2R,3R-dihydroxy-succinamic acid (40 mg, 0.08 mmol), benzotriazol-1-yl-oxy-tris-pyrolidino-phosphonium hexafluorophosphate (PyBOP; 50 mg, 0.096 mmol) and N,N-diisopropylethylamine (25 mg, 0.192 mmol) were further added, and this was followed by shaking at room temperature for 2 hours. After completion of the reaction, the resin was thoroughly washed with methylene chloride and DMF, after which a percent condensation yield of 73.4% was confirmed by the ninhydrin test. To the resin obtained, a mixed solution of acetic anhydride/methanol/dichloromethane (1/1/10) (1 ml) was added, and this was followed by shaking at room temperature for 0.5 hours. The resin was thoroughly washed with methylene chloride and DMF, after which a mixed solution of piperidine/DMF/methylene chloride (1/4/4) (0.5 ml) was added, and this was followed by shaking at room temperature for 3 hours. After completion of the reaction, the resin was thoroughly washed with methylene chloride and DMF to yield the desired TOYO-Pearl resin with dihydroxyaminobutyltartaric acid derivative [TOYO+(DABT)$_1$].

Production Example 24

Synthesis of Resin with FK506-Derivative-Bound Hydrophilic Spacer (TOYO+(DABT)$_1$–FK506)

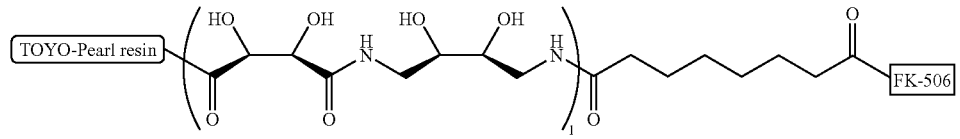

From the TOYO-Pearl resin with dihydroxyaminobutyltartaric acid derivative [TOYO+(DABT)$_1$] obtained in Production Example 23, an FK506-bound resin having a hydrophilic spacer [TOYO+(DABT)$_1$–FK506] was synthesized in accordance with the method described in Production Example 3. In the hydrophilic spacer portion that interlies between the TOYO-Pearl resin and FK506, the number of HBA is 12 and the number of HBD is 9. Note that without considering the number of HBA and the number of HBD coming from the linker of the TOYO-Pearl resin, the number of HBA is 8 and the number of HBD is 6 in the hydrophilic spacer.

Production Example 25

Synthesis of Resin with FK506-Derivative-Bound Hydrophilic Spacer (TOYO+(DABT)$_2$–FK506)

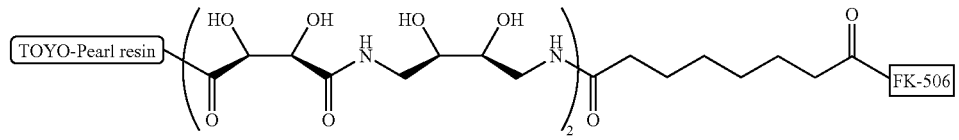

From the TOYO-Pearl resin with dihydroxyaminobutyltartaric acid derivative [TOYO+(DABT)$_1$] obtained in Production Example 23, a hydrophilic spacer elongation reaction was conducted according to Production Example 23. However, as the reaction solvent, a mixed solvent of methylene chloride (0.5 ml) and N-methyl-2-pyrrolidone (NMP; 0.05 ml) was used. Next, an FK506-bound resin having a hydrophilic spacer [TOYO+(DABT)$_2$–FK506] was synthesized in accordance with the method described in Production Example 3. In the hydrophilic spacer portion that interlies between the TOYO-Pearl resin and FK506, the number of HBA is 20 and the number of HBD is 15. Note that without considering the number of HBA and the number of HBD coming from the linker of the TOYO-Pearl resin, the number of HBA is 16 and the number of HBD is 12 in the hydrophilic spacer.

Production Example 26

Synthesis (3-1) of Hydrophilic Spacer Molecule

Synthesis of N-[2-(9H-fluoren-9-ylmethoxycarbonylamino)-ethyl]-2,3-dihydroxy-succinamic acid (Compound 16)

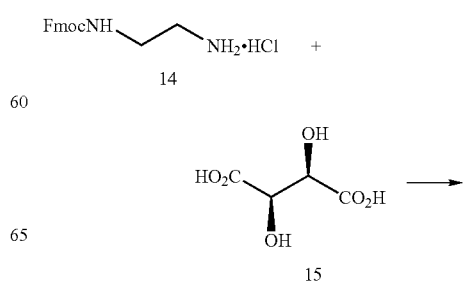

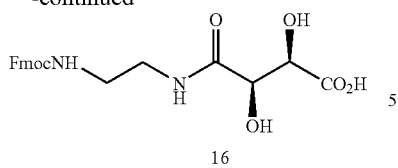

16

9H-9-fluorenylmethyl N-(2-aminoethyl)carbamate hydrochloride (Compound 14; 5.00 g, 153.7 mmol) and L-(+)-tartaric acid (Compound 15; 5.89 g, 39.2 mmol) were dissolved by the addition of N,N-dimethylformamide (300 ml) and triethylamine (5.46 ml, 39.2 mmol). Next, 1-hydroxybenzotriazol hydrate (2.52 g, 16.5 mmol) was added, a solution of 1-ethyl-3-(3-dimethylaminopropyl)carbodiimide hydrochloride (3.16 g, 16.5 mmol) in N,N-dimethylformamide (200 ml) was added drop by drop, and this was followed by overnight stirring at room temperature. This was concentrated under reduced pressure, the residue obtained was dissolved in ethyl acetate, and the organic phase was washed with a 2N aqueous solution of citric acid. Next, reverse extraction was conducted using aqueous sodium hydrogen carbonate, after which the water phase obtained was washed with ethyl acetate. Under ice cooling, the water phase was rendered acidic with a 2N aqueous solution of citric acid, after which it was extracted with ethyl acetate. The organic phase was washed with saturated brine, after which it was dried with sodium sulfate. After the solid was filtered and concentrated under reduced pressure, crystallization from methanol-diethyl ether was conducted to yield the desired N-[2-(9H-fluoren-9-ylmethoxycarbonylamino)-ethyl]-2,3-dihydroxy-succinamic acid (2.72 g, 42%).

$^1$H-NMR(d-acetone) δ: 3.29 (2H, t), 3.37 (2H, t), 4.24 (1H, m), 4.30 (2H, m), 4.41 (1H, d), 4.59 (1H, d), 7.29-7.42 (4H, m), 7.68 (2H, d), 7.85 (2H, d). MS(m/z): 415.2 (M+).

Production Example 27

Synthesis of Resin with Hydrophilic Spacer: Synthesis of TOYO-Pearl Resin with Aminoethyltartaric Diamide Derivative

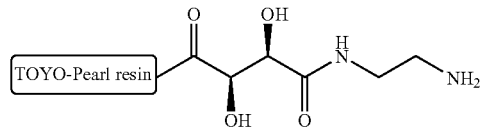

To TOYO-Pearl resin (TSKgel AF-amino; 0.01 mmol amine is present in 100 µl), methylene chloride (0.5 ml) was added; the Compound 16 obtained in Production Example 26 (16.6 mg, 40 µmol), N,N-diisopropylethylamine (16.7 µl, 96 µmol) and PyBOP (25.0 mg, 48 µmol) were further added, and this was followed by overnight shaking at room temperature. After completion of the reaction, the resin was thoroughly washed with methylene chloride and DMF, after which a mixed solution of acetic anhydride/methanol/methylene chloride (1/1/10) (1.5 ml) was added to the resin obtained, and this was followed by shaking at room temperature for 25 minutes. After completion of the reaction, the resin was thoroughly washed with methylene chloride and DMF, after which a 20% piperidine/DMF solution (0.5 ml) was added, and this was followed by shaking at room temperature 10 minutes. Next, the resin was washed with DMF, after which a 20% piperidine/DMF solution (0.5 ml) was again added, and this was followed by shaking at room temperature for 20 minutes. After completion of the reaction, the resin was thoroughly washed with methylene chloride and DMF to yield a TOYO-Pearl resin with aminoethyltartaric diamide derivative [TOYO+(AET)$_1$].

Production Example 28

Synthesis of Resin with FK506-Derivative-Bound Hydrophilic Spacer (TOYO+(AET)$_1$–FK506)

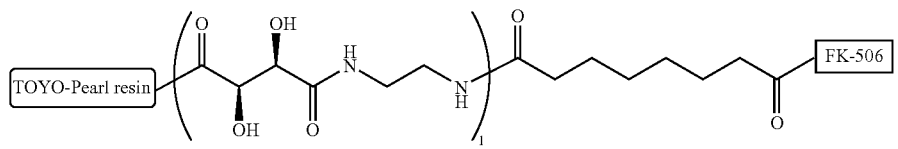

From the TOYO-Pearl resin with aminoethyltartaric diamide derivative obtained in Production Example 27 [TOYO+(AET)$_1$], an FK506-bound resin having a hydrophilic spacer [TOYO+(AET)$_1$–FK506] was synthesized in accordance with the method described in Production Example 3. In the hydrophilic spacer portion that interlies between the TOYO-Pearl resin and FK506, the number of HBA is 10 and the number of HBD is 7. Note that without considering the number of HBA and the number of HBD derived from the linker of the TOYO-Pearl resin, the number of HBA is 6 and the number of HBD is 4 in the hydrophilic spacer.

Production Example 29

Synthesis of Resin with FK506-Derivative-Bound Hydrophilic Spacer (TOYO+(AET)$_2$–FK506)

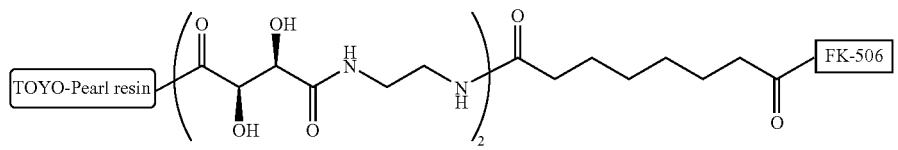

From the TOYO-Pearl resin with aminoethyl tartaric diamide derivative [TOYO+(AET)₁] obtained in Production Example 27, a hydrophilic spacer elongation reaction was conducted according to Production Example 27. However, as the reaction solvent, a mixed solvent of methylene chloride (0.5 ml) and N-methyl-2-pyrrolidone (NMP; 0.05 ml) was used. Next, an FK506-bound resin having a hydrophilic spacer [TOYO+(AET)₂–FK506] was synthesized in accordance with the method described in Production Example 3. In the hydrophilic spacer portion that interlies between the TOYO-Pearl resin and FK506, the number of HBA is 16 and the number of HBD is 11. Note that without considering the number of HBA and the number of HBD coming from the linker of the TOYO-Pearl resin, the number of HBA is 12 and the number of HBD is 8 in the hydrophilic spacer.

Production Example 30

Synthesis (4-1) of Hydrophilic Spacer Molecule

Synthesis of 4-tert-butyldimethylsilyloxyphenol (Compound 18)

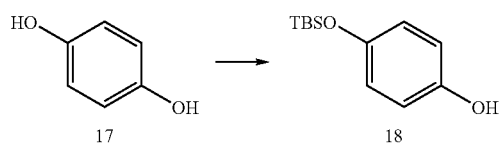

To an ice-cooled solution of hydroquinone (Compound 17; 3.3 g, 30 mmol) in DMF (60 ml), a solution of imidazole (3.1 g, 45 mmol) and tert-butyldimethylsilyl chloride (4.5 g, 30 mmol) in DMF (30 ml) was added; the ice bath was removed, and this was followed by overnight stirring at room temperature. This was poured over water to stop the reaction, after which extraction from ether was conducted. The combined organic phases were washed with saturated brine, thereafter dried with sodium sulfate. After filtration and concentration under reduced pressure, the residue obtained was purified by silica gel column chromatography [Biotage, eluent (9:1 n-hexane:ethyl acetate)] to yield Compound 18 (white solid 3.6 g, 53%).

MS(m/z): 225 (MH⁺), ¹H-NMR(CDCl₃) δ: 0.16 (6H, s), 0.97 (9H, s), 4.43 (1H, s), 6.70 (4H, d, J=2 Hz).

Production Example 31

Synthesis (4-2) of Hydrophilic Spacer Molecule

Synthesis of [2-(2-{2-[2-(2-benzyloxy-ethoxy)-ethoxy]-ethoxy}-ethoxy)]ethanol (Compound 19)

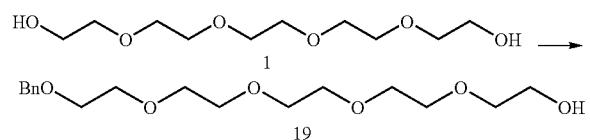

To Compound 1 (5.2 g, 21.8 mmol), potassium hydroxide (1.2 g, 21.4 mmol) was added; this was followed by stirring on an oil bath at 130° C. for 15 minutes, after which the oil bath was removed and benzyl chloride (2.7 g, 21.3 mmol) was gradually added. This was again heated to 130° C. and stirred for 2 hours. After the solution was allowed to cool to room temperature, water was poured to stop the reaction, and extraction from methylene chloride was conducted. The combined organic phases were dried with sodium sulfate, filtered, and concentrated under reduced pressure, after which the residue obtained was purified by silica gel column chromatography (Yamazen YFLC Gel, eluent (ethyl acetate—5% methanol-ethyl acetate solution) to yield Compound 19 (light-yellow oil 2.3 g, 32%).

MS(m/z): 329 (MH⁺), ¹H-NMR(CDCl₃) δ: 3.34 (2H, t), 3.76-3.84 (20H, m), 4.13 (2H, s), 7.26-7.35 (5H, m).

Production Example 32

Synthesis (4-3) of Hydrophilic Spacer Molecule

Synthesis of [2-(2-{2-[2-(2-bromo-ethoxy)-ethoxy]-ethoxy}-ethoxy)-ethoxymethyl]benzene (Compound 20)

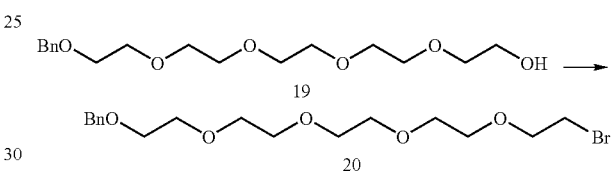

To a solution of Compound 19 (2.04 g, 6.21 mmol) in methylene chloride (20 ml), a solution of carbon tetrabromide (4.12 g, 12.4 mmol) in methylene chloride (10 ml) was added at room temperature; after cooling with ice, triphenylphosphine (2.51 g, 12.4 mmol) was added. The water bath was removed, and this was followed by stirring at room temperature for 1 hour. After concentration under reduced pressure, the residue obtained was purified by silica gel column chromatography (Yamazen YFLC Gel, eluent (n-hexane:ethyl acetate 2:1-1:1)) to yield Compound 20 (light-yellow oil 2.14 g, 88%).

MS(m/z): 391 (MH⁺), ¹H-NMR(CDCl₃) δ: 3.46 (2H, t, J=6.4 Hz) 3.62-3.69 (m, 16H), 3.62-3.72 (20H, m), 3.80 (2H, t, J=6.4 Hz), 4.57(2H, s), 7.26-7.35 (5H, m).

Production Example 33

Synthesis (4-4) of Hydrophilic Spacer Molecule

Synthesis of tert-butyl-dimethyl-{4-[2-(2-{2-[2-(2-trityloxy-ethoxy)-ethoxy]-ethoxy}-ethoxy)-ethoxy]-phenoxy}silane (Compound 21)

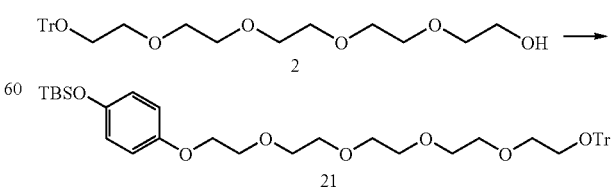

To a solution of Compound 2 (2.8 g, 5.8 mmol) in toluene (10 ml), a solution of tributylphosphine (1.17 g, 5.8 mmol) in toluene (2 ml) was added at room temperature; this was followed by stirring for 1 hour. This was gradually added to a solution of Compound 18 (1.1 g, 4.9 mmol) and 1,1'-azobis (N,N-dimethylformamide) (1.0 g, 5.8 mmol) in toluene (10 ml), and this was followed by overnight stirring at room temperature. Ethyl acetate was added; the resulting insoluble matter was removed by Celite filtration, and washing was conducted with ethyl acetate. The combined organic phases were concentrated under reduced pressure; the residue obtained was purified by silica gel column chromatography (Yamazen YFLC Gel, eluent (n-hexane:ethyl acetate 2:1)) to yield Compound 21 (colorless oil 2.03 g, 60%).

$^1$H-NMR(CDCl$_3$) δ: 0.16(6H, s), 0.97(9H, s), 3.23 (2H, t, J=5 Hz), 3.64-3.69(14H, m), 3.80 (2H, t, J=5 Hz), 4.04 (2H, t, J=5 Hz), 6.69-6.75 (5H, m), 7.23-7.30 (13H, m), 7.45-7.47 (6H, m).

Production Example 34

Synthesis (4-5) of Hydrophilic Spacer Molecule

Synthesis of 4-[2-(2-{2-[2-(2-trityloxy-ethoxy)-ethoxy]-ethoxy}-ethoxy)-ethoxy]phenol (Compound 22)

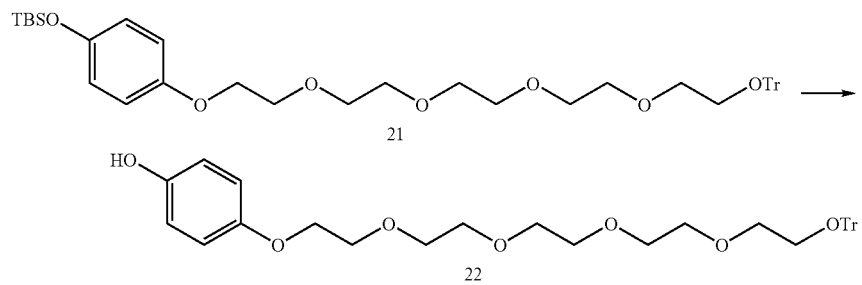

To an ice-cooled solution of Compound 21 (1.88 g, 2.74 mmol) in THF (20 ml), a solution of 1M tetrabutylammonium fluoride in THF (4 ml) was added. After completion of the addition, the ice bath was removed, and this was followed by stirring at room temperature for 10 minutes. This was poured over water to stop the reaction, after which extraction from ethyl acetate was conducted. The organic phases were combined, washed with saturated brine, thereafter dried with anhydrous sodium sulfate. After filtration and concentration under reduced pressure, the residue obtained was purified by silica gel column chromatography (Yamazen YFLC Gel, eluent (n-hexane:ethyl acetate 2:1-1:1)) to yield Compound 22 (light-yellow oil 1.45 g, 92%).

$^1$H-NMR(CDCl$_3$) δ: 3.23 (2H, t, J=5 Hz), 3.64-3.69 (m, 14H), 3.79 (2H, t, J=5 Hz), 4.04 (2H, t, J=5 Hz), 4.68 (1H, s), 6.71-6.79 (4H, m), 7.20-7.30 (9H, m), 7.45-7.47 (6H, m).

Production Example 35

Synthesis (4-6) of Hydrophilic Spacer Molecule

Synthesis of 1-[2-(2-{2-[2-(2-benzyloxy-ethoxy)-ethoxy]-ethoxy}-ethoxy)-ethoxy]-4-[2-(2-{2-[2-(2-trityloxy-ethoxy)-ethoxy]-ethoxy}-ethoxy)-ethoxy]benzene (Compound 23)

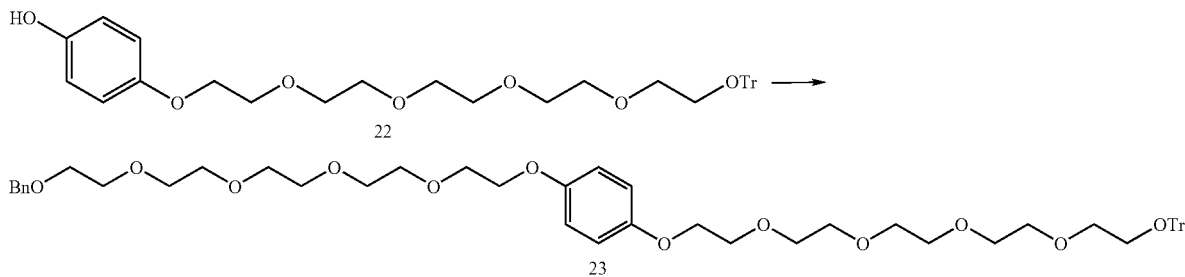

To an ice-cooled suspension of sodium hydride (800 mg, 20 mmol; 60% in mineral oil) in THF (15 ml), a solution of Compound 22 (1.2 g, 2.1 mmol) in THF (20 ml) was gradually added; this was followed by stirring for 20 minutes. A solution of Compound 20 (1.7 g, 4.3 mmol) in THF (12 ml) was added thereto, and this was followed by stirring for 20 minutes. After the ice bath was removed, stirring was further conducted at room temperature for 2 hours. Water was carefully added to stop the reaction, and this was followed by concentration under reduced pressure. Extraction from methylene chloride was conducted, and the combined organic phases were washed with saturated brine and dried with anhydrous sodium sulfate. After filtration and concentration under reduced pressure, the residue obtained was purified by silica gel column chromatography (Yamazen YFLC Gel, eluent (n-hexane:ethyl acetate 2:1-1:1)) to yield Compound 23 (light-yellow oil 1.56 g, 84%).

$^1$H-NMR(CDCl$_3$) δ: 3.23 (2H, t, J=5 Hz), 3.61-3.72 (30H, m), 3.78-3.82 (4H, m), 4.03-4.07 (4H, m), 4.56 (2H, s), 6.82 (4H, s), 4.12 (1H, t), 7.09-7.34 (14H, m), 7.44-7.47 (6H, m).

Production Example 36

Synthesis (4-7) of Hydrophilic Spacer Molecule

Synthesis of 2-(2-{2-[2-(2-{4-[2-(2-{2-[2-(2-benzyloxy-ethoxy)-ethoxy]-ethoxy}-ethoxy)-ethoxy]-phenoxy}-ethoxy)-ethoxy]-ethoxy}-ethoxy)ethanol (Compound 24)

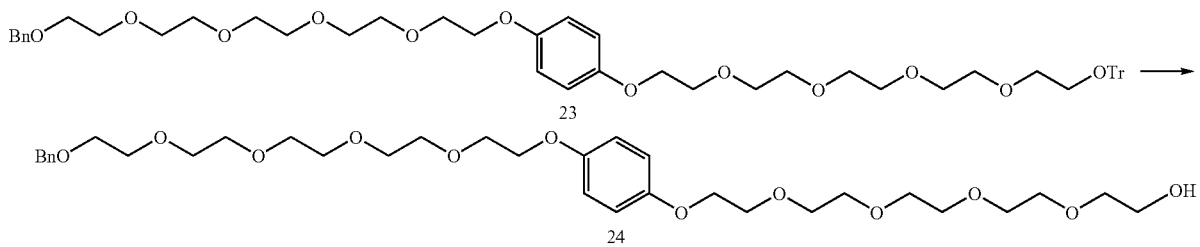

To an ice-cooled solution of Compound 23 (1.43 g, 1.62 mmol) in methylene chloride (20 ml), a methylene chloride solution containing 10% trifluoroacetic acid (10 ml) was added; water (1 ml) was added thereto, after which the ice bath was removed, and this was followed by stirring at room temperature for 2 hours and 30 minutes. The reaction solution was poured over a saturated aqueous solution of sodium hydrogen carbonate to stop the reaction, after which extraction from methylene chloride and chloroform was conducted. The combined organic phases were dried with sodium sulfate, filtered, and concentrated under reduced pressure, after which the residue obtained was subjected to silica gel column chromatography (Yamazen YFLC Gel, eluent (ethyl acetate containing 10% methanol)) to yield Compound 24 (light-yellow oil 875 mg, 85%).

MS(m/z): 641 (MH$^+$), $^1$H-NMR(CDCl$_3$) δ: 3.59-3.74 (32H, m), 3.80-3.84 (4H, m), 4.05-4.08 (4H, m), 4.56 (2H, s), 6.83 (4H, s), 7.26-7.34 (5H, m).

Production Example 37

Synthesis (4-8) of Hydrophilic Spacer Molecule

Synthesis of [2-(2-{2-[2-(2-{4-[2-(2-{2-[2-(2-benzyloxy-ethoxy)-ethoxy]-ethoxy}-ethoxy)-ethoxy]-phenoxy}-ethoxy)-ethoxy]-ethoxy}-ethoxy)-ethoxy] acetic acid tert-butyl ester (Compound 25)

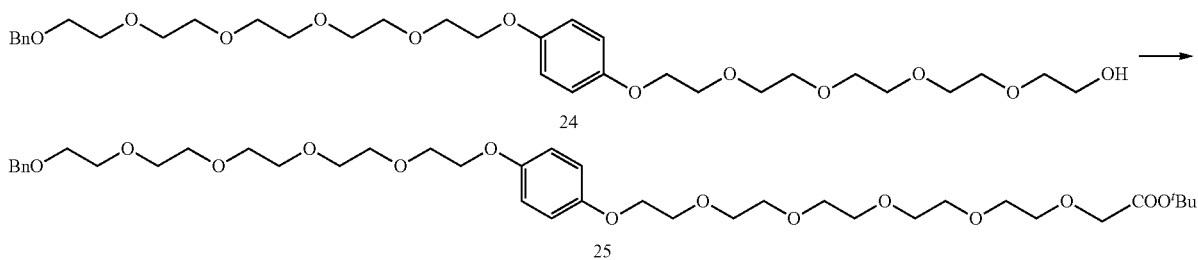

To an ice-cooled suspension of sodium hydride (180 mg, 4.5 mmol; 60% in mineral oil) in THF/DMF (5/1 mixed solution 7 ml), a solution of Compound 24 (817 mg, 1.28 mmol) in THF (6 ml) was gradually added; this was followed by stirring for 30 minutes. A solution of bromoacetic acid tert-butyl ester (1.0 g, 5.1 mmol) in THF (7 ml) was added thereto. After the ice bath was removed, stirring was further conducted at room temperature for 2 hours. Water was carefully added to stop the reaction, this was followed by extraction from ethyl acetate, and the combined organic phases were washed with saturated brine and dried with anhydrous sodium sulfate. After filtration and concentration under reduced pressure, the residue obtained was purified by silica gel column chromatography (Yamazen YFLC Gel, eluent (ethyl acetate-ethyl acetate solution containing 5% methanol)) to yield Compound 25 (light-yellow oil 655 mg, 68%).

$^1$H-NMR(CDCl$_3$) δ: 1.47 (9H, s), 3.61-3.73 (30H, m), 3.81-3.84 (4H, m), 4.02 (2H, s), 4.05-4.08 (4H, m), 4.56(2H, s), 6.83(4H, s), 7.26-7.24(5H, m).

Production Example 38

Synthesis (4-9) of Hydrophilic Spacer Molecule

Synthesis of [2-(2-{2-[2-(2-{4-[2-(2-{2-[2-(2-hydroxy-ethoxy)-ethoxy]-ethoxy}-ethoxy)-ethoxy]-phenoxy}-ethoxy)-ethoxy]-ethoxy}-ethoxy)-ethoxy] acetic acid tert-butyl ester (Compound 26)

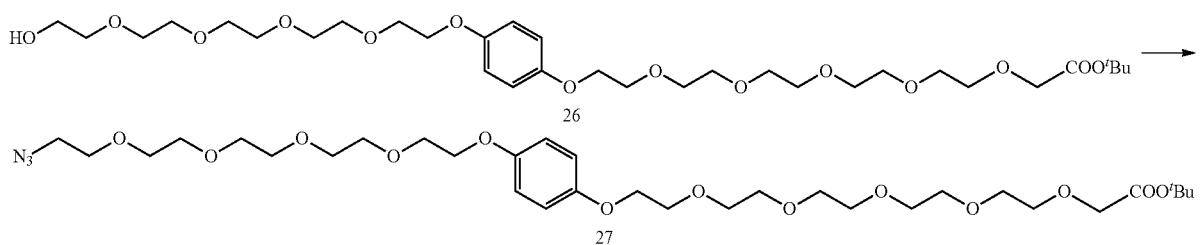

In a nitrogen atmosphere, to a suspension of palladium hydroxide (20% by weight; 145 mg) in methanol (4 ml), a solution of Compound 25 (655 mg, 0.868 mmol) in methanol (6 ml) was added; after the nitrogen atmosphere was replaced with a hydrogen atmosphere, stirring was conducted at room temperature for 4 hours. After a nitrogen atmosphere was restored, ethyl acetate (about 10 ml) was added, and this was followed by filtration on silica gel and washing with an ethyl acetate solution containing 10% methanol. Concentration under reduced pressure was conducted to yield a crude product of Compound 26.

$^1$H-NMR(CDCl$_3$) δ: 1.47 (9H, s), 3.59-3.84 (36H, m), 3.81-3.84 (4H, m), 4.02 (2H, s), 4.07-4.09 (4H, m), 6.84(4H, s).

Production Example 39

Synthesis (4-10) of Hydrophilic Spacer Molecule

Synthesis of [2-(2-{2-[2-(2-{4-[2-(2-{2-[2-(2-azido-ethoxy)-ethoxy]-ethoxy}-ethoxy)-ethoxy]-phenoxy}-ethoxy)-ethoxy]-ethoxy}-ethoxy)-ethoxy] acetic acid tert-butyl ester (Compound 27)

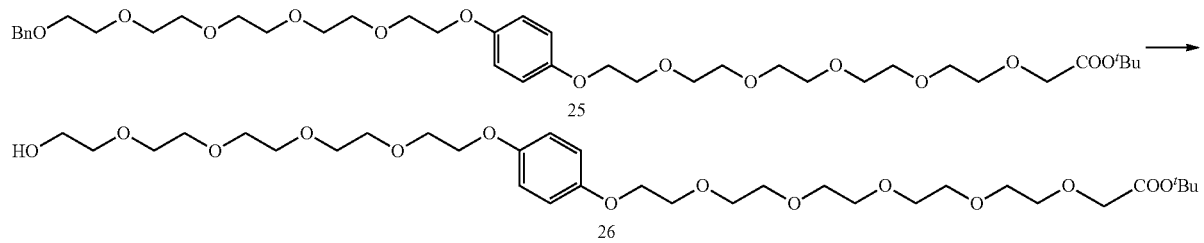

To a solution of Compound 26 (254 mg, 0.451 mmol) in pyridine (1.5 ml), 4-dimethylaminopyridine (11 mg, 0.09 mmol) was added; after cooling with ice, p-toluenesulfonyl chloride (130 mg, 0.677 mmol) was added, and this was followed by stirring for 2 hours while heating to 30° C.-40° C. Ice was added thereto to stop the reaction, after which ethyl acetate and water were added. Extraction from ethyl acetate was conducted, and the combined organic phases were washed with a saturated aqueous solution of potassium hydrogen sulfate, a saturated aqueous solution of sodium hydrogen carbonate and saturated brine, and dried with sodium sulfate. Filtration and concentration under reduced pressure were conducted to yield a crude product. The crude product obtained was dissolved in DMF (1 ml), and sodium azide (264 mg, 4.1 mmol) was added thereto. The solution was heated to about 60° C., and this was followed by stirring for 90 minutes. The solution was allowed to cool to room temperature, after which it was diluted with ethyl acetate. After a saturated aqueous solution of sodium hydrogen carbonate was further added, extraction from ethyl acetate was conducted. The combined organic phases were washed with saturated brine, thereafter dried with sodium sulfate. Filtration and concentration under reduced pressure were conducted, after which the concentrate was purified by silica gel column chromatography (Yamazen YFLC Gel, eluent; ethyl acetate solution containing 10% methanol) to yield Compound 27 (colorless oil 196 mg, 73%, 2 steps).

$^1$H-NMR(CDCl$_3$) δ: 1.47 (9H, s), 3.38 (2H, t, J=5 Hz), 3.66-3.72 (30H, m), 3.81-3.84 (4H, m), 4.02 (2H, s), 4.06-4.08 (4H, m), 6.84 (4H, s).

Production Example 40

Synthesis (4-11) of Hydrophilic Spacer Molecule

Synthesis of [2-(2-{2-[2-(2-{4-[2-(2-{2-[2-(2-amino-ethoxy)-ethoxy]-ethoxy}-ethoxy)-ethoxy]-phenoxy}-ethoxy)-ethoxy]-ethoxy}-ethoxy)-ethoxy] acetic acid tert-butyl ester (Compound 28)

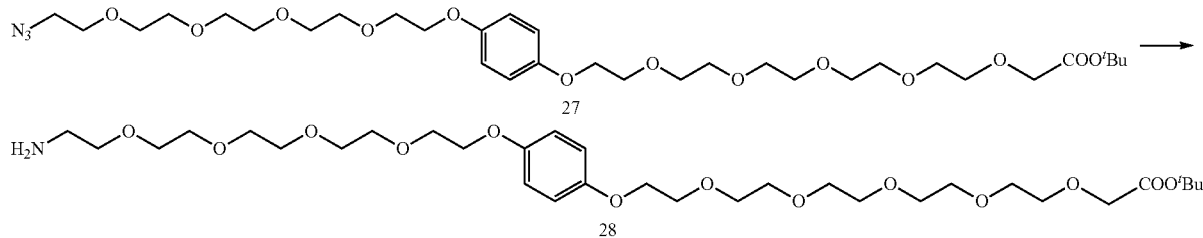

In a nitrogen atmosphere, to a suspension of palladium hydroxide (20% by weight; 18 mg) in methanol (1 ml), a solution of Compound 27 (190 mg, 0.323 mmol) in methanol (1.5 ml) was added; after the nitrogen atmosphere was replaced with a hydrogen atmosphere, stirring was conducted at room temperature for 1 hour. After a nitrogen atmosphere was restored, insoluble matter was separated by filtration on Celite and washed with methanol. Concentration under reduced pressure was conducted to yield a crude product of Compound 28.
MS(m/z): 664 (MH$^+$).

Production Example 41

Synthesis (4-12) of Hydrophilic Spacer Molecule

Synthesis of {2-[2-(2-{2-[2-(4-{2-[2-(2-{2-[2-(9H-fluoren-9-yl-methoxycarbonylamino)-ethoxy]-ethoxy}-ethoxy)-ethoxy]-ethoxy}-phenoxy)-ethoxy]-ethoxy}-ethoxy)-ethoxy]-ethoxy}acetic acid tert-butyl ester (Compound 29)

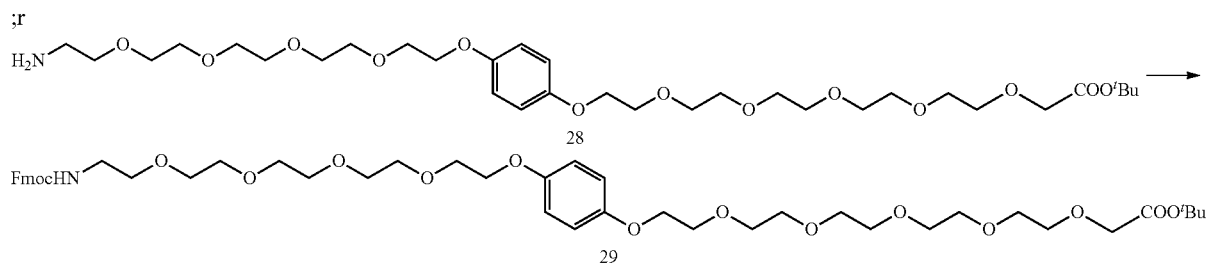

A solution of the crude product of Compound 28 obtained in Production Example 40 (175 mg, 0.311 mmol) in THF (1.2 ml) was cooled with ice, a solution of 9-fluorenylmethylsuccinimidyl carbonate (115 mg, 0.34 mmol) in THF (0.5 ml) was added thereto, triethylamine (62 mg, 0.62 mmol, 85 µl) was further added, and this was followed by stirring for 45 minutes. Water was added thereto to stop the reaction, after which extraction from ethyl acetate was conducted, and the combined organic phases were washed with saturated brine and dried with sodium sulfate. Filtration and concentration under reduced pressure were conducted, after which the concentrate was purified by silica gel column chromatography (Yamazen YFLC Gel, eluent; ethyl acetate-ethyl acetate solution containing 10% methanol) to yield Compound 29 (colorless oil 196 mg, 84%).
$^1$H-NMR(CDCl$_3$) δ: 1.47 (9H, s), 3.37-3.41 (1H, m), 3.55-3.84 (36H, m), 3.66-3.72 (30H, m), 4.01 (2H, s), 4.01-4.07 (4H, m), 4.20-4.23 (1H, m), 4.40 (2H, d, J=7 Hz), 6.81 (4H, s), 7.29-7.33 (2H, m), 7.39-7.41 (2H,m), 7.60 (2H, d, J=7 Hz), 7.76 (2H, d, J=7 Hz).

Production Example 42

Synthesis (4-13) of Hydrophilic Spacer Molecule

Synthesis of {2-[2-(2-{2-[2-(4-{2-[2-(2-{2-[2-(9H-fluoren-9-yl-methoxycarbonylamino)-ethoxy]-ethoxy}-ethoxy)-ethoxy]-ethoxy}-phenoxy)-ethoxy]-ethoxy}-ethoxy)-ethoxy]-ethoxy}acetic acid (Compound 30)

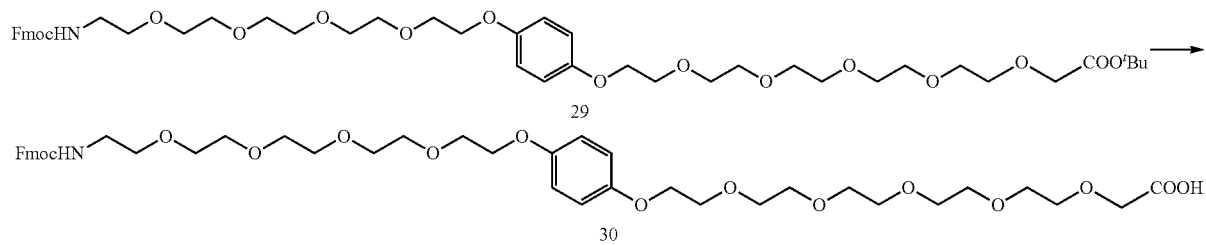

To Compound 29 (196 mg, 0.25 mmol), 5% hydrated trifluoroacetic acid (1.5 ml) was added at room temperature; this was followed by stirring for 5 minutes. Toluene (about 1 ml) was added; after concentration under reduced pressure, the concentrate was purified by silica gel column chromatography (Yamazen YFLC Gel, eluent; chloroform containing 3% methanol-ethyl acetate solution containing 10% methanol) to yield Compound 30 (colorless oil 175 mg, 96%).

MS(m/z): 830 (MH$^+$), $^1$H-NMR(CDCl$_3$) δ: 1.47 (9H, s), 3.37-3.39 (1H, m), 3.56-3.84 (36H, m), 4.02-4.07 (4H, m), 4.12 (2H, s), 4.22-4.23 (1H, m), 4.40 (2H, d, J=7 Hz), 6.81 (4H, s), 7.29-7.33 (2H, m), 7.38-7.41 (2H,m), 7.60 (2H, d, J=7 Hz), 7.76 (2H, d, J=7 Hz).

Production Example 43

Synthesis of Resin with Hydrophilic Spacer: Synthesis of TOYO-Pearl Resin (TSKgel AF-Amino) with Compound 30 Derivative To TOYO-Pearl resin (TSKgel AF-amino; 0.01 mmol amine is present in 100 μl), methylene chloride (0.4 ml) and {2-[2-(2-{2-[2-(4-{2-[2-(2-{2-[2-(9H-fluoren-9-yl-methoxycarbonylamino)-ethoxy]-ethoxy}-ethoxy)-ethoxy]-ethoxy}-phenoxy)-ethoxy]-ethoxy}-ethoxy)-ethoxy]-ethoxy}acetic acid (66 mg, 0.08 mmol) were added; benzotriazol-1-yl-oxy-tris-pyrolidino-phosphonium hexafluorophosphate (PyBOP; 52 mg, 0.10 mmol) and N,N-diisopropylethylamine (34 μl, 0.20 mmol) were further added, and this was followed by shaking at room temperature for 4 hours. After completion of the reaction, the resin was thoroughly washed with methylene chloride and DMF, after which condensation was confirmed by the ninhydrin test. To the resin obtained, a mixed solution of acetic anhydride/methylene chloride/NMP (1/8/2) (1.0 ml) was added; this was followed by shaking at room temperature for 3 hours. The resin was thoroughly washed with methylene chloride and DMF, after which a mixed solution of piperidine/DMF/methylene chloride (1/4/4) (0.5 ml) was added, and this was followed by shaking at room temperature for 3 hours. After completion of the reaction, the resin was thoroughly washed with methylene chloride and DMF, after which the presence of the amine was confirmed by the ninhydrin test; hence, attachment of the hydrophilic spacer to the resin was confirmed.

Production Example 44

Synthesis of Resin with Hydrophilic Spacer: Synthesis of TOYO-Pearl Resin (TSKgel AF-Amino) with Compound 30 Derivative Dimer The resin obtained in Production Example 43 (100 μl) was reacted according to the technique of Production Example 43 to yield the desired product. This was acetylated and treated for Fmoc removal according to the technique of Production Example 43 to yield TOYO-Pearl resin with Compound 30 derivative dimer. The presence of the amine was confirmed by the ninhydrin test; hence, attachment of the hydrophilic spacer to the resin was confirmed.

Production Example 45

Synthesis (5-1) of Hydrophilic Spacer Molecule

Synthesis of 2-[[(9H-fluoren-9-ylmethoxy)carbonyl]amino]-acetamide (Compound 32)

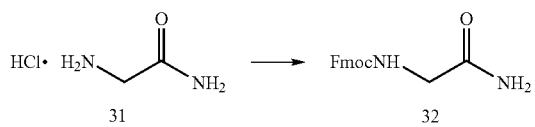

To 2-amino-acetamide hydrochloride (Compound 31, 10.0 g, 90.5 mmol), a 10% aqueous solution of sodium carbonate (600 ml) and acetone (250 ml) were added; next, under ice cooling, a solution of N-(9-fluorenylmethoxycarbonyloxy)succinimide (30.5 mg, 90.5 mmol) in acetone (250 ml) was added drop by drop. After stirring at room temperature for 1 hour, the mixture was concentrated under reduced pressure; the residue obtained was dissolved in ethyl acetate, the organic phase was sequentially washed with a 2N aqueous solution of citric acid, aqueous sodium hydrogen carbonate and saturated brine, after which it was dried with magnesium sulfate. The solid was filtered and concentrated under reduced pressure, after which crystallization from methanol was conducted to yield the desired 2-[[(9H-fluoren-9-ylmethoxy)carbonyl]amino]-acetamide (Compound 32; 27.7 g, quant).

¹H-NMR(CDCl₃) δ: 3.87 (2H, bd), 4.23 (1H, t), 4.46 (2H, d), 7.30 (2H, t), 7.39 (2H, t), 7.57 (2H, d), 7.75 (2H, d); MS (m/z); 297.2 (M⁺).

Production Example 46

Synthesis (5-2) of Hydrophilic Spacer Molecule

Synthesis of N-[(9H-fluoren-9-yl-methoxycarbonylamino)-methyl]-2,3-dihydroxy-succinamic acid (Compound 33)

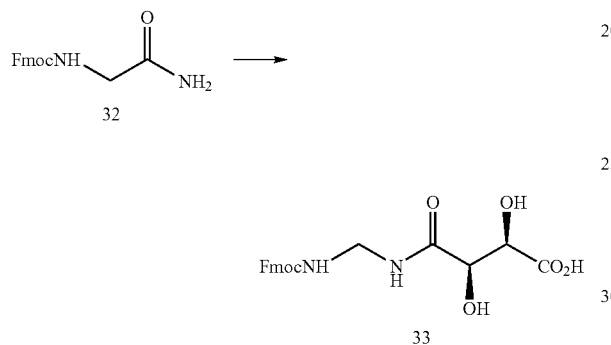

To Compound 32 (1.50 g, 5.06 mmol), ethyl acetate (15 ml), acetonitrile (15 ml), H₂O (15 ml) and [bis(trifluoroacetoxy)iodo]benzene (2.83 g, 6.58 mmol) were added; this was followed by stirring at room temperature for 1.5 hours. After reverse extraction was conducted using a 0.2N aqueous solution of hydrochloric acid, the water phase obtained was washed with a mixed solvent of diethyl ether:hexane. Under ice cooling, the water phase was rendered alkaline with saturated aqueous sodium hydrogen carbonate, after which it was extracted with chloroform. The organic phase was washed with saturated brine, after which it was dried with magnesium sulfate, and the solid was filtered and concentrated under reduced pressure. The residue obtained was dissolved by the addition of L-(+)-tartaric acid (1.42 g, 9.45 mmol) and N,N-dimethylformamide (100 ml). Next, 1-ethyl-3-(3-dimethylaminopropyl)-carbodiimide hydrochloride (795 mg, 4.15 mmol) was added, and this was followed by overnight stirring at room temperature. This was concentrated under reduced pressure, the residue obtained was dissolved in ethyl acetate, and the organic phase was washed with a 2N aqueous solution of citric acid. Next, reverse extraction was conducted using aqueous sodium hydrogen carbonate, after which the water phase obtained was washed with ethyl acetate. Under ice cooling, the water phase was rendered acidic with a 2N aqueous solution of citric acid, after which it was extracted with ethyl acetate. The organic phase was washed with saturated brine, after which it was dried with sodium sulfate. The solid was filtered and concentrated under reduced pressure, after which crystallization from methanol was conducted to yield the desired N-[(9H-fluoren-9-yl-methoxycarbonylamino)-methyl]-2,3-dihydroxy-succinamic acid (Compound 33; 588 mg, 29%).

¹H-NMR (d-acetone) δ: 4.24 (1H, t), 4.23 (2H, d), 4.44 (1H, d), 4.58-4.71 (3H, m), 7.33 (2H, t), 7.41 (2H, t), 7.71 (2H, d), 7.86 (2H, d);
MS (m/z); 401.2 (M⁺).

Production Example 47

Synthesis of Resin with Hydrophilic Spacer: Synthesis of TOYO-Pearl Resin with Aminomethyltartaric Diamide Derivative

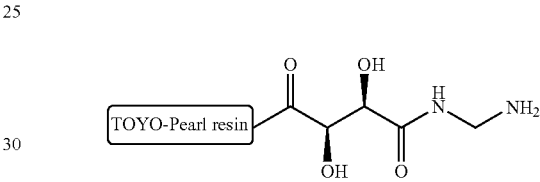

TOYO-Pearl resin (TSKgel AF-amino; 0.01 mmol amine is present in 100 μl) was reacted with Compound 33 according to the technique of Production Example 27 to yield TOYO-Pearl resin with aminomethyltartaric diamide derivative [TOYO+(AMT)₁].

Production Example 48

Synthesis of Resin with FK506-Derivative-Bound Hydrophilic Spacer (TOYO+(AMT)₁–FK506)

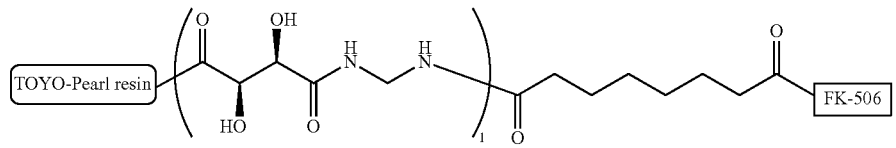

From the TOYO-Pearl resin with aminomethyltartaric diamide derivative [TOYO+(AMT)₁] obtained in Production Example 47, an FK506-bound resin having a hydrophilic spacer [TOYO+(AMT)₁–FK506] was synthesized in accordance with the method described in Production Example 3. In the hydrophilic spacer portion that interlies between the TOYO-Pearl resin and FK506, the number of HBA is 10 and the number of HBD is 7. Note that without considering the number of HBA and the number of HBD derived from the linker of the TOYO-Pearl resin, the number of HBA is 6 and the number of HBD is 4 in the hydrophilic spacer.

Production Example 49

Synthesis of Resin with FK506-Derivative-Bound Hydrophilic Spacer (TOYO+(AMT)$_2$–FK506)

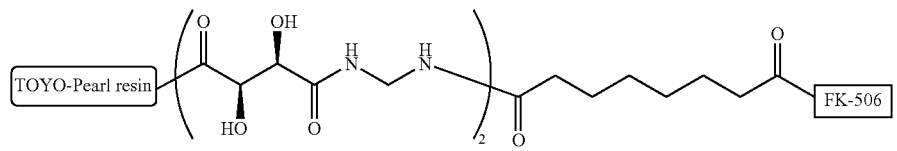

From the TOYO-Pearl resin with aminomethyltartaric diamide derivative [TOYO+(AMT)$_1$] obtained in Production Example 47, a hydrophilic spacer elongation reaction was conducted according to Production Example 47. Next, an FK506-bound resin having a hydrophilic spacer [TOYO+(AMT)$_2$–FK506] was synthesized in accordance with the method described in Production Example 3. In the hydrophilic spacer portion that interlies between the TOYO-Pearl resin and FK506, the number of HBA is 16 and the number of HBD is 11. Note that without considering the number of HBA and the number of HBD derived from the linker of the TOYO-Pearl resin, the number of HBA is 12 and the number of HBD is 8 in the hydrophilic spacer.

Production Example 50

Synthesis (6-1) of Hydrophilic Spacer Molecule

Synthesis of (2,3,4,5,6-pentahydroxy-hexyl)-carbamic acid 9H-fluoren-9-ylmethyl ester (Compound 35)

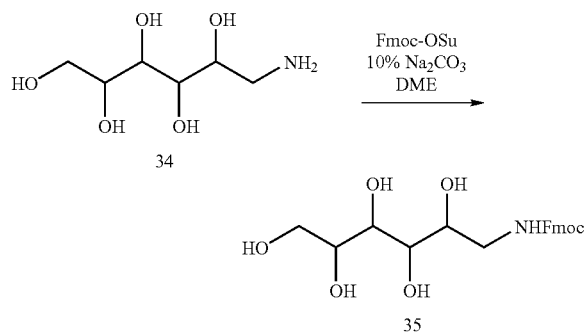

D-glucamine (Compound 34: 9.0 g, 49.7 mmol) was mixed with 200 ml of a 10% aqueous solution of sodium carbonate, and this was followed by stirring under ice cooling. 9-Fluorenylmethylsuccinimidyl carbonate (16.7 g, 49.7 mmol) was dissolved in 200 ml of DME (1,2-dimethoxyethane) and added to the reaction system, and this was followed by stirring under ice cooling for 30 minutes. The precipitating crystal was collected by filtration and washed with H$_2$O×3 and MeOH×3. The crystal was dried under reduced pressure to yield the desired compound (2,3,4,5,6-pentahydroxy-hexyl)-carbamic acid 9H-fluoren-9-ylmethyl ester (Compound 35: 20 g) quantitatively.

$^1$H-NMR(DMSO-d$_6$) δ: 2.99-3.05 (m, 1H), 3.17-3.20 (m, 1H), 3.37-3.48 (m, 3H), 3.56-3.63 (m, 3H), 4.19-4.27 (m, 4H), 4.30-4.33 (m, 1H), 4.39-4.40 (m, 1H), 4.48-4.49 (m, 1H), 4.73 (m, 1H), 7.09-7.13 (m, 1H), 7.35 (t, J=7.2 Hz, 2H), 7.41 (t, J=7.2 Hz, 2H), 7.71 (d, J=7.2 Hz), 7.88 (d, J=7.2 Hz, 2H); MS(m/z) 404 (MH$^+$).

Production Example 51

Synthesis (6-2) of Hydrophilic Spacer Molecule

Synthesis of {6-[bis-(4-methoxy-phenyl)-phenyl-methoxy]-2,3,4,5-tetrahydroxy-hexyl}-carbamic acid 9H-fluoren-9-ylmethyl ester (Compound 36)

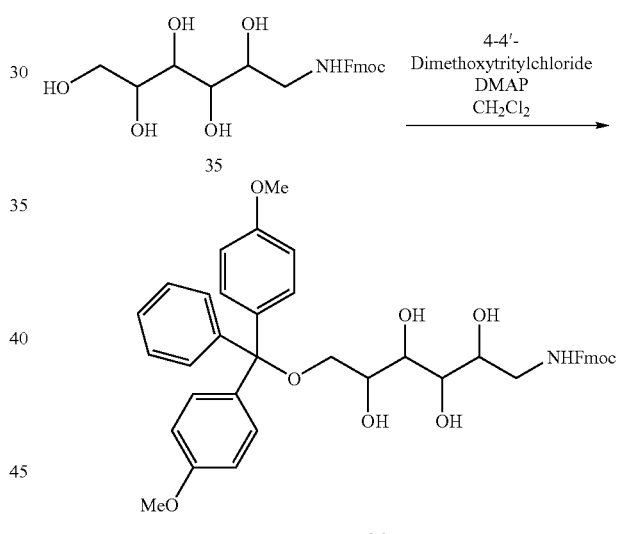

Compound 35 (5.0 g, 12.4 mmol) was dissolved in 100 ml of pyridine and azeotropically boiled. After this operation was conducted two times, the product was dissolved in 100 ml of dry pyridine and cooled with ice in a nitrogen stream. 4,4'-Dimethoxytrityl chloride (5.0 g, 14.9 mmol) and dimethylaminopyridine (1.5 g, 12.4 mmol) were added, the temperature was gradually increased from under ice cooling to room temperature, and this was followed by stirring at room temperature for 17 hours. After the pyridine was evaporated under reduced pressure, the residue was diluted with 500 ml of ethyl acetate. After water was added, the organic phase was separated, after which the water phase was again extracted with ethyl acetate. The ethyl acetate phase was washed with saturated brine, after which it was dried with anhydrous magnesium sulfate. After concentration under reduced pressure, the concentrate was purified by silica gel column chromatography (CHCl$_3$:MeOH=10:1) to yield the desired compound (Compound 36: 5.06 g) at a percent yield of 57.9%.

¹H-NMR(d-acetone) δ: 3.23-3.38 (m, 4H), 3.67-3.95 (m, 6H), 3.77 (s, 6H), 4.05 (d, 1H), 4.18-4.24 (m, 2H), 4.31-4.33 (m, 2H), 6.51 (m, 1H), 6.86 (d, 4H), 7.17-7.42 (m, 1H), 7.51 (d, 2H), 7.70 (d, 2H), 7.86 (d, 2H).

Production Example 52

Synthesis (6-3) of Hydrophilic Spacer Molecule

[6-[bis-(4-methoxy-phenyl)-phenyl-methoxy]-2,3,4,5-tetrakis-(tert-butyldimethyl-silanyloxy)-hexyl]-carbamic acid 9H-fluoren-9-ylmethyl ester (Compound 37)

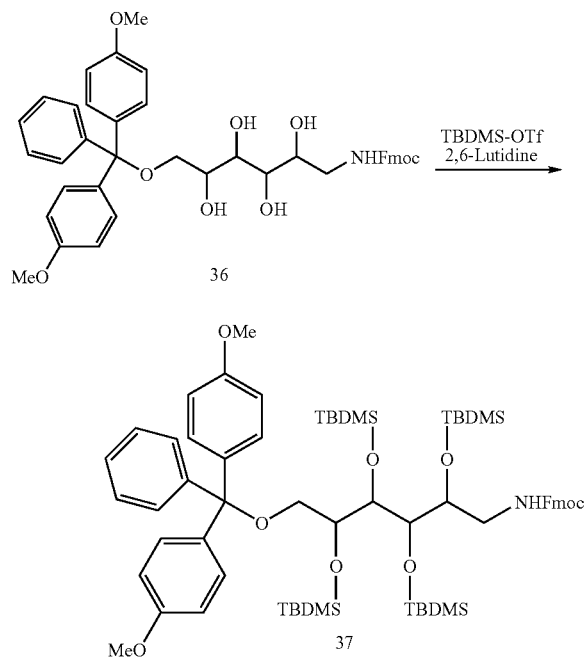

Compound 36 (2.46 g, 3.49 mmol) was dissolved in 2,6-lutidine (15 g, 140 mmol), and this was followed by stirring under ice cooling. Trifluoromethanesulfonic acid tert-butyldimethylsilyl (18.4 g, 69.8 mmol) was gradually added. The temperature was gradually returned from under ice cooling to room temperature, and this was followed by stirring for one day. 200 ml of dichloromethane and 200 ml of water were added, and this was followed by stirring at room temperature for 2 hours. After the organic phase was separated, the water phase was further extracted with 200 ml of dichloromethane. The dichloromethane phase was dried with anhydrous magnesium sulfate and concentrated under reduced pressure. The concentrate was purified by silica gel column chromatography (n-hexane:AcOEt=5:1) to yield the desired compound (Compound 37: 3.5 g) at a percent yield of 86.4%.

¹H-NMR(CDCl₃) δ: −0.1-0.2 (m, 24H), 0.72 (s, 9H), 0.75 (s, 9H) 0.91-0.96 (m, 18H), 3.25 (d, 1H), 3.35-3.50 (m, 3H), 3.59 (m, 1H), 3.75 (s, 6H), 3.80 (m, 1H), 4.03-4.19 (m, 3H), 4.29-4.41 (m, 2H), 5.18 (m, 1H), 6.76 (d, J=8.4 Hz, 4H), 7.15-7.21 (m, 9H), 7.27-7.34 (m, 4H), 7.47 (t, J=7.2 Hz, 2H), 7.65 (d, J=7.2 Hz, 2H).

Production Example 53

Synthesis (6-4) of Hydrophilic Spacer Molecule

Synthesis of [2,3,4,5-tetrakis-(tert-butyldimethyl-silanyloxy)-6-hydroxyhexyl]-carbamic acid 9H-fluoren-9-yl methyl ester (Compound 38)

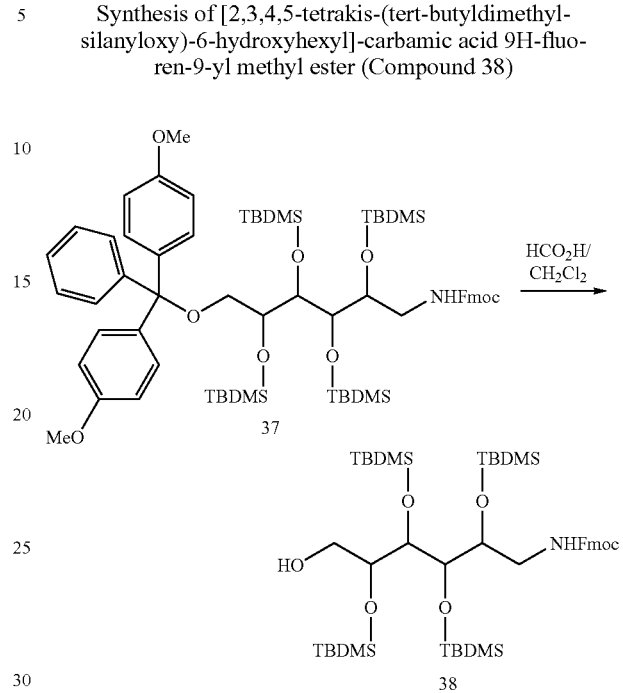

Compound 37 (1.16 g, 1 mmol) was dissolved in 10 ml of a solution (formic acid:dichloromethane=1:10), and this was followed by stirring at room temperature for 2 hours. To saturated aqueous sodium bicarbonate, the reaction solution was poured; extraction was conducted with 100 ml of dichloromethane. The dichloromethane phase was dried with anhydrous magnesium sulfate and purified by silica gel column chromatography (n-hexane:AcOEt=10:1-5:1) to yield the desired alcohol compound (Compound 38: 600 mg) at a percent yield of 69.8%.

¹H-NMR(CDCl₃) δ: −0.50-0.10 (m, 24H), 0.77-0.87 (m, 36H), 2.10 (m, 1H), 3.29-3.36 (m, 1H), 3.43-3.56 (m, 2H), 3.57-3.61 (m, 1H), 3.65-3.71 (m, 1H), 3.75 (m, 1H), 4.03 (m, 1H), 4.09 (m, 1H), 4.27-4.32 (m, 2H), 4.90 (m, 1H), 7.17-7.21 (m, 2H), 7.29 (t, J=7.6 Hz, 2H), 7.49 (t, J=7.6 Hz, 2H), 7.66 (d, J=7.6 Hz, 2H);

MS(m/z) 860 (MH⁺)

Production Example 54

Synthesis (6-5) of Hydrophilic Spacer Molecule

Synthesis of 2,3,4,5-tetrakis-(tert-butyl-dimethyl-silanyloxy)-6-(9H-fluoren-9-ylmethoxycarbonylamino)-hexanoic acid (Compound 39)

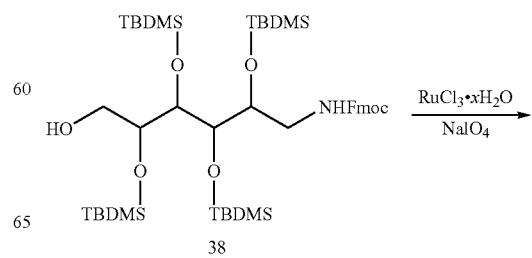

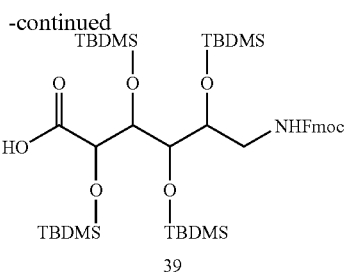

Compound 38 (50 mg, 58.1 μmol) was dissolved by the addition of water (1.5 ml), acetonitrile (4.5 ml) and dichloromethane (0.75 ml). Next, sodium periodate (121 mg, 581 μmol) and then ruthenium chloride (III) hydrate (5 mg, 23 μmol) were added, and this was followed by stirring at room temperature for 3 hours. Ethyl acetate was added thereto, and the organic phase obtained was washed with a 2N aqueous solution of potassium hydrogen sulfate, then with saturated brine, after which it was dried with sodium sulfate. The solid was filtered and concentrated under reduced pressure, after which it was purified by preparative TLC (hexane:ethyl acetate=4:1) to yield the desired 2,3,4,5-tetrakis-(tert-butyl-dimethyl-silanyloxy)-6-(9H-fluoren-9-ylmethoxycarbonylamino)-hexanoic acid (Compound 39: 9.1 mg, 18%).

$^1$H-NMR(CDCl$_3$) δ: 0.07-0.20 (24H, m), 0.91 (36H, m), 3.43 (1H, m), 3.52 (1H, m), 4.00 (1H, m), 4.05 (2H, t, J=5.1 Hz), 4.20 (2H, m), 4.41 (2H, d), 4.53 (1H, s), 7.30 (2H, t, J=7.4 Hz), 7.39 (2H, t, J=7.4 Hz), 7.59 (2H, m), 7.76 (2H, d, J=7.4 Hz); MS (m/z); 874.4 (MH$^+$).

Production Example 55

Synthesis (7-1) of Hydrophilic Spacer Molecule

Synthesis of 4-[N'-(9H-fluoren-9-ylmethoxycarbonyl)-hydrazino]-2,3-dihydroxy-4-oxo-butanoic acid (Compound 41)

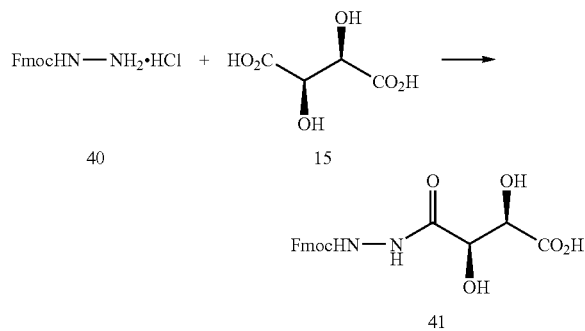

N-(9H-9-fluorenylmethoxycarbonyl)hydrazine hydrochloride (Compound 40; 500 mg, 1.72 mmol) and L-(+)-tartaric acid (Compound 15; 634 mg, 4.22 mmol) were dissolved by the addition of N,N-dimethylformamide (10 ml) and diisopropylethylamine (300 μl, 1.72 mmol). Next, 1-ethyl-3-(3-dimethylaminopropyl)-carbodiimide hydrochloride (485 mg, 2.53 mmol) was added, and this was followed by overnight stirring at room temperature. This was concentrated under reduced pressure; to the residue obtained, aqueous sodium hydrogen carbonate and diethyl ether were added; two liquid phases were separated. The water phase obtained was acidified with a 2N aqueous solution of potassium hydrogen sulfate under ice cooling, after which it was extracted with ethyl acetate. The organic phase was washed with saturated brine, after which it was dried with sodium sulfate. The solid was filtered and concentrated under reduced pressure, after which it was crystallized from methanol-diethyl ether to yield the desired 4-[N'-(9H-fluoren-9-yl-methoxycarbonyl)-hydrazino]-2,3-dihydroxy-4-oxo-butanoic acid (Compound 41: 413 mg, 63%).

$^1$H-NMR(d-acetone) δ: 4.29 (2H, t, J=7.1 Hz), 4.35 (1H, m), 4.60 (1H, s), 4.63 (1H, s), 7.33 (2H, t, J=7.4 Hz), 7.42 (2H, t, J=7.4 Hz), 7.76 (2H, d, J=7.4 Hz), 7.85 (2H, d, J=7.4 Hz); MS (m/z); 387.2 (M$^+$).

Production Example 56

Synthesis of Resin with Hydrophilic Spacer: Synthesis of TOYO-Pearl Resin with Hydrazinotartaric Amide Derivative

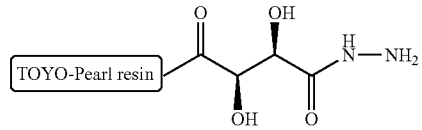

To TOYO-Pearl resin (TSKgel AF-amino; 0.01 mmol amine is present in 100 μl), methylene chloride (0.5 ml) was added; the Compound 41 obtained in Production Example 55 (15.5 mg, 40 μmol), N,N-diisopropylethylamine (16.7 μl, 96 μmol) and PyBOP (25.0 mg, 48 μmol) were further added, and this was followed by overnight shaking at room temperature. After the resin was thoroughly washed with DMF and methylene chloride, methylene chloride (0.5 ml) was added; Compound 41 (15.5 mg, 40 μmol), N,N-diisopropylethylamine (16.7 μl, 96 μmol) and PyBOP (25.0 mg, 48 μmol) were again added, and this was followed by shaking at room temperature for 5 hours. After completion of the reaction, the resin was thoroughly washed with methylene chloride and DMF, after which a mixed solution of acetic anhydride/methanol/methylene chloride (1/1/10) (1.5 ml) was added to the resin obtained, and this was followed by shaking at room temperature for 25 minutes. After completion of the reaction, the resin was thoroughly washed with methylene chloride and DMF, after which a 20% piperidine/DMF solution (0.5 ml) was added, and this was followed by shaking at room temperature for 10 minutes. Next, the resin was washed with DMF, after which a 20% piperidine/DMF solution (0.5 ml) was again added, and this was followed by stirring at room temperature for 20 minutes. After completion of the reaction, the resin was thoroughly washed with methylene chloride and DMF to yield TOYO-Pearl resin with hydrazinotartaric amide derivative [TOYO+(HyT)$_1$].

Production Example 57

Synthesis of Resin with FK506-Derivative-Bound Hydrophilic Spacer (TOYO+(HyT)$_1$–FK506)

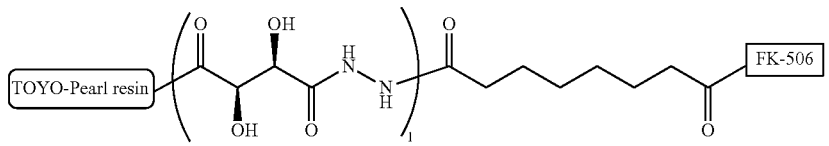

From the TOYO-Pearl resin with hydrazinotartaric amide derivative [TOYO+(HyT)$_1$] obtained in Production Example 56, an FK506-bound resin having a hydrophilic spacer [TOYO+(HyT)$_1$–FK506] was synthesized in accordance with the method described in Production Example 3. In the hydrophilic spacer portion that interlies between the TOYO-Pearl resin and FK506, the number of HBA is 10 and the number of HBD is 7. Note that without considering the number of HBA and the number of HBD coming from the linker of the TOYO-Pearl resin, the number of HBA is 6 and the number of HBD is 4 in the hydrophilic spacer.

Production Example 58

Synthesis of Resin with FK506-Derivative-Bound Hydrophilic Spacer: (TOYO+(HyT)$_2$–FK506)

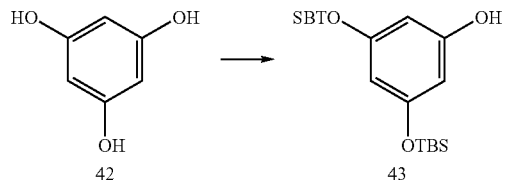

From the TOYO-Pearl resin with hydrazinotartaric amide derivative [TOYO+(HyT)$_1$] obtained in Production Example 56, a hydrophilic spacer elongation reaction was conducted according to Production Example 27. Next, an FK506-bound resin having a hydrophilic spacer [TOYO+(HyT)$_2$–FK506] was synthesized in accordance with the method described in Production Example 3. In the hydrophilic spacer portion that interlies between the TOYO-Pearl resin and FK506, the number of HBA is 16 and the number of HBD is 11. Note that without considering the number of HBA and the number of HBD derived from the linker of the TOYO-Pearl resin, the number of HBA is 12 and the number of HBD is 8 in the hydrophilic spacer.

Production Example 59

Synthesis (8-1) of Hydrophilic Spacer Molecule

Synthesis of 3,5-bis-(tert-butyl-dimethyl-silanyloxy)-phenol (Compound 43)

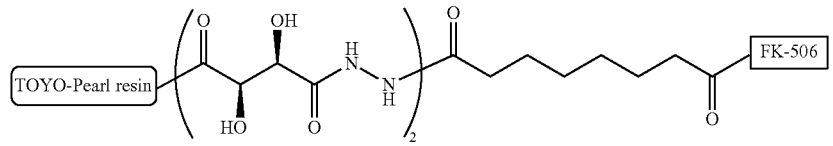

To an ice-cooled solution of benzene-1,3,5-triol (Compound 42; 10 g, 79.3 mmol) in DMF (150 ml), a solution of imidazole (16.2 g, 238 mmol) and tert-butyldimethylsilyl chloride (23.8 g, 158 mmol) in DMF (150 ml) was added; the ice bath was removed, and this was followed by overnight stirring at room temperature. This was poured over water to stop the reaction, after which extraction from ether was conducted. The combined organic phases were washed with saturated brine, thereafter dried with sodium sulfate. Filtration and concentration under reduced pressure were conducted, after which the residue obtained was purified by silica gel column chromatography (Biotage, eluent (n-hexane:ethyl acetate 19:1-9:1)) to yield Compound 43 (white solid 9.8 g, 35%).

MS(m/z): 355.2 MH$^+$, $^1$H-NMR(CDCl$_3$) δ: 0.18 (12H, s), 0.96 (18H, s), 4.58 (1H, s), 5.94-5.97 (1H, m), 5.97-5.98 (2H, m).

Production Example 60

Synthesis (8-2) of Hydrophilic Spacer Molecule

Synthesis of 1,3-bis-(tert-butyl-dimethyl-silanyloxy)-5-[2-(2-{2-[2-(2-trityloxy-ethoxy)-ethoxy]-ethoxy}-ethoxy)-ethoxy]-benzene (Compound 44)

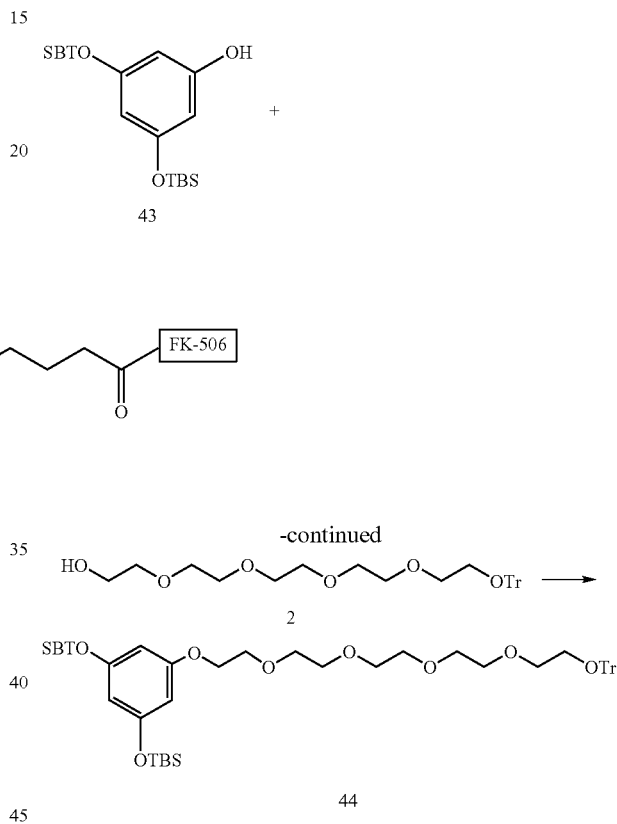

To a solution of Compound 2 (4.3 g, 8.9 mmol) in toluene (20 ml), tributylphosphine (2.35 g, 8.92 mmol) was added at room temperature; this was followed by stirring for 1 hour. This was gradually added to a solution of Compound 43 (3.3 g, 11.6 mmol) and 1,1'-azobis(N,N-dimethylformamide) (2.0 g, 11.6 mmol) in toluene (20 ml), and this was followed by overnight stirring at room temperature. Ethyl acetate (100 ml) was added; the resulting insoluble matter was removed by Celite filtration and washed with ethyl acetate. The combined organic phases were concentrated under reduced pressure; the residue obtained was purified by silica gel column chromatography (Yamazen YFLC Gel, eluent (n-hexane:ethyl acetate 3:1-2:1)) to yield Compound 44 (colorless oil 2.8 g, 39%).

$^1$H-NMR(CDCl$_3$) δ: 0.18 (12H, S), 0.96 (18H, S), 3.23 (2H, t, J=5 Hz), 3.65-3.69 (m, 14H), 3.79 (2H, t, J=5 Hz), 4.04 (2H, t, J=5 Hz), 5.95-5.965 (1H, m), 6.04-6.05 (2H, m), 7.22-7.31 (9H, m), 7.45-7.47 (6H, m).

Production Example 61

Synthesis (8-3) of Hydrophilic Spacer Molecule

Synthesis of 5-[2-(2-{2-[2-(2-trityloxy-ethoxy)-ethoxy]-ethoxy}-ethoxy)-ethoxy]-benzene-1,3-diol (Compound 45)

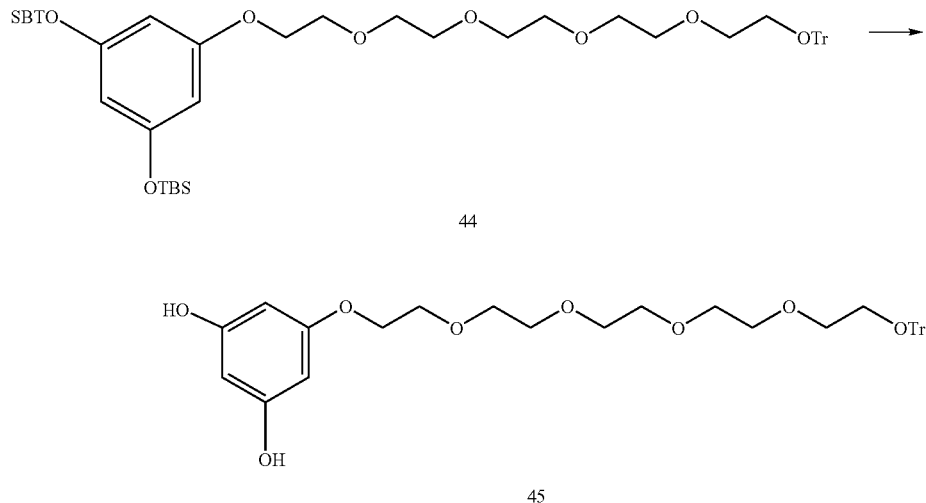

To an ice-cooled solution of Compound 44 (2.81 g, 3.44 mmol) in THF (30 ml), a solution of 1M tetrabutylammonium fluoride in THF (4 ml) was added. After completion of the addition, the ice bath was removed, and this was followed by stirring at room temperature for 1 hour. This was poured over water to stop the reaction, after which extraction from ethyl acetate was conducted. The organic phases were combined and washed with saturated brine, thereafter dried with anhydrous sodium sulfate. Filtration and concentration under reduced pressure were conducted, after which the residue obtained was purified by silica gel column chromatography (Yamazen YFLC Gel, eluent (n-hexane:ethyl acetate 1:1-1:2-1:3)) to yield Compound 45 (light-yellow oil 1.95 g, 96%).

$^1$H-NMR(CDCl$_3$) δ: 3.25 (2H, t, J=5 Hz), 3.62-3.76 (16H, m), 4.02-4.04 (2H, m), 5.80 (2H, s), 5.95 (1H, t, J=2 Hz), 6.03 (2H, d, J=2 Hz), 7.19-7.30 (9H, m), 7.43-7.46 (6H, m).

Production Example 62

Synthesis (8-4) of Hydrophilic Spacer Molecule

Synthesis of 1,3-bis-[2-(2-{2-[2-(2-benzyloxy-ethoxy)-ethoxy]-ethoxy}-ethoxy)-ethoxy]-5-[2-(2-{2-[2-(2-trityloxy-ethoxy)-ethoxy]-ethoxy}-ethoxy)-ethoxy]-benzene (Compound 46)

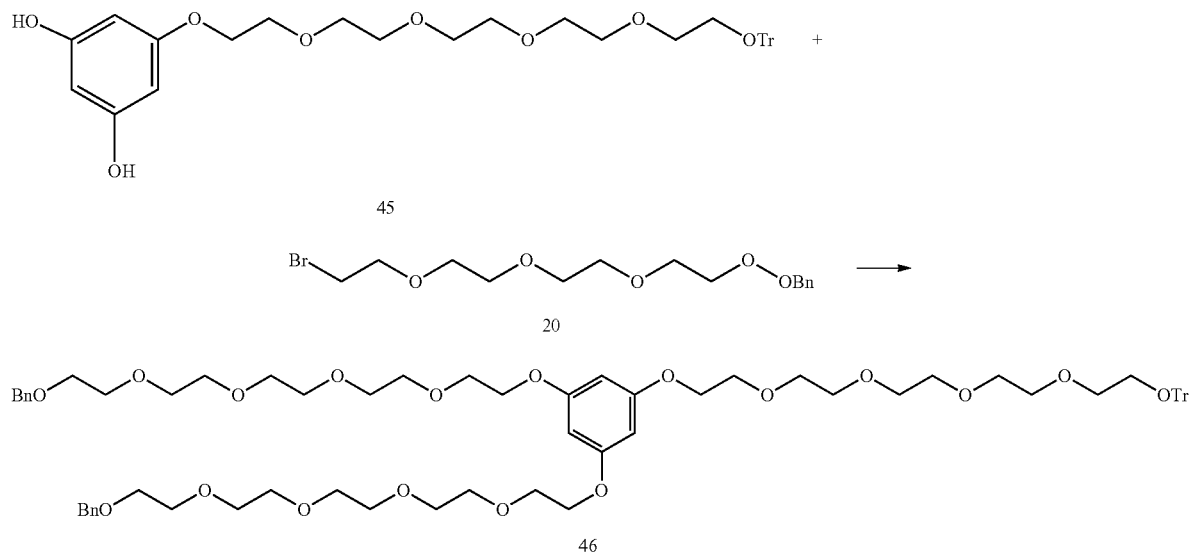

To an ice-cooled mixed suspension of sodium hydride (350 mg, 8.8 mmol; 60% in mineral oil) in THF (4.5 ml) and DMF (1.5 ml), a mixed solution of Compound 45 (1.0 g, 1.7 mmol) in THF (4.5 ml) and DMF (1.5 ml) was gradually added, and this was followed by stirring for 30 minutes. A solution of Compound 20 (2.7 g, 6.8 mmol) in THF (4 ml) was added thereto, and this was followed by stirring for 20 minutes. After the ice bath was removed, stirring was further conducted at room temperature for 4 hours. After the product was again immersed in the ice bath, water was carefully added to stop the reaction, and this was followed by concentration under reduced pressure. Extraction from ethyl acetate was conducted, and the combined organic phases were washed with saturated brine and dried with anhydrous sodium sulfate. Filtration and concentration under reduced pressure were conducted, after which the residue obtained was purified by silica gel column chromatography (Yamazen YFLC Gel, eluent (ethyl acetate-ethyl acetate:methanol 19:1)) to yield Compound 46 (light-yellow oil 1.22 g, 59%).

$^1$H-NMR(CDCl$_3$) δ: 3.23 (2H, t, J=5 Hz), 3.61-3.71 (46H, m), 3.78-3.82 (6H, m), 4.02-4.05 (6H, m), 4.56(4H, s), 6.09 (3H, s), 7.20-7.34(m, 19H), 7.44-7.47 (6H, m).

Production Example 63

Synthesis (8-5) of Hydrophilic Spacer Molecule

Synthesis of 2-(2-{2-[2-(2-{3,5-bis-[2-(2-{2-[2-(2-benzyloxy-ethoxy)-ethoxy]-ethoxy}-ethoxy)-ethoxy]-phenoxy}-ethoxy)-ethoxy]-ethoxy}-ethoxy)-ethanol (Compound 47)

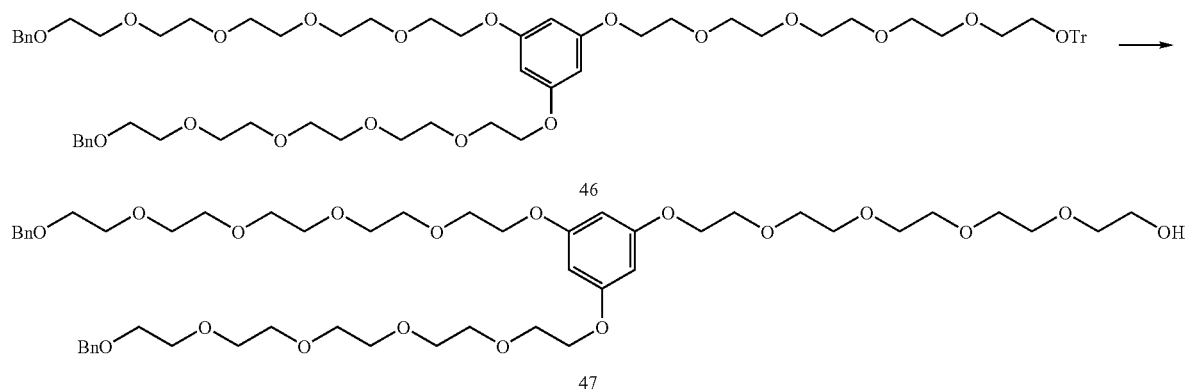

To an ice-cooled solution of Compound 46 (1.22 g, 1.01 mmol) in methylene chloride (15 ml), a methylene chloride solution containing 10% trifluoroacetic acid (7 ml) was added, and water (650 μl) was further added thereto, after which the ice bath was removed, and this was followed by stirring at room temperature for 30 minutes. Triethylamine was poured to the reaction solution, and this was followed by concentration under reduced pressure. The residue obtained was subjected to silica gel column chromatography (Yamazen YFLC Gel, eluent (ethyl acetate-ethyl acetate:methanol 9:1)) to yield Compound 47 (light-yellow oil 977 mg, Y. quant.).

$^1$H-NMR(CDCl$_3$) δ: 3.56-3.73 (48H, m), 3.80-3.84 (6H, m), 4.04-4.09 (6H, m), 4.56 (4H, s), 6.10 (3H, s), 7.28-7.32 (10H, m).

Production Example 64

Synthesis (8-6) of Hydrophilic Spacer Molecule

Synthesis of [2-(2-{2-[2-(2-{3,5-bis-[2-(2-{2-[2-(2-benzyloxy-ethoxy)-ethoxy]-ethoxy}-ethoxy)-ethoxy]-phenoxy}-ethoxy)-ethoxy]-ethoxy}-ethoxy)-ethoxy]-acetic acid tert-butyl ester (Compound 48)

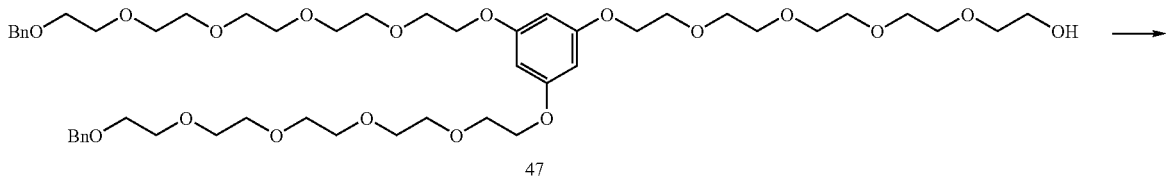

-continued

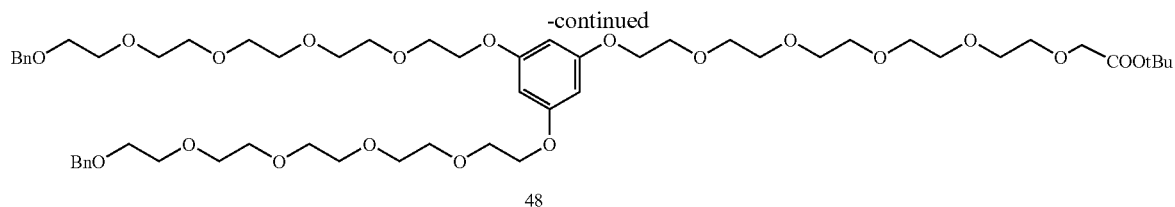
48

To an ice-cooled suspension of sodium hydride (175 mg, 4.4 mmol; 60% in mineral oil) in THF/DMF (4/1 mixed fluid 5 ml), a solution of Compound 47 (1.05 g, 1.09 mmol) in THF (5 ml) was gradually added, and this was followed by stirring for 30 minutes. A solution of bromoacetic acid tert-butyl ester (847 mg, 4.3 mmol) in THF (6 ml) was added thereto. After the ice bath was removed, stirring was further conducted at room temperature for 2 hours. Water was carefully added to stop the reaction, and this was followed by extraction from ethyl acetate, and the combined organic phases were washed with saturated brine and dried with anhydrous sodium sulfate. Filtration and concentration under reduced pressure were conducted, after which the residue obtained was purified by silica gel column chromatography (Yamazen YFLC Gel, eluent (ethyl acetate-ethyl acetate solution containing 5% methanol)) to yield Compound 48 (light-yellow oil 530 mg, 45%).

$^1$H-NMR(CDCl$_3$) δ: 1.47 (9H, s), 3.63-3.71 (48H, m), 3.80-3.83 (6H, m), 4.02 (2H, s), 4.04-4.06 (6H, m), 4.56 (2H, s), 6.09 (3H, s), 7.27-7.34 (10H, m).

Production Example 65

Synthesis (8-7) of Hydrophilic Spacer Molecule

Synthesis of [2-(2-{2-[2-(2-{3,5-bis-[2-(2-{2-[2-(2-hydroxy-ethoxy)-ethoxy]-ethoxy}-ethoxy)-ethoxy]-phenoxy}-ethoxy)-ethoxy]-ethoxy}-ethoxy)-ethoxy]-acetic acid tert-butyl ester (Compound 49)

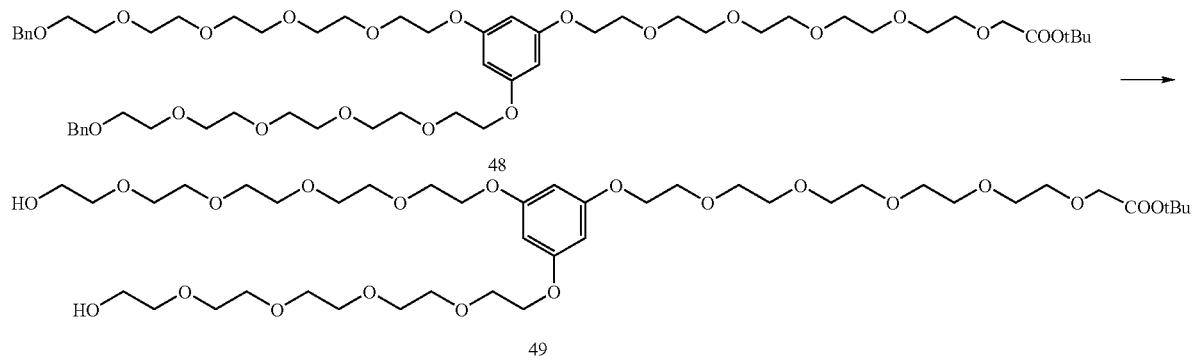

In a nitrogen atmosphere, to a suspension of palladium hydroxide (20% by weight; 90 mg) in methanol (2.7 ml), a solution of Compound 48 (500 mg, 0.462 mmol) in methanol (3.6 ml) was added; after the nitrogen atmosphere was replaced with a hydrogen atmosphere, stirring was conducted at room temperature for about 6 hours. After a nitrogen atmosphere was restored, ethyl acetate (about 20 ml) was added, and the mixture was filtered on silica gel and washed with an ethyl acetate solution containing 10% methanol. Concentration under reduced pressure was conducted to yield a crude product of Compound 49.

$^1$H-NMR(CDCl$_3$) δ: 1.47 (9H, s), 3.59-3.73 (48H, m), 3.81-3.84 (6H, m), 4.02 (2H, s), 4.05-4.08 (6H, m), 6.10 (3H, s).

Production Example 66

Synthesis (8-8) of Hydrophilic Spacer Molecule

Synthesis of (2-{2-[2-(2-{2-[3,5-bis-(2-{2-[2-(toluene-4-sulfonyloxy)-ethoxy]-ethoxy}-ethoxy)-phenoxy]-ethoxy}-ethoxy)-ethoxy]-ethoxy}-ethoxy)-acetic acid tert-butyl ester (Compound 50)

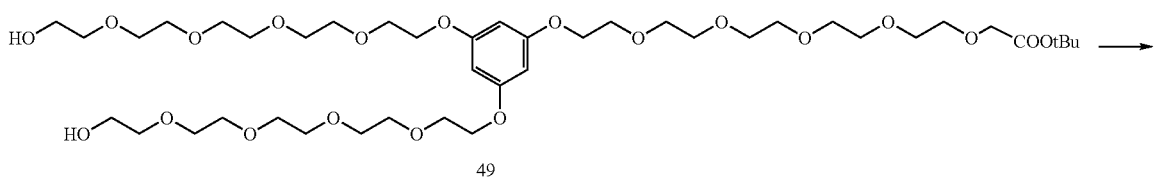
49

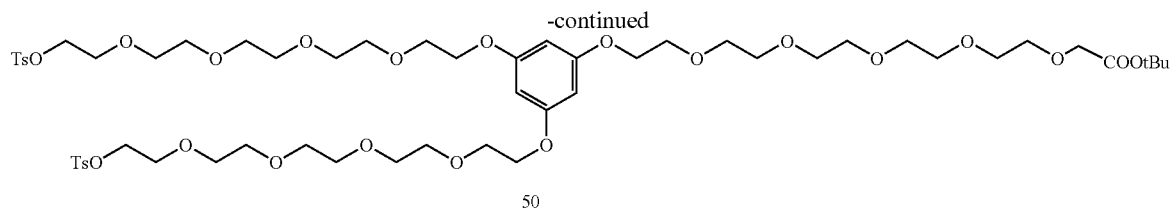

50

To a solution of Compound 49 (146 mg, 0.138 mmol) in pyridine (0.8 ml), 4-dimethylaminopyridine (5.1 mg, 0.041 mmol) was added; after cooling with ice, p-toluenesulfonyl chloride (158 mg, 0.828 mmol) was added, and this was followed by stirring for about 2 hours while heating to 30° C.-40° C. Ice was added thereto to stop the reaction, after which ethyl acetate and water were added. Extraction from ethyl acetate was conducted, the combined organic phases were washed with a saturated aqueous solution of potassium hydrogen sulfate, a saturated aqueous solution of sodium hydrogen carbonate and saturated brine in this order, and dried with sodium sulfate. Filtration and concentration under reduced pressure were conducted, after which the concentrate was purified by silica gel column chromatography (Yamazen YFLC Gel, eluent; ethyl acetate solution containing 10% methanol) to yield Compound 50 (colorless oil 133 mg, 80%, 2 steps).

$^1$H-NMR(CDCl$_3$) δ: 1.47 (9H, s), 3.58-3.83 (54H, m), 4.02 (2H, s), 4.04-4.06 (6H, m), 6.09(3H, s), 7.33 (4H, d, J=8 Hz), 7.79 (4H, d, J=8 Hz).

Production Example 67

Synthesis (8-9) of Hydrophilic Spacer Molecule

Synthesis of [2-(2-{2-[2-(2-{3,5-bis-[2-(2-{2-[2-(2-azido-ethoxy)-ethoxy]-ethoxy}-ethoxy)-ethoxy]-phenoxy}-ethoxy)-ethoxy]-ethoxy}-ethoxy)-ethoxy]-acetic acid tert-butyl ester (Compound 51)

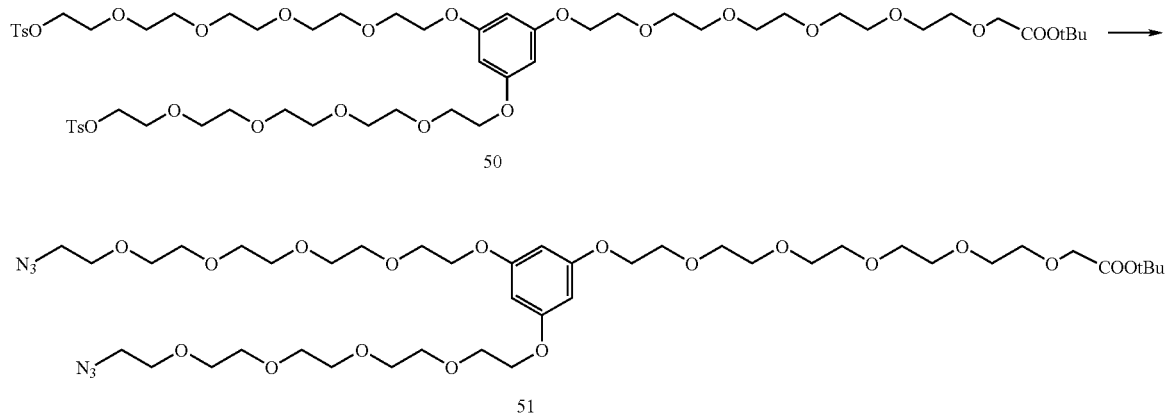

Compound 50 (155 mg, 0.128 mmol) was dissolved in DMF (0.5 ml), and sodium azide (125 mg, 1.9 mmol) was added thereto. The solution was heated to about 60° C., and this was followed by stirring for 90 minutes. The oil bath was removed; after being allowed to cool to room temperature, the solution was diluted with ethyl acetate (10 ml). After a saturated aqueous solution of sodium hydrogen carbonate was further added, extraction from ethyl acetate was conducted. The combined organic phases were washed with saturated brine, thereafter dried with sodium sulfate. Filtration and concentration under reduced pressure were conducted, after which the concentrate was purified by silica gel column chromatography (Yamazen YFLC Gel, eluent; ethyl acetate solution containing 5% methanol) to yield Compound 51 (colorless oil 127 mg, Y. quant).

$^1$H-NMR(CDCl$_3$) δ: 1.47 (9H, s), 3.38 (4H, t, J=5 Hz), 3.66-3.73 (44H, m), 3.82 (6H, t, J=5 Hz), 4.02 (2H, s), 4.06 (6H, t, J=5 Hz), 6.10 (3H, s).

Production Example 68

Synthesis (8-10) of Hydrophilic Spacer Molecule

Synthesis of (2-{2-[2-(2-{2-[3,5-bis-{2-[2-(2-{2-[2-(9H-fluoren-9-ylmethoxycarbonylamino)-ethoxy]-ethoxy}-ethoxy)-ethoxy]-ethoxy}-phenoxy]-ethoxy}-ethoxy)-ethoxy]-ethoxy}-ethoxy)-acetic acid tert-butyl ester (Compound 52)

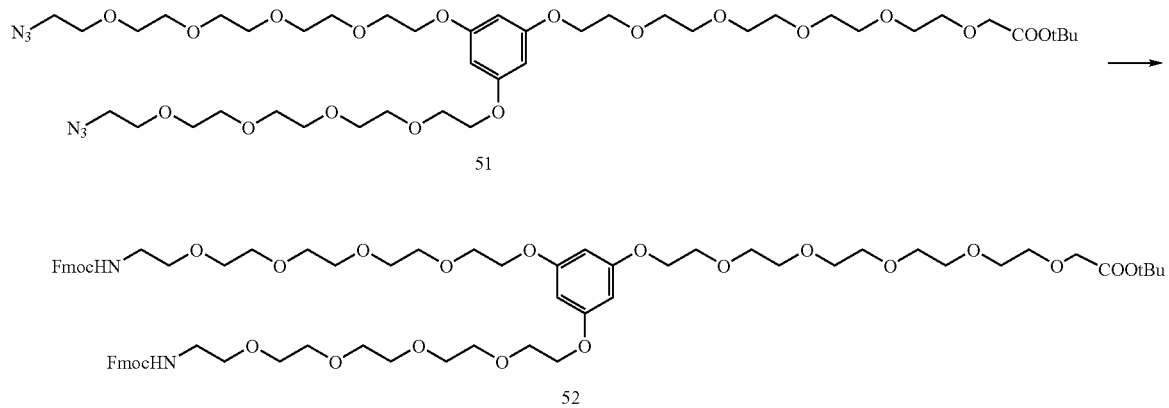

In a nitrogen atmosphere, to a suspension of palladium hydroxide (20% by weight; 15 mg) in methanol (0.5 ml), a solution of Compound 51 (122 mg, 0.323 mmol) in methanol (0.7 ml) was added; after the nitrogen atmosphere was replaced with a hydrogen atmosphere, stirring was conducted at room temperature for 1 hour. After a nitrogen atmosphere was restored, insoluble matter was separated by filtration on Celite and washed with methanol. Concentration under reduced pressure was conducted to yield a crude product of the intermediate.

A solution of the obtained crude product of the intermediate in THF (0.75 ml) was cooled with ice, a solution of 9-fluorenylmethylsuccinimidyl carbonate (91 mg, 0.27 mmol) in THF (0.5 ml) was added thereto, triethylamine (49 mg, 0.49 mmol, 68 µl) was further added, and this was followed by stirring for 55 minutes. After water was added thereto to stop the reaction, extraction from ethyl acetate was conducted, and the combined organic phases were washed with saturated brine and dried with sodium sulfate. Filtration and concentration under reduced pressure were conducted, after which the concentrate was purified by silica gel column chromatography (Yamazen YFLC Gel, eluent; ethyl acetate-ethyl acetate solution containing 10% methanol) to yield Compound 52 (colorless oil 111 mg, 67%, 2 steps).

$^1$H-NMR(CDCl$_3$) δ: 1.47 (9H, s), 3.38-3.39 (4H, m), 3.55-3.83 (50H, m), 4.01 (2H, s), 4.01-4.06 (6H, m), 4.21 (2H, t, J=7 Hz), 4.40 (4H, d, J=7 Hz), 5.43 (2H, brs), 6.08-6.10 (3H, m), 7.29-7.33 (4H, m), 7.39 (2H, m, t, J=7 Hz), 7.60 (2H, d, J=7 Hz), 7.75 (2H, d, J=7 Hz).

Production Example 69

Synthesis (8-11) of Hydrophilic Spacer Molecule

Synthesis of (2-{2-[2-(2-{2-[3,5-bis-{2-[2-(2-{2-[2-(9H-fluoren-9-ylmethoxycarbonylamino)-ethoxy]-ethoxy}-ethoxy)-ethoxy]-ethoxy}-phenoxy]-ethoxy}-ethoxy)-ethoxy]-ethoxy}-ethoxy)-acetic acid (Compound 53)

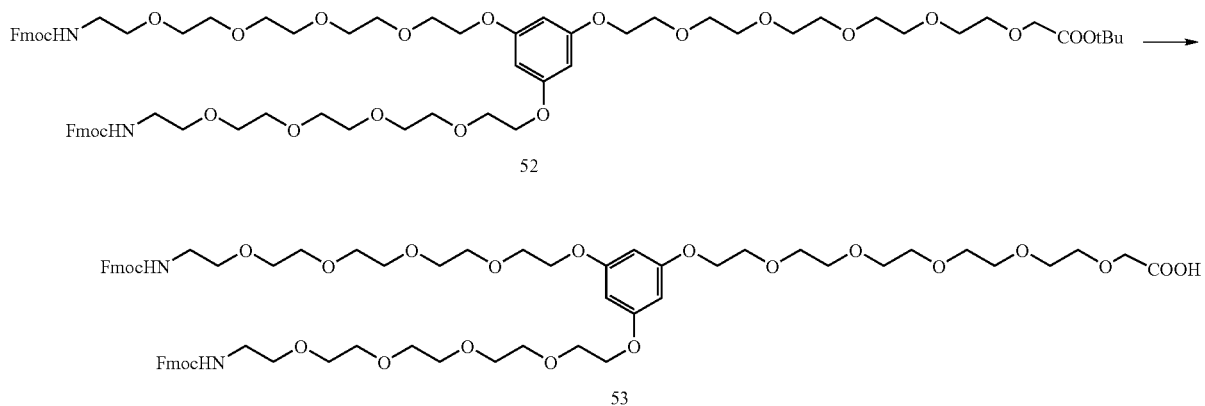

To Compound 52 (106 mg, 0.079 mmol), 5% hydrated trifluoroacetic acid (0.54 ml) was added at room temperature, and this was followed by stirring for 5 minutes. Toluene (about 1 ml) was added; after concentration under reduced pressure, the concentrate was purified by silica gel column chromatography (Yamazen YFLC Gel, eluent; chloroform solution containing 2% methanol-chloroform solution containing 3% methanol-chloroform solution containing 5% methanol) to yield Compound 53 (light-yellow oil 79 mg, 78%).

MS(m/z): 1287.4 MH+, $^1$H-NMR(CDCl$_3$) δ: 3.38-3.39 (4H,m), 3.55-3.83 (50H, m), 4.01-4.06 (6H, m), 4.02-4.07 (4H, m), 4.12 (2H, s), 4.21 (2H, d, J=7 Hz), 4.40 (4H, d, J=7 Hz), 5.46 (2H, brs), 6.08 (3H, m), 7.29-7.33 (4H, m), 7.39 (4H, m, t, J=7 Hz), 7.60 (4H, d, J=7 Hz), 7.75 (4H, d, J=7 Hz).

Production Example 70

Synthesis (9-1) of Hydrophilic Spacer Molecule

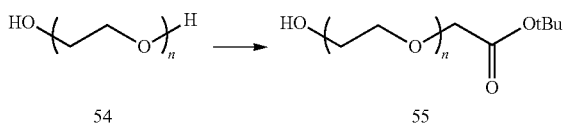

Polyethylene glycol (Compound 54: average molecular weight 2000; 15 g, 7.5 mmol) was dissolved in pyridine (75 ml), triphenylmethyl chloride (2.1 g, 7.5 mmol) and 4-dimethylaminopyridine (0.2 g, 1.6 mmol) were added at room temperature, and this was followed by overnight stirring at 40° C. This was concentrated under reduced pressure; the residue obtained was dissolved in benzene (600 ml), the organic phase was washed with saturated aqueous sodium hydrogen carbonate and saturated brine, after which it was dried with sodium sulfate. The solid was removed by cotton filtration and washed with benzene; the filtrate and the washings were combined and concentrated under reduced pressure to yield a mixture of a monotrityl derivative and a ditrityl derivative (7.6 g). A 5.8 g portion of this mixture was taken and dissolved in a mixed fluid of tetrahydrofuran/N,N-dimethylformamide (4/1; 40 ml), sodium hydride (60% oil suspension; 210 mg) was added at room temperature, and this was followed by stirring for 30 minutes. Tert-butyl bromoacetate (3.9 ml, 15.1 mol) was added thereto at room temperature, and this was followed by stirring for 2 hours. This was cooled to 0° C., and water (1-2 ml) was added little by little, after which benzene (350 ml) was added to the reaction solution, after which the organic phase was washed with saturated brine and dried with sodium sulfate. The solid was removed by cotton filtration and washed with benzene; the filtrate and the washings were combined and concentrated under reduced pressure. The residue obtained was subjected to silica gel column chromatography (Kanto Chemical 60N; 200 ml) with an eluent (10:1 CHCl$_3$-MeOH) to yield 5.2 g of a mixture of the monotrityl-monoacetic acid tert-butyl ester derivative and the ditrityl derivative. This was dissolved in ethanol (80 ml), 10% palladium hydroxide was added, and catalytic hydrogenation (0.3 MPa) was conducted for 5 hours. The solid was removed by Celite filtration and washed with ethanol; the filtrate and the washings were combined and concentrated under reduced pressure. The residue obtained was dissolved in benzene (250 ml); the organic phase was washed with saturated brine, after which it was dried with sodium sulfate. The solid was removed by cotton filtration and washed with benzene; the filtrate and the washings were combined and concentrated under reduced pressure; the residue obtained was subjected to silica gel column chromatography (Kanto Chemical 60N; 200 ml) with an eluent (10:1 CHCl$_3$-MeOH) to yield Compound 55 (2.7 g, 24%, 3 steps).

$^1$H-NMR(CDCl$_3$) δ: 1.48 (9H, s), 3.46-3.83 (m), 4.02 (2H, s).

Production Example 71

Synthesis (9-2) of Hydrophilic Spacer Molecule

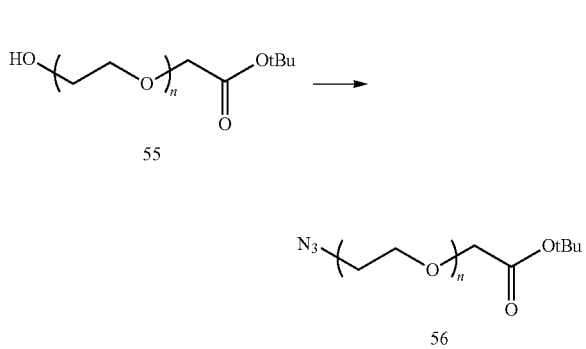

Compound 55 (2.4 g, 1.2 mmol) was dissolved in methylene chloride (30 ml), Molecular Sieves 4A (2 g) was added, and this was followed by overnight stirring; p-toluenesulfonyl chloride (2.16 g, 11.3 mmol) and 4-dimethylaminopyridine (0.72 g, 5.9 mmol) were added thereto at room temperature, and this was followed by overnight stirring. This reaction solution, as is, was subjected to silica gel column chromatography (Kanto Chemical 60N; 250 ml) with an eluent (20:1 CHCl$_3$-MeOH) to yield a tosyl derivative. After the solvent was evaporated, the residue obtained was dissolved in DMSO (24 ml), sodium azide (2.5 g, 38.5 mmol) and sodium iodide (0.4 g, 2.7 mmol) were added, and this was followed by stirring at 70° C. for 5 hours. To the reaction solution, benzene (350 ml) was added; the organic phase was washed with saturated brine, after which it was dried with sodium sulfate. The solid was removed by cotton filtration and washed with benzene; the filtrate and the washings were combined and concentrated under reduced pressure; the residue obtained was subjected to silica gel column chromatography (Kanto Chemical 60N; 150 ml) with an eluent (10:1 CHCl$_3$-MeOH) to yield Compound 56 (1.85 g, 75%, 2 steps).

$^1$H-NMR(CDCl$_3$) δ: 1.47 (9H, s), 3.39 (2H, t), 3.45-3.83 (m), 4.02 (2H, s).

Production Example 72

Synthesis (9-3) of Hydrophilic Spacer Molecule

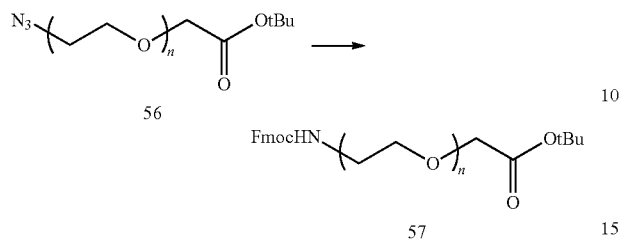

Compound 56 (1.23 g, 0.62 mmol) was dissolved in ethanol (45 ml), 10% palladium hydroxide (250 mg) was added, and catalytic hydrogenation was conducted in a water bath at 35° C. for 2 hours. The solid was removed by Celite filtration and washed with ethanol; the filtrate and the washings were combined and concentrated under reduced pressure to yield the amine compound. This was dissolved in a mixed solvent of 10% aqueous sodium carbonate (15 ml) and acetone (15 ml), 9-fluorenylmethyl succinimidyl carbonate (2 g, 5.9 mmol) was added, and this was followed by stirring at room temperature for 1 hour. To the reaction solution, benzene (150 ml) was added; the organic phase was washed with a saturated potassium hydrogen sulfate solution and saturated brine, after which it was dried with sodium sulfate. The solid was removed by cotton filtration and washed with benzene; the filtrate and the washings were combined and concentrated under reduced pressure; the residue obtained was subjected to silica gel column chromatography (Kanto Chemical 60N; 60 ml) with an eluent (ethyl acetate→10:1 CHCl$_3$-MeOH) to yield Compound 57 (852 mg, 63%, 2 steps).

$^1$H-NMR(CDCl$_3$) δ: 1.47 (9H, s), 3.39 (2H, t), 3.45-3.83 (m), 4.02 (2H, s), 4.23 (1H, m), 4.39 (2H, d), 7.28-7.77 (8H, m).

Production Example 73

Synthesis (9-4) of Hydrophilic Spacer Molecule

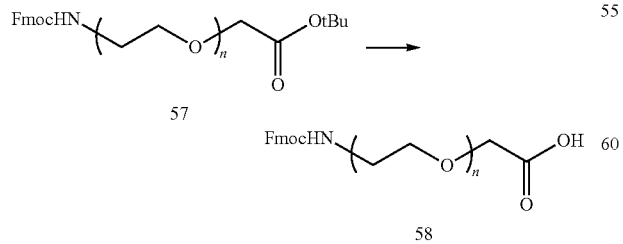

Compound 57 (840 mg, 0.38 mmol) was dissolved in a 95% trifluoroacetic acid solution (8 ml), and this was followed by stirring at room temperature for 1 hour. The reaction solvent was concentrated under reduced pressure; the residue obtained was subjected to silica gel column chromatography (Kanto Chemical 60N; 60 ml) with an eluent (ethyl acetate→4:1 CHCl$_3$-MeOH) to yield Compound 58 (689 mg, 82%).

$^1$H-NMR(CDCl$_3$) δ: 3.39 (2H, t), 3.41-3.83 (m), 4.16 (2H, s) 4.22 (1H, m), 4.40 (2H, d), 7.26-7.77 (8H, m).

Production Example 74

Synthesis of Gold Foil with Hydrophilic Spacer

Synthesis of Gold Foil with Hexaethyleneglycol Derivative (Kojundo Chemical Laboratory Co., Ltd.; Pure Gold, Purity 99.9% Up, Dimensions 10 mm×10 mm×0.01 mm (t))

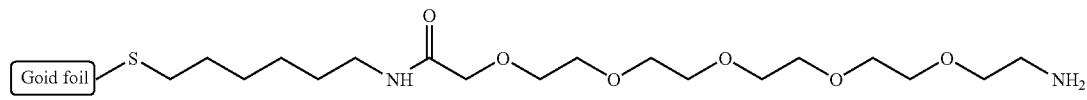

A gold foil (about 1 cm$^2$) immersed in the Piranha solution (30% hydrogen peroxide:concentrated sulfuric acid=1:4 mixed solution) for several hours was washed with MilliQ water (water purified using Millipore pure water production equipment) and ethanol. This was immersed in a solution of (6-mercapto-hexyl)-carbamic acid 9H-fluoren-9-yl-methyl ester in 1.5 mM ethanol (0.5 ml) overnight. After completion of the reaction, the gold foil was thoroughly washed with ethanol and acetonitrile, after which a mixed solution of piperidine/acetonitrile (1/4) (1 ml) was added, and this was followed by shaking at room temperature for 30 minutes. The gold foil was washed with acetonitrile (about 1 ml); the washings and the reaction solution recovered were combined and the fluorene derivative in this solution was quantified, whereby the presence of about 250 pmol of the amine on the gold foil was confirmed.

To this gold foil, {2-[2-(2-{2-[2-(9H-fluoren-9-yl-methoxycarbonylamino)-ethoxy]-ethoxy}-ethoxy)-ethoxy]-ethoxy}acetic acid (Compound 8 obtained in Production Example 11; 12.5 mg, 0.024 mmol) in solution in acetonitrile (0.25 ml) was added; benzotriazol-1-yl-oxy-tris-pyrolidino-phosphonium hexafluorophosphate (PyBOP; 13 mg, 0.025 mmol) in solution in acetonitrile (0.25 ml) and N,N-diisopropylethylamine (8.9 μl, 0.50 mmol) were further added, and this was followed by overnight shaking at room temperature. The reaction solution was removed; after the gold foil was washed with acetonitrile, an overnight reaction was conducted under the same conditions. After completion of the reaction, the gold foil was thoroughly washed with acetonitrile, after which acetic acid (0.3 μl, 0.005 mmol) in solution in acetonitrile (0.25 ml) was added; benzotriazol-1-yl-oxy-tris-pyrolidino-phosphonium hexafluorophosphate (PyBOP; 2.6 mg, 0.005 mmol) in solution in acetonitrile (0.25 ml) and N,N-diisopropylethylamine (1.7 μl, 0.010 mmol) were further added, and this was followed by shaking at room temperature for 3 hours. The gold foil was thoroughly washed with acetonitrile, after which it was treated with a mixed solution of piperidine/acetonitrile (1/4) (1 ml) as described above, and the fluorene derivative was quantified, whereby the condensation rate was determined (about 90%).

Production Example 75

Synthesis of Gold Foil with FK506-Derivative-Bound Hydrophilic Spacer (Gold Foil+(PEG)$_1$-FK506)

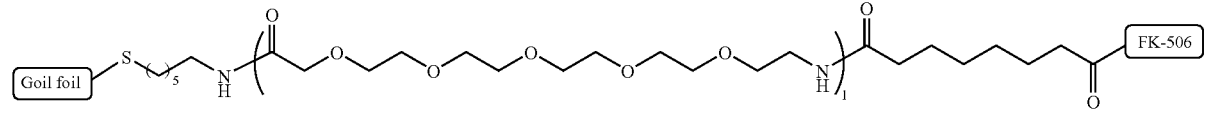

Using the gold foil with hexaethyleneglycol derivative obtained in Production Example 74, a mixture of the 17-allyl-14-(tert-butyl-dimethyl-silanyloxy)-1-hydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone prepared in Production Example 2 (4.8 mg, 0.005 mmol), EDC/HCl (1.0 mg, 0.005 mmol), 1-hydroxybenzotriazol (HOBt; 0.7 mg, 0.005 mmol) and dimethylformamide (DMF; 0.5 ml) was stirred at room temperature overnight. After completion of the reaction, the mixture was thoroughly washed with dimethylformamide (DMF) and acetonitrile to synthesize an FK506-bound gold foil having a hydrophilic spacer+[gold foil+(PEG)$_1$-FK506]. In the hydrophilic spacer portion that interlies between the gold foil and FK506, the number of HBA is 7 and the number of HBD is 1.

Example 1

Binding Experiments (Resins)

(1) Preparation of Lysate

The rat brain (2.2 g) was mixed in a mixed fluid A (0.25M sucrose, 25 mM Tris buffer (pH 7.4), 22 ml) and prepared as a homogenate, which was then centrifuged at 9500 rpm for 10 minutes. The centrifugal supernatant was collected and further centrifuged at 50000 rpm for 30 minutes. The supernatant thus obtained was used as the lysate. Note that all experiments were conducted at 4° C. or on ice.

(2) Binding Experiments

Using the above-described various affinity resins bound with FK506, lysate binding experiments were conducted per the following procedures. Note that the lysate was used after being diluted with the mixed fluid A at a dilution rate of 1/2. Ten microliters of each of the various affinity resins bound with FK506 was used.

Note that as the various affinity resins bound with FK506, resins with FK506-derivative-bound hydrophilic spacers of Production Example 13-18 prepared with different numbers of repeat units of the hexaethylene glycol derivative were used. Also, as a Comparative Example, the TOYO-Pearl resin with FK506 of Production Example 3 was used.

FK506-bound affinity resin and the lysate (1 ml) were gently shaken at 4° C. overnight. Thereafter, the supernatant was removed, and the remaining FK506-bound affinity resin was thoroughly washed four times with mixed fluid A to thoroughly clean the surface of the FK506-bound affinity resin.

To the FK506-bound affinity resin thus obtained, 20 µl of a loading buffer for SDS (Nacalai cat. NO=30566-22, sample buffer solution for electrophoresis with 2-ME (2-mercaptoethanol) (2×) for SDS PAGE) was added; this was followed by heating at 25° C. for 10 minutes. The sample fluid thus obtained was separated using a commercially available SDS gel (BioRad readyGel J, 15% SDS, cat. NO=161-J341), and the SDS gel was analyzed. Of the molecules that had bound (adsorbed) to the TOYO-Pearl resin with FK506 of Production Example 3, which is a Comparative Example, 10 representative kinds of bands were selected, and the amounts of the peaks thereof were measured and quantified for the resins of individual Production Examples and Comparative Examples (FIG. 1). By separately conducted Western blotting, band 10 was identified as the target molecule for FK506, i.e., FKBP12.

As a result, a band reduction or disappearance seemingly based on a nonspecific interaction was observed for ones having the hydrophilic spacer introduced therein. These tendencies were more conspicuous as the number of hexaethylene glycol repeat units increased. On the other hand, for the band of FKBP12 bound to the FK506-bound affinity resin based on a specific interaction (band 10), no band reduction or disappearance due to hydrophilic spacer introduction was observed.

When similar experiments were conducted for other hydrophilic spacers, nonspecific adsorption could be suppressed, though the degree of adsorption differed among different bands.

Experimental Example 1

Correlation Between the Hydrophobic Property of a Solid Phase Surface and Nonspecific Interactions The hydrophobic property of a solid phase surface was altered by immobilizing various compounds of different values of CLOGP onto a solid phase surface, the relation thereof to nonspecific interactions was examined. The compounds used are shown below.

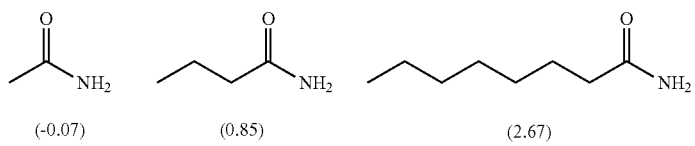

-continued
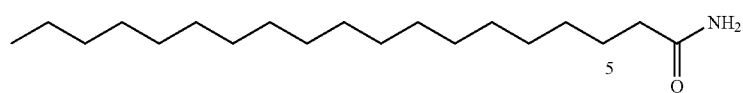
(7.69)
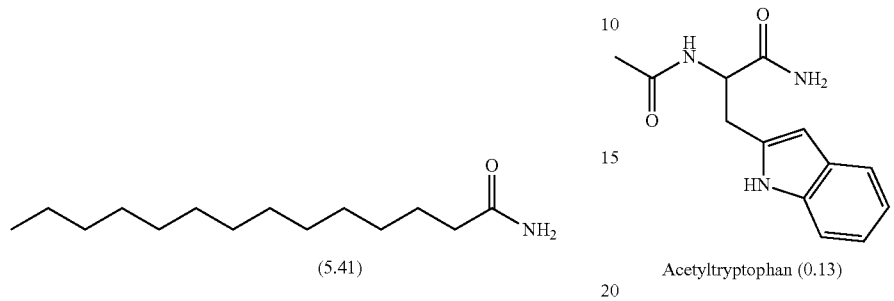
(5.41)    Acetyltryptophan (0.13)
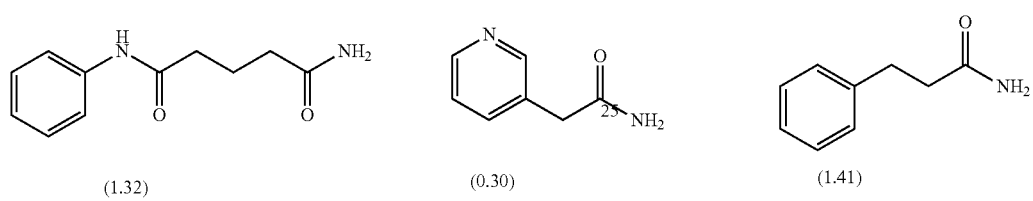
(1.32)    (0.30)    (1.41)
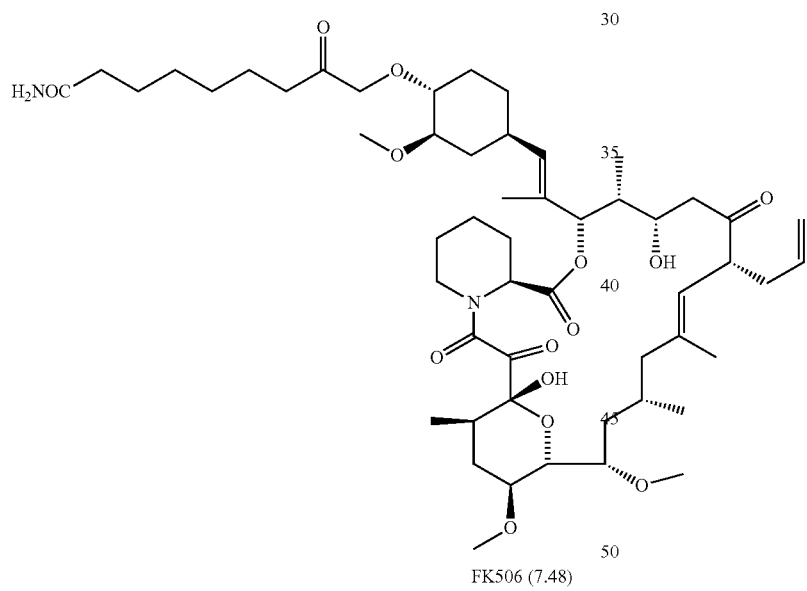
FK506 (7.48)
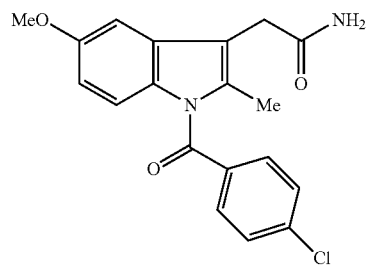
Indomethacin (3.09)
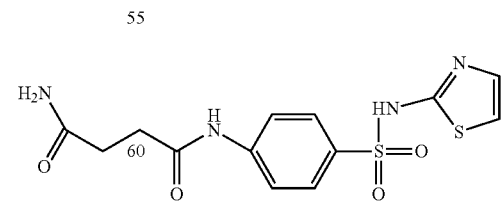
Succinylsulfathizole (0.74)

Figures in parentheses indicate LOGP values (CLOGP values).

Also, immobilization of various compounds on TOYO-Pearl resin was conducted as follows.

(1) Synthesis of Acetic Acid-Immobilized Resin [TOYO+Acetic Acid]

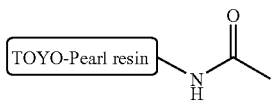

Acetic acid was immobilized onto TOYO-Pearl resin (TSKgel AF-amino).

To 100 µl of the TOYO-Pearl resin, 0.5 ml of a 20% acetic anhydride-DMF solution was added, and this was followed by stirring at room temperature for 4 hours. After completion of the reaction, the resin was thoroughly washed with DMF. The percent condensation yield was determined by the ninhydrin test (about 100%).

(2) Synthesis of Butyric Acid-Immobilized Resin [TOYO+Butyric Acid]

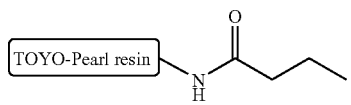

Butyric acid was immobilized onto TOYO-Pearl resin (TSKgel AF-amino).

To 100 µl of the TOYO-Pearl resin, butyric acid (3.40 µl, 0.04 mmol) in solution in a mixed solvent of DMF (0.25 ml) and dichloromethane (0.25 ml) was added; benzotriazol-1-yl-oxy-tris-pyrolidino-phosphonium hexafluorophosphate (PyBOP; 26 mg, 0.05 mmol) and N,N-diisopropylethylamine (17 µl, 0.10 mmol) were further added, and this was followed by shaking at room temperature for 4 hours. After completion of the reaction, the resin was thoroughly washed with DMF, after which the percent condensation yield was determined by the ninhydrin test (about 98%).

(3) Synthesis of Octanoic Acid-Immobilized Resin [TOYO+Octanoic Acid]

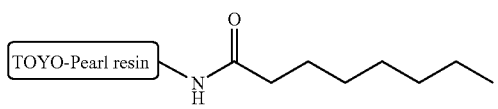

Octanoic acid was immobilized onto TOYO-Pearl resin (TSKgel AF-amino). To a 100 µl portion of the TOYO-Pearl resin, octanoic acid (6.34 µl, 0.04 mmol) dissolved in a mixed solvent of DMF (0.25 ml) and dichloromethane (0.25 ml) was added; PyBOP (26 mg, 0.05 mmol) and N,N-diisopropyl-ethylamine (17 µl, 0.10 mmol) were added, and this was followed by shaking at room temperature for 4 hours. After completion of the reaction, the resin was thoroughly washed with DMF, after which the percent condensation yield was determined by the ninhydrin test (about 97%).

(4) Synthesis of Myristic Acid-Immobilized Resin [TOYO+Myristic Acid]

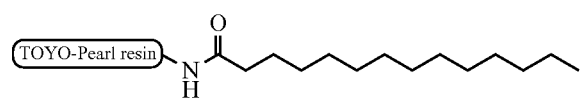

Myristic acid was immobilized onto TOYO-Pearl resin (TSKgel AF-amino). To 100 µl of the TOYO-Pearl resin, myristic acid (9.13 mg, 0.04 mmol) dissolved in a mixed solvent of DMF (0.25 ml) and dichloromethane (0.25 ml) was added; PyBOP (26 mg, 0.05 mmol) and N,N-diisopropyl-ethylamine (17 µl, 0.10 mmol) were further added, and this was followed by shaking at room temperature for 4 hours. After completion of the reaction, the resin was thoroughly washed with DMF, after which the percent condensation yield was determined by the ninhydrin test (about 95%).

(5) Synthesis of Stearic Acid-Immobilized Resin [TOYO+Stearic Acid]

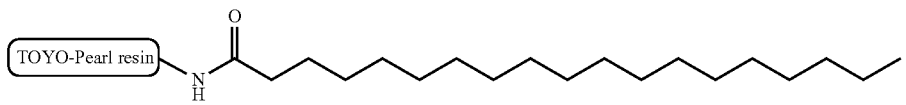

Stearic acid was immobilized onto TOYO-Pearl resin (TSKgel AF-amino). To 100 µl of the TOYO-Pearl resin, stearic acid (11.38 mg, 0.04 mmol) dissolved in a mixed solvent of DMF (0.25 ml) and dichloromethane (0.25 ml) was added; PyBOP (26 mg, 0.05 mmol) and N,N-diisopropyl-ethylamine (17 µl, 0.10 mmol) were further added, and this was followed by shaking at room temperature for 4 hours. After completion of the reaction, the resin was thoroughly washed with DMF, after which the percent condensation yield was determined by the ninhydrin test (about 91%).

(6) Synthesis of Phenylpropionic Acid-Immobilized Resin [TOYO+Phenylpropionic Acid]

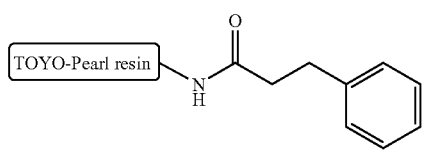

Phenylpropionic acid was immobilized onto TOYO-Pearl resin (TSKgel AF-amino). To 100 µl of the TOYO-Pearl resin, phenylpropionic acid (6.0 mg, 0.04 mmol) dissolved in a mixed solvent of DMF (0.25 ml) and dichloromethane (0.25 ml) was added; PyBOP (26 mg, 0.05 mmol) and N,N-diiso-propylethylamine (17 µl, 0.10 mmol) were further added, and this was followed by shaking at room temperature for 4 hours.

After completion of the reaction, the resin was thoroughly washed with DMF, after which the percent condensation yield was determined by the ninhydrin test (about 97%).

(7) Synthesis of Glutalanylic Acid-Immobilized Resin [TOYO+Glutalanylic Acid]

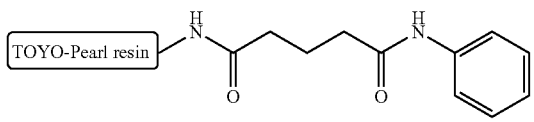

Glutalanylic acid was immobilized onto TOYO-Pearl resin (TSKgel AF-amino). To 100 µl of the TOYO-Pearl resin, glutalanylic acid (8.3 mg, 0.04 mmol) dissolved in a mixed solvent of DMF (0.25 ml) and dichloromethane (0.25 ml) was added; PyBOP (26 mg, 0.05 mmol) and N,N-diisopropylethylamine (17 µl, 0.10 mmol) were further added, and this was followed by shaking at room temperature for 4 hours. After completion of the reaction, the resin was thoroughly washed with DMF, after which the percent condensation yield was determined by the ninhydrin test (about 97%).

(8) Synthesis of 3-Pyridylacetic Acid-Immobilized Resin [TOYO+3-Pyridylacetic Acid]

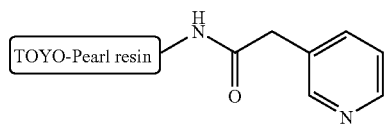

3-Pyridylacetic acid was immobilized onto TOYO-Pearl resin (TSKgel AF-amino). To 100 µl of the TOYO-Pearl resin, 3-pyridylacetic acid (6.9 mg, 0.04 mmol) dissolved in a mixed solvent of DMF (0.25 ml) and dichloromethane (0.25 ml) was added; PyBOP (26 mg, 0.05 mmol) and N,N-diisopropylethylamine (17 µl, 0.10 mmol) were further added, and this was followed by shaking at room temperature for 4 hours. After completion of the reaction, the resin was thoroughly washed with DMF, after which the percent condensation yield was determined by the ninhydrin test (about 96%).

(9) Synthesis of Succinylsulfathiazole-Immobilized Resin [TOYO+Succinylsulfathiazole]

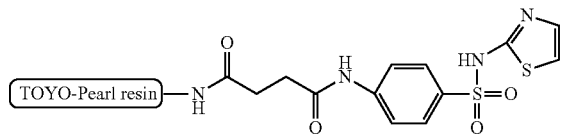

Succinylsulfathiazole was immobilized onto TOYO-Pearl resin (TSKgel AF-amino). To 100 µl of the TOYO-Pearl resin, Succinylsulfathiazole (14.2 mg, 0.04 mmol) dissolved in a mixed solvent of DMF (0.25 ml) and dichloromethane (0.25 ml) was added; PyBOP (26 mg, 0.05 mmol) and N,N-diisopropylethylamine (17 µl, 0.10 mmol) were further added, and this was followed by shaking at room temperature for 4 hours. After completion of the reaction, the resin was thoroughly washed with DMF, after which the percent condensation yield was determined by the ninhydrin test (about 75%).

(10) Synthesis of Indomethacin-Immobilized Resin [TOYO+Indomethacin]

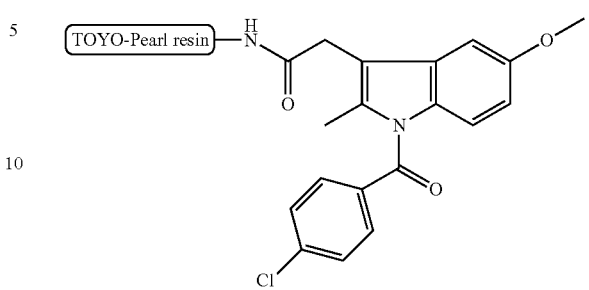

Indomethacin was immobilized onto TOYO-Pearl resin (TSKgel AF-amino). To 100 µl of the TOYO-Pearl resin, indomethacin (14.3 mg, 0.04 mmol) dissolved in a mixed solvent of DMF (0.25 ml) and dichloromethane (0.25 ml) was added, PyBOP (26 mg, 0.05 mmol) and N,N-diisopropylethylamine (17 µl, 0.10 mmol) were further added, and this was followed by shaking at room temperature for 4 hours. After completion of the reaction, the resin was thoroughly washed with DMF, after which the percent condensation yield was determined by the ninhydrin test (about 93%).

(11) Synthesis of N-Acetyltryptophan-Immobilized Resin [TOYO+N-Acetyltryptophan]

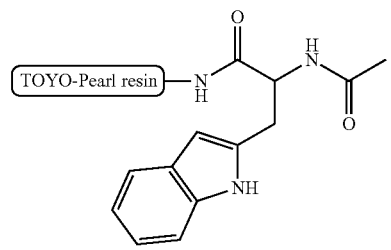

N-acetyltryptophan was immobilized onto TOYO-Pearl resin (TSKgel AF-amino). To 100 µl of the TOYO-Pearl resin, N-acetyltryptophan (9.9 mg, 0.04 mmol) dissolved in a mixed solvent of DMF (0.25 ml) and dichloromethane (0.25 ml) was added; PyBOP (26 mg, 0.05 mmol) and N,N-diisopropylethylamine (17 µl, 0.10 mmol) were further added, and this was followed by shaking at room temperature for 4 hours. After completion of the reaction, the resin was thoroughly washed with DMF, after which the percent condensation yield was determined by the ninhydrin test (about 90%).

Note that the FK506-immobilized resin [TOYO+FK506] used was prepared in Production Example 3.

Using the TOYO-Pearl resins with each compound, lysate binding experiments were conducted. The lysate used was prepared in Example 1 (1).

Binding experiments were also conducted in accordance with Example 1 (2) except that TOYO-Pearl resins immobilized with various compounds were used as solid phase carriers.

Figure 2:
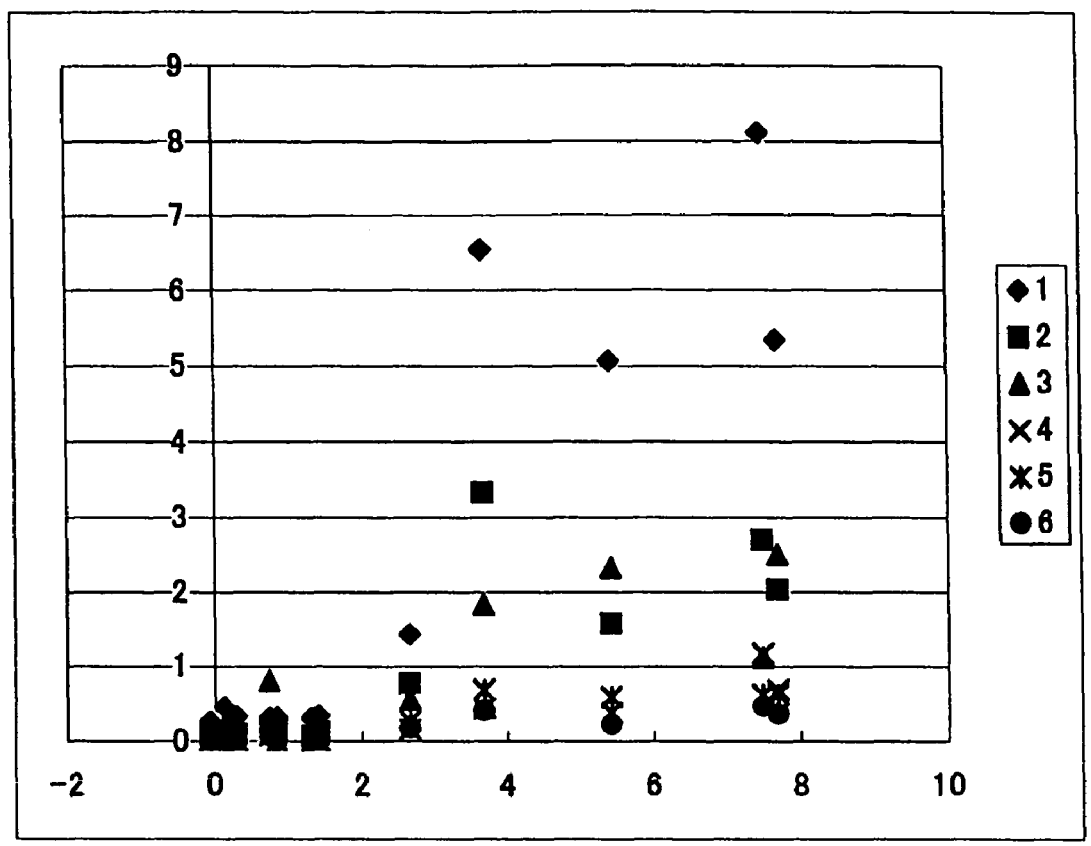
FIG. 2 is a graph showing the relationship between the solid phase surface hydrophobicity and the nonspecific interaction. The ordinate relatively indicates the amounts of six kinds of proteins bound to the solid phase surface, attributable to nonspecific binding, on the basis of the band peak amount in SDS-PAGE. The abscissa indicates the value of CLOGP, which is a hydrophobicity parameter.

Six kinds of bands considered to be based on nonspecific adsorption due to a nonspecific interaction were selected, and the amounts of the peaks thereof were measured and quantified for the resin with each compound. Using CLOGP as the hydrophobicity parameter of each compound, its relation to the peak amount of the band based on nonspecific binding was examined and quantified (FIG. 2). As CLOGP increased, nonspecific binding increased. This result shows that as the hydrophobic property of the solid phase surface intensifies, adsorption by a nonspecific interaction increases.

INDUSTRIAL APPLICABILITY

By introducing a hydrophilic spacer to the binding of a solid phase surface having a hydrophobic property and a ligand that is the subject of examination, nonspecific interactions can be suppressed. Introduction of a hydrophilic spacer is effective even if it is of low extent. Also, this effect can be increased proportionally to the amount of hydrophilic spacer introduced.

In research wherein a small molecule-small molecule, small molecule-large molecule or large molecule-large molecule interaction is measured with one molecule immobilized on a solid phase carrier, or a desired target is purified on the basis of the interaction, it is possible to artificially suppress nonspecific interactions by the technology of the invention of the present application. That is, the present technology also makes easier research wherein a small molecule-small molecule, small molecule-large molecule or large molecule-large molecule interaction is measured with one molecule immobilized on a solid phase carrier, or a desired target is purified on the basis of the interaction. These achievements are widely applicable to all aspects of life science, particularly to drug innovation research, post-genome research, proteomics, chemical genomics, chemical proteomics and the like.

The present application is based on application No. 2002-222226 filed in Japan, and the contents of wihc are incorporated herein by reference.

The invention claimed is:

1. A compound represented by at least two repeated formulas of Formula (IIe) below bound by an amide bond formation reaction

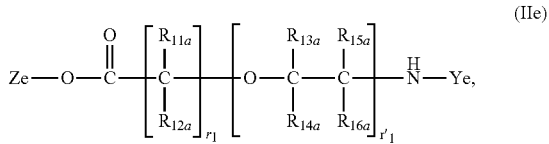

wherein in Formula (IIe),
Ze is a hydrogen atom,
$R_{11a}$-$R_{16a}$ are the same and each is a hydrogen atom, wherein $r_1$ is an integer of 1 and $r_1'$ is an integer of 5, and
Ye is a hydrogen atom.

2. A complex that comprises a solid phase carrier and the compound of claim 1.

3. A solid substrate covalently or non-covalently bound to a hydrophilic spacer comprising the structure represented by Formula (Ie) below:

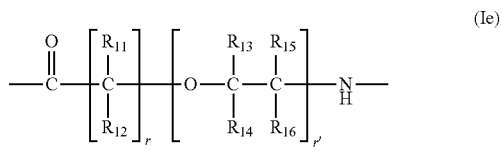

wherein in formula (Ie):
$R_{11}$-$R_{16}$ are hydrogen atoms,
r is an integer of 1, and
r' is an integer of 1-50;
  wherein the solid substrate is a resin selected from the group consisting of polystyrene, methacrylate, and polyacrylamide;
  wherein the solid substrate is metal or glass;
  wherein said hydrophilic spacer is bound to a polynucleotide; or
  wherein the solid substrate is covalently bound to said hydrophilic spacer.

4. The solid substrate of claim 3 which is a resin selected from the group consisting of polystyrene, methacrylate, and polyacrylamide.

5. The solid substrate of claim 3 which is metal.

6. The solid substrate of claim 3 which is glass.

7. The solid substrate of claim 3, which is covalently bound to said hydrophilic spacer.

8. The solid substrate of claim 3, which is non-covalently bound to said hydrophilic spacer.

9. The solid substrate of claim 3, wherein r' in said hydrophilic spacer ranges from 1-5.

10. The solid substrate of claim 3, wherein r' in said hydrophilic spacer is 5.

11. The solid substrate of claim 3, wherein said hydrophilic spacer is bound to a compound having a molecular weight of 1,000 or more.

12. The solid substrate of claim 3, wherein said hydrophilic spacer is bound to a compound having a molecular weight of less than 1,000.

13. The solid substrate of claim 3, wherein said hydrophilic spacer is bound to a protein.

14. The solid substrate of claim 3, wherein said hydrophilic spacer is bound to a polynucleotide.

15. The solid substrate of claim 3, wherein said hydrophilic spacer is bound to a carbohydrate.

* * * * *